(12) United States Patent
Xiao

(10) Patent No.: US 7,691,387 B2
(45) Date of Patent: Apr. 6, 2010

(54) CINNAMOMI AND PORIA COMPOSITION, METHOD TO PREPARE SAME AND USES THEREOF

(75) Inventor: Wei Xiao, Jiangsu (CN)

(73) Assignee: Jiangsu Kanion Pharmaceutical Co., Ltd, Jiangsu (CN)

( * ) Notice: Subject to any disclaimer, the term of this patent is extended or adjusted under 35 U.S.C. 154(b) by 444 days.

(21) Appl. No.: 11/389,441

(22) Filed: Mar. 24, 2006

(65) Prior Publication Data
US 2006/0165721 A1    Jul. 27, 2006

Related U.S. Application Data

(63) Continuation of application No. 10/403,187, filed on Mar. 31, 2003, now Pat. No. 7,052,700, which is a continuation of application No. 09/951,070, filed on Sep. 13, 2001, now Pat. No. 6,569,468, which is a continuation-in-part of application No. PCT/CN00/00273, filed on Sep. 13, 2000.

(51) Int. Cl.
*A61K 36/84* (2006.01)
*A61K 36/736* (2006.01)
*A61K 36/05* (2006.01)
*A61K 36/00* (2006.01)

(52) U.S. Cl. .................. 424/195.15; 424/735; 424/739; 424/773; 424/775; 424/776; 424/725

(58) Field of Classification Search ........................ None
See application file for complete search history.

(56) References Cited

U.S. PATENT DOCUMENTS

| | | | |
|---|---|---|---|
| 5,411,733 A | 5/1995 | Hozumi et al. | |
| 5,466,452 A * | 11/1995 | Whittle | 424/750 |
| 5,874,084 A | 2/1999 | Yng-Wong | |
| 6,569,468 B2 | 5/2003 | Xiao | |
| 6,916,494 B2 * | 7/2005 | Park | 424/725 |
| 7,052,700 B2 | 5/2006 | Xiao | |
| 7,235,265 B2 * | 6/2007 | Rosen | 424/725 |
| 2003/0232102 A1 * | 12/2003 | Zhao | 424/778 |
| 2006/0110468 A1 * | 5/2006 | Liu et al. | 424/725 |

FOREIGN PATENT DOCUMENTS

| | | |
|---|---|---|
| CN | 1081374 A | 2/1994 |
| CN | 1097341 A | 1/1995 |
| CN | 1111524 A | 11/1995 |
| CN | 1113798 | 12/1995 |
| CN | 1125613 A | 7/1996 |
| CN | 1126085 A | 7/1996 |
| CN | 1156047 A | 8/1997 |
| CN | 1166972 A | 12/1997 |
| CN | 1199618 A | 11/1998 |
| CN | 1203805 A | 1/1999 |
| CN | 1206611 A | 2/1999 |
| CN | 1256947 | 6/2000 |
| EP | 1188442 | 3/2002 |
| JP | 62081322 | 4/1987 |
| JP | 62081322 A | 4/1987 |
| JP | 2255621 A | 10/1990 |
| JP | 02255622 A | 10/1990 |
| WO | WO 02/32438 | 4/2002 |
| WO | WO 03884945 | * 10/2003 |
| WO | PCT/IB2007/004483 | 10/2007 |

OTHER PUBLICATIONS

Gu, Yanfang et al., Clinical Application of Guizhi Fuling Wan (GFW) (Pill of Ramulus Cinnamomi and Foria), Journal of Practical Chinese Internal Medicine (Shi Yong Zhong Yi Za Zhi) vol. 7, 2.4-5 (1993).

He, Huiqin et al., Clinical Observation of Guizhi Fuling Jiaonang (GFJ) (Capsule of Ramulus Cinnamomi and Foria) in Treating Gynecological Blood Stasis, Journal of Nanjing College of Traditional Chinese Medicine (Nan Jing Zhong Yi Xue Yuan Xue Bao) vol. 10, 5.16-17 (1994).

Hou, Lidi, Hysteromyoma and Ovarian Cyst Treated Mainly with Guizhi Fuling Wan (GFW) (Pill of Ramulus Cinnamomi and Foria), New Chinese Medicine (Xin Zhong Yi) 4.27-28 (1992).

Jiang, Jiannan et al., Clinical Observation of Guizhi Fuling Jiaonang (GFJ) (Capsule of Ramulus Cinnamomi and Foria) in Treating 45 Cases of Cold Accumulation Pattern of Gynecological Blood Stasis, Chinese Folk Therapy (Zhong Guo Min Jian Liao Fa) 5.35-36 (1998).

Li, Changcheng et al., Guizhi Fuling Wan (GFW) (Pill of Ramulus Cinnamomi and Foria) in Treating Hysteromyoma—Analysis of the Therapeutic Effects in 13 Cases, Journal of Hubei Chinese Medicine (Hu Bei Zhong Yi Za Zhi) Volo. 18, 85.9 (1991).

Liu, Guoxiang, Examples of Clinical Application of Guizhi Fuling Wan (GFW) (Pill of Ramulus Cinnamomi and Foria) in Gynecology, Journal of Anhui Clinical Chinese Medicine (An Hui Zhong Yi Lin Chuang Za Zhi) vol. 10, 6.401-402 (1998).

Shi, Dangmin et al., Clinical Observation of Guizhi Fuling Jiaonang (GFJ) (Capsule of Ramulus Cinnamomi and Foria) in Treating 60 Cases of Hysteromyoma, Chinese Herbal Medicine (Zhong Cao Yao), vol. 31, 5.365 (2000).

Tosa, Kansu et al., Effects of Guizhi Fuling Wan (GFW) (Pill of Ramulus Cinnamomi and Foria) on Blood Viscosity, Blood Platelet Function and Blood Coagulation in Healthy People, Chinese Medicine, Medicine Abroad (Guo Wai Yi Xue, Zhong Yi Zhong Yao Fen Ce) vol. 10, 6.12-15 (1998).

Xie, Jiajun et al., Effects of Guizhi Fuling Wan (GFW) (Pill of Ramulus Cinnamomi and Foria) on Blood Rheology, Research of Chinese Patent Medicine (Zhong Cheng Yao Yan Jiu) 5.24-26 (1986).

(Continued)

*Primary Examiner*—Christopher R. Tate
(74) *Attorney, Agent, or Firm*—Law Offices of Albert Wai-Kit Chan, PLLC

(57) ABSTRACT

This invention provides a method for identifying a composition of *Cinnamomi* and *Poria*. This invention further provides a composition comprising: Ramulus Cinnamomi, Poria Cortex, Moutan Radicis, Radix Paeonize Alba, and Semen Persicae. This invention provides various uses of these compositions.

12 Claims, 4 Drawing Sheets

OTHER PUBLICATIONS

Figure 1:
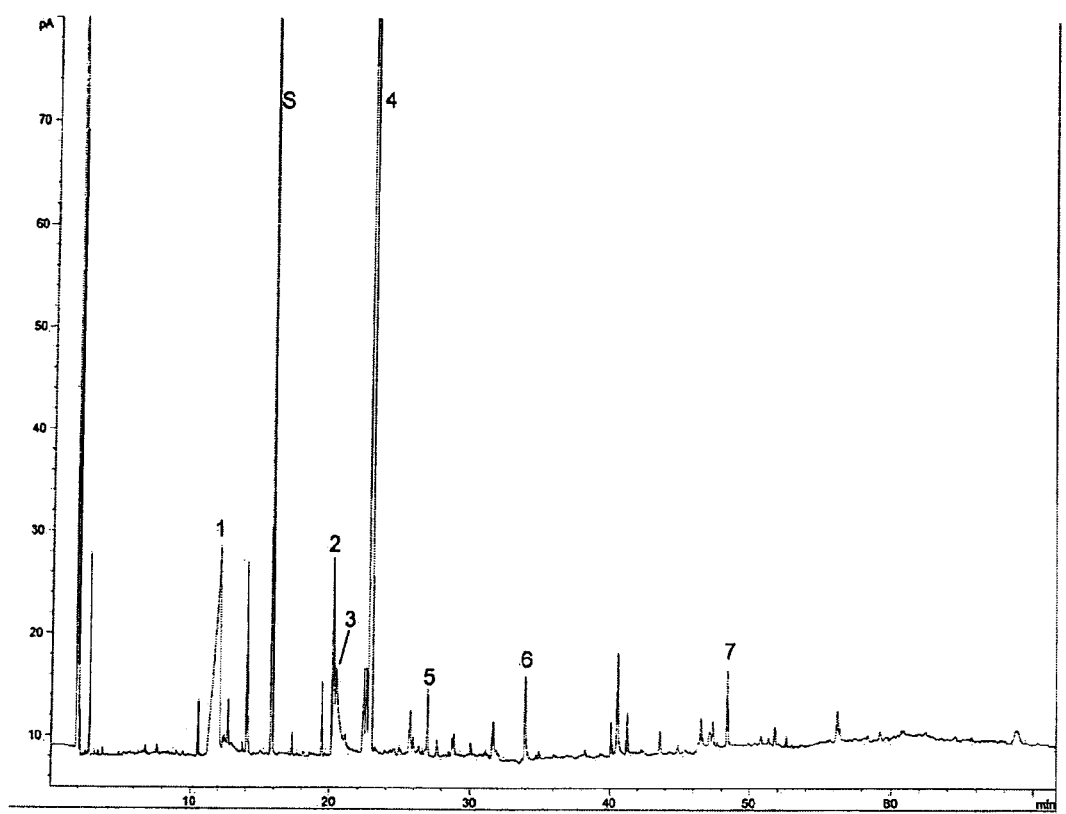

Xie, Jiajun et al., Pharmacological Actions of Guizhi Fuling Wan (GFW) (Pill of Ramulus Cinnamomi and Foria) on the Central Nervous System, Research on Chinese Patent Medicine (Zhong Cheng Yao Yan Jiu) 7.29-30 (1987).

Zeng, Haiju, Clinical Observation of 45 Cases of Hysteromyoma Treated Mainly with Guizhi Fuling Wan (GFW) (Pill of Ramulus Cinnamomi and Foria), Journal of Gansu College of Traditional Chinese Medicine (Gan Su Zhong Yi Xue Yuan Xue Bao) vol. 12, 2.20 (1995).

Zhao, Weiguo, Guizhi Fuling Wan (GFW) (Pill of Ramulus Cinnamomi and Foria) in Treating Benign Tumors in Gynecology, Traditional Chinese Medicine Hebei (He Bei Zhoing Yi) vol. 20, 3.176-177 (1998).

Xu, Zhaoshan, Application of Guizhi Fuling Wan (GFW) (Pill of Ramulus Cinnamomi and Floria) in External Medicine, Information of Traditional Chinese Medicine, 1996(6) pp. 20.

Peng, Qinghua, Clinical Application of Guizhi Fuling Wan (GFW) (Pill of Ramulus Cinnamomi and Foria), Journal of Hunan College of Traditional Chinese Medicine, 1984(2) pp. 60-63.

Li, Chenggong et al., 39 Cases of Hyperlipemia Treated with Guizhi Fuling Wan (GFW) (Pill of Ramulus Cinnamomi and Foria), Jiangxi Traditional Chinese Medicine, 1998(29) No. 1, pp. 19.

Yan, Qi et al., Examples of Clinical Application of Guizhi Fuling Wan (GFW) (Pill of Ramulus Cinnamomi and Foria) in Gynecology, Jilin TCM Journal 1996 No. 5, pp. 37.

Mu, Guili, Clinical Observation of Guizhi Fuling Jiaonang (GFJ) (Capsule of Ramulus Cinnamomi and Foria) in Treating Hysteromyoma, Traditional Chinese Medicine in Gansu (Gan Su Zhong Yi) 2000 (4), pp. 47-48.

Liao, Shizhong et al., Guizhi Fuling Wan (GFW) (Pill of Ramulus Cinnamomi and Foria) in the Treatment of 20 Cases of Preipheral Nervous Lesion due to Diabetes, Traditional Chinese Medicine in Inner Mongolia (Nei Meng Gu Zhong Yi) 1996(2), pp. 8.

Hou, Lili et al., Pharmacological Experiment on Guizhi Fuling Wan (GFW) (Pill of Ramulus Cinnamomi and Foria), Traditional Chinese Medicine in Hebei (He Bei Zhong Yi) 1997(6), pp. 45-46.

Zhang, Bosheng, Theory of Guizhi Fuling Wan (GFW) (Pill of Ramulus Cinnamomi and Foria) in the Prevenetion and Treatment of Ischemic Stroke, Integrated Chinese and Western Medicine for Practical First-aid in Clinic (Zhong Xi Jie He Shi Yong Lin Chuang Ji Jiu) 1997(11) pp. 527-528.

Yan, Xicai et al., 39 Cases of Hyperlipemia Treated by Guizhi Fuling Wan (GFW) (Pill of Ramulus Cinnamomi and Foria), Shan Dong Journal of Traditional Chinese Medicine (Shan Dong Zhong Yi Za Zhi) 1997(10) pp. 444-445.

Xu, Qingwei, Guizhi Fuling Wan (GFW) (Pill of Ramulus Cinnamomi and Foria) in Treating 45 Cases of Hyperplasia of Prostate, Journal of Zhe Jiang College of Traditional Chinese Medicine (Zhe Jiang Zhong Yi Xue Yuan Xue Bao) 2000(2) pp. 40.

He, Jiangua et al., Detecting Techniques of Guizhi Fuling Wan (GFW) (Pill of Ramulus Cinnamomi and Foria), Chinese Pharmacy (Zhong Guo Yao Shi) 2001(3) pp. 197-198.

Feng, Yanqin et al., Gas Chromatography in Content Determination of Paeonol in Guizhi Fuling Wan (GFW) (Pill of Ramulus Cinnamomi and Foria), Journal of China Pharmacology University (Zhong Gua Yao Ke Da Xue Xue Bao) 1994(1) pp. 15-17.

Tsai, et al., 1997, "Evaluation of four prescriptions of traditional Chinese medicine: Syh-Mo-Yiin, Guizhi-Fuling-Wan, Shieh-Qing-Wan, and Syh-Nih-Sann on experimental acute liver damage in rats", Journal of Ethnopharmacology, vol. 55, 213-222.

Mori, et al., 1992, "Supression of Spontaneous Development of Uterine Adenomyosis by a Chinese Herbal Medicine, Keishi-Bukuryo-Gan, in Mice," Planta Medicine, vol. 59, No. 4, 308-311.

Sakamoto, et al., 1988, "Effects of a Chinese Herbal Medicine, Keishi-Bukuryo-Gan, on the Gondal System of Rats", Journal of Ethnopharmacology, vol. 23, No. 2-3, 151-158.

European Partial Search Report, issued Sep. 10, 2002 for Xiao, Wei, European App'l No. 01402366, filed Sep. 13, 2001.

Wen, et al., 1992, "Determination of Cinnamic Acid and Paeoniflorin in Traditional Chinese Medicinal Preparations by High-performance liquid chromatography", Journal of Chromatography, vol. 593, No. 1-2, 191-199.

Sakamoto, et al, 1992, "Pharmacotherapeutic Effects of Kuei-Chih-Fu-Ling-Wan (Keishi-Bukuryo-Gan) on Human uterine Myomas" American Journal of Chinese Medicine, vol. 20, No. 3-4, 313-317.

Patent Abstract of Japan, vol. 15, No. 1 (C-0793), Jan. 7, 1991, and JP 02255621 A (Tsumura & Co.; Others: 01).

U.S. Appl. No. 60/829,945, filed Oct. 18, 2006, Wang et al.

PCT International Search Report for Xiao, Wei, International App'l No. PCT/CN00/00273, filed Sep. 13, 2000, Dated Dec. 7, 2000.

European Office Communication for Jiangsu Kanion Pharmaceuticals, Co. Ltd., et al., European App'l No. 01 402 366.7, filed Sep. 13, 2001, Dated Dec. 14, 2007.

U.S. Office Action for Xiao, Wei, U.S. Appl. No. 09/951,070, filed Sep. 13, 2001, Dated Mar. 26, 2002.

U.S. Office Action for Xiao, Wei, U.S. Appl. No. 09/951,070, filed Sep. 13, 2001, Dated Jul. 3, 2002.

U.S. Notice of Allowance for Xiao, Wei, U.S. Appl. No. 09/951,070, filed Sep. 13, 2001, Dated Jan. 9, 2003.

U.S. Office Action for Xiao, Wei, U.S. Appl. No. 10/403,187, filed Mar. 31, 2003, Dated Jan. 27, 2005.

U.S. Office Action for Xiao, Wei, U.S. Appl. No. 10/403,187, filed Mar. 31, 2003, Dated May 9, 2005.

U.S. Notice of Allowance for Xiao, Wei, U.S. Appl. No. 10/403,187, filed Mar. 31, 2003, Dated Oct. 18, 2005.

Sakamoto, et al., 1992, "Pharmacotherapeutic Effects of Kuei-chih-fu-ling-wan (Keishi-bukuryo-gan) on Human Uterine Myomas", The American Journal of Chinese Medicine, vol. 20 (3/4):313-317.

European Office Communication, Jul. 4, 2008, for Jiangsu Kanion Pharmaceuticals, Co. Ltd., et al., European App'l No. 01 402 366.7, filed Sep. 13, 2001.

European Office Communication, Oct. 6, 2008, for Jiangsu Kanion Pharmaceuticals, Co. Ltd., et al., European App'l No. 01 402 366.7, filed Sep. 13, 2001.

European Office Communication, Dec. 19, 2008, for Jiangsu Kanion Pharmaceuticals, Co. Ltd., et al., European App'l No. 01 402 366.7, filed Sep. 13, 2001.

European Office Communication, Sep. 7, 2009, for Jiangsu Kanion Pharmaceuticals, Co. Ltd., et al., European App'l No. 01 402 366.7, filed Sep. 13, 2001.

European Office Consultation Summary, Oct. 19, 2009, for Jiangsu Kanion Pharmaceuticals, Co. Ltd., et al., European App'l No. 01 402 366.7, filed Sep. 13, 2001.

* cited by examiner

CINNAMOMI AND PORIA COMPOSITION, METHOD TO PREPARE SAME AND USES THEREOF

This application is a continuation application of U.S. Ser. No. 10/403,187, filed Mar. 31, 2003 now U.S. Pat. No. 7,052, 700, which is a continuation of U.S. Ser. No. 09/951,070, filed Sep. 13, 2001, now U.S. Pat. No. 6,569,468, which is a continuation-in-part application of International Application No. PCT/CN00/00273, filed Sep. 13, 2000, the contents of which are hereby incorporated by reference into this application.

Throughout this application, various publications are referenced and full citations for these publications may be found in the references at the end of the specifications preceding the claims. The disclosures of these publications are hereby incorporated by reference into this application in order to more fully describe the state of the art as known to the skilled therein as of the date of the invention described and claimed herein.

BACKGROUND OF THE INVENTION

Menstrual cramps and dysfunctional uterine bleeding are common disorders among women during their menstrual period. Menstrual cramps affect as many as 40 percent of female adults and temporarily disables one-tenth of them. As a newly developed treatment, the present invention—*Cinnamomi* and *Poria* composition, which originated from an old Chinese herb formula, is effective in relieving symptoms of such diseases or disorders.

Menstrual cramps, or dysmenorrhea, as it is called in medical terms, is the reoccurrence of painful uterine cramps during menstruation. Dysmenorrhea can include crampy pain; discomfort in the lower abdomen, lower back and the inner thighs; nausea; vomiting; headache; diarrhea; or fatigue. It normally has an onset of from 2-12 hours before the start of menses and tapers over the next one to two days.

Primary dysmenorrhea accounts for a majority of the cases in which no pathologic lesions can be found in pelvic or laparoscopic examination. Although the exact etiology is unspecified, recent advances in biochemistry of prostaglandins to study chemicals and their role in pathophysiology have now established a rational basis for some cases of dysmenorrhea. The release of prostaglandins is significantly increased during menstruation in these women, and the release can be suppressed to normal levels when non-steroidal anti-flammatory drugs (NSAIDs) are given, since NSAIDs are capable of inhibiting cyclo-oxygenase and synthesis of prostaglandins.

In addition to NSAIDs, oral contraceptives, antispasmodics, and analgesics are commonly used by physicians. Androgen therapy is sometimes used, and a minor surgery called dilation and curettage (D&C) is also adopted in certain cases.

Traditional treatments are associated with a variety of side effects, including ineffectiveness and drug tolerance, and have limited effects. That explains why primary dysmenorrhea is still a problem. The present invention was developed using the most common herbal formulations in Traditional Chinese Medicine (TCM). This invention uses a different approaching characterized by steady effectiveness and relatively low toxicity.

The *Cinnamomi* and *Poria* composition is synthesized to protect women from the pain caused by most common pelvic diseases or disorders. In addition to treating primary and secondary dysmenorrhea and dysfunctional uterine bleeding caused by irregular shedding of uterine endometrium, the composition is also effective in treating chronic pelvic inflammations, inflammatory lower abdominal masses and small intramural hysteromyoma.

Like most TCM products, the *Cinnamomi* and *Poria* composition is prepared from multiple medicinal herbal materials—five cultivated natural plants called Ramulus Cinnamomi, *Poria*, Cortex Moutan, Radix Paeoniae Alba and Semen Persicae. Different in weights and portions of the medicinal herbs for the start-up materials and in the producing courses, *Cinnamomi* and *Poria* composition shares the same formula of five herbs with a previous medicinal preparation—Bolus of *Cinnamomi* and *Poria* (BCP).

BCP, which has long been approved as an effective cure, was a sample of success in medicinal practice in ancient China. The formula of five was sourced from Jinkui Summary, a guide compiled by famous TCM practitioner Zhongjing Zhang, some 1,000 years ago. It was also collected in many medicine directory resources, such as the "Traditional Chinese Medicine Dictionary."

With different courses of preparation, the five-plant formula was always administered in combination with other medicinal herbs. It claims to treat a variety of diseases and disorders, including many indications in the present invention.

As a comparison, while BCP was prepared by the extraction of herbs' water solution—a more traditional way in TCM practice, the present invention is produced by updated technologies which could better preserve its effective ingredients. *Cinnamomi* and *Poria* composition was developed in 1989, and have obtained the Certificate of New Medicine Product Permit by authorities in China.

In regards to the medicinal herb materials and their ingredients involving in present invention, a variety of United States Patents and literatures that taught methods in composing curative compositions from herbs like *Cinnamomi, Poria* etc. A variety of reports from China, country of the inventor, are also cited which were mostly in connection with animal or clinical researches for BCP and certain embodiment of *Cinnamomi* and *Poria* composition.

In U.S. Pat. No. 6,093,403, the formula consist an extract of *Poria* composition up 5 to 20% in weight are been used as a cure or prevention of disorders in sugar balance, diabetes, and such blood circulation diseases such as Angina Pectoris.

*Poria cocos* wolf is being use for treating diseases occurred in area of cardio, cerebro-vascular, and for that of Alzheimer's and depression. In U.S. Pat. No. 5,589,182 contain *Poria cocos* wolf up to 20% of its weight make up.

During the menopause stage for many women, many of them might experience a period, which is called "Hot Flashes". In U.S. Pat. No. 58,740,874, which is a herbal formula for treating women, who are in the stage of Hot Flashes. This herbal formula contains both Peony Root and *Poria Cocos*, making up to 13.3% of the weight of the formula.

U.S. Pat. No. 5,942,233, discloses a composition that consists of semen Persicae (Peach Kernel) up 30% of its weight. This formula is known for usages on blood stimulation and the flow of vital energy.

A pharmaceutical liquid composition which contains Cinnamomi Cortex is disclosed in U.S. Pat. No. 5,225,203 which amount 66 parts and 56 parts in Paeoniae Radix of its weight. This pharmaceutical liquid was used in hospital everywhere for treating patients that are suffering from stroke, arteriosclerosis, hypertension, tachycardia, dyspnea, anxiety, cardiostenosis, acute and chronic convulsion, automatic nervous system disease, and coma.

Another pharmaceutical liquid composition containing Paeoniae Radix and Cinnamomi Cortex are allegedly being used in U.S. Pat. No. 5,133,964, which presents an invention that relates to the preparation of oral and parental natural substance liquids of improve on physical stability. In this formula, it contains about 66 mg of Cinnamomi Cortex and 56 mg of Paeoniae Radix. The formula is also being used for the same treatments as described in U.S. Pat. No. 5,225,203.

U.S. Pat. No. 4,613,591. describes an adminiculum for antitumor agents. The composition consists both of Cinnamomi Cortex and Paeoniae Radix from 2.0 to 4.0 parts of the formula. The composition is used as a control substance for side effects and adminiculum for mitomycin C and doxorubicin.

Xie, J Z et al. published an article in 1986 on BCP's influences on blood flow of rabbits. Xie says that BCP had long been claimed for its effect against hypostasis. In their test on rabbits both with oral and intravenous administration, Xie observed that the whole blood reduced specific viscosity and plasma specific viscosity were lowered, RBC electrophoresis time shortened and fibrinogen reduced.

Tu, Z K S et al. in 1988 reported their research results or oral administration of BCP in 10 health human bodies on their blood flow, blood platelet functions etc. The results showed that the whole blood viscosity was significantly lowered after two weeks of administration, the blood platelet coagulation induced by collagen and ADP and synthesis of thromboxane $B_2$ in blood platelets was also inhibited. But, the diagrams of thrombus elasticity showed no changes.

Xie, J Z et al. reported BCP's effect on central nerve system in 1987. Xie reported that oral and injection of BCP in mice both lead to a significant analgesia and sedation effect to the animals. Xie further pointed out that the half lethal dose was 80.0±10.9 g/kg if given through subcutaneous injection, and over 250 g/kg if given orally.

He, HQ et al. published an article in 1994 on clinical study of *Cinnamomi* and *Poria* composition in 100 cases of gynecopathies: dysfunctional uterine bleeding caused by irregular shedding of uterine endometrim, chronic pelvic inflammations, dysmenorrhea and small intramural hysteromyoma. In comparison with 50 cases of patients that were treated with BCP, observations over multiple complaining symptoms and physical signs had showed no significant difference between the two groups.

Shi, D M et al. reported in 2000 after observing of therapeutic effects of *Cinnamomi* and *Poria* composition in 60 patients with hysteromyoma. Patients accepted physical examination on gynecology, ultrasonic examination and hematochrome test. The effectiveness of treatment was defined as significant improvement: tumor reduced 3-5 cm and enlarged menstrual flow reduced 50% or over; improvement: tumor reduced 2-3 cm and menstrual flow reduced 25% or over and ineffective: under improvement. The results showed in Shi's report that an effective rate of 91.7% was acquired, and among which, 10% of the cases was of significant improvement.

In one embodiment of the invention, Capsule of *Cinnamomi* and *Poria* (CCP) was made. And pre-clinical studies on CCP's pharmacological effects have showed that it has the effects of uterine smooth muscle relaxation, antispasmodic, pain-releasing and anti-inflammation, best explanation for its indication of dysmenorrhea and chronic pelvic inflammations.

*Cinnamomi* and *Poria* composition with different concentrations may cause an inhibitory effect against the contraction of extra-corporeal uterine of rats. It counteracts the acceleration and enhancement of contractions of the extra-corporeal uterine that was induced by oxytocin. *Cinnamomi* and *Poria* composition solution of different concentrations might result in the decrease of blood platelet agglutination rate in rats. The effectiveness had a positive relation with different concentrations. *Cinnamomi* and *Poria* composition could also induce a downfall of blood viscosity in rats administered with it for a few days.

Reaction to pains caused by chemical or heat, mice will twist their bodies or swing their tails. By recording the times of body twisting or tail swinging, an objective index of their feeling of pains could be evaluated. CCP, if given to the animals a few days before the tests, will, within certain scope, relieve them from the body movement.

For the effect of anti-inflammation, it could be observed that with administration of CCP, the weights of mice's swelling ears were reduced obviously. The weight of mice's swelling ear reflects the severity of inflammation in the ear that was smeared with croton oil at its surface a period of time before.

A general study of pharmacology on rats' cardiovascular, respiration and nerve system showed that CCP had no noticeable reverse effect physiologically on the above systems. The acute toxicity test was conducted on 20 mice with 246 g/kg in dosage (a thousand times of human's clinical dosage), administered by gastric injection. No death or any other abnormal activities were found. The 90 days long-term toxicity study was also negative in general health indexes, general blood perimeters, functions and pathological studies of different organs.

The controlled clinical studies of multi diseases and comprehensive evaluations were conducted among women of China. 150 people were involved in the first stage trial (Phase II). No deaths or serious adverse events had been reported. The clinical studies showed positive results in a comprehensive evaluated analysis: the evaluation to a multiple indications: dysmenorrhea, chronic pelvic inflammations and many others.

SUMMARY OF THE INVENTION

This invention provides a method for identifying a composition of *Cinnamomi* and *Poria* comprising the steps of: a) dissolving the composition of *Cinnamomi* and *Poria* with an appropriate aqueous solution mixed with an appropriate organic solvent; and b) performing gas chromatographic analysis using a HP-5 5% phenyl methyl siloxane capillary column.

This invention also provides a method for identifying a composition of *Cinnamomi* and *Poria* comprising the steps of: a) dissolving the composition of *Cinnamomi* and *Poria* with an aqueous solution; and b) separating the dissolved mater with an C 18 column under high pressure liguid chromatography.

This invention furthermore provides a method for identifying a composition of *Cinnamomi* and *Poria* comprising: extracting the composition of *Cinnamomi* and *Poria* by an appropriate organic solvent; using appropriate standard for liposoluble matter in the composition of *Cinnamomi* and *Poria*, as internal control; and performing high pressure liquid chromatography using a C18 column.

Furthermore, this invention provides a composition comprising: a) 1.3-1.9% paeoniflorin and b) 0.7-1.1% Paeonol.

This invention provides a method for obtaining a composition of *Cinnamomi* and *Poria* comprising steps of: a) obtaining, pruning, washing and cutting the plant parts: stem of *Cinnamomum cassia* Presl (Fam. Lauraceae), fungus of *Poria cocos* (Schw.) Wolf (Fam. Polyporaceae), Root of *Paeonia suffruticosa* Andr. (Fam. Ranunculaceae), and fruit of *Prunus* persica (L.) Batsch or Prunus davidiana (Carr.) Franch. (Fam. Rosaceae); b) drying the said plants to form 5 medicinal materials: Ramulus Cinnamomi, Poria Cortex, Moutan Radicis, Radix Paeonize Alba and Semen Persicae; c) Smashing Ramulus Cinnamomi, Semen Persicae and Moutan Radicis into coarse powders and chopping Radix Paeonize Alba into slice; d) Sterilizing the Poria Cortex before granulating 50% of its formula weight into fine powder and filtering the powder; e) putting full amount of powder of Cortex Moutan through a process of hot reflux in water and collecting its distillate; (residue and fluid reserved); f) filtering and vacuum drying said distillate to obtain crude Paeonol; g) dissolving the crude paeonol into 95% alcohol; Slowly adding the solution into saturated water solution of β-cyclodextrin while agitating it at thermostatic 80° C. to form a mixture A; h) exhausted filtering mixture A; washing the residue with anhydrous alcohol and letting it dried, a clathrate A is obtained; i) distilling full amount of Ramulus Cinnamomi in water for four hours and collecting its volatile matter; (residue and fluid reserved) j) dissolving the volatile matter into 95% alcohol; slowly adding the solution into saturated water solution of β-cyclodextrin while agitating it at thermostatic 45° C. to form a mixture B; k) exhausted filtering mixture B; washing the residue with anhydrous alcohol and letting it dried, a clathrate B is obtained; 1) mixing residues from step (f) and (j) with full amount of Radix Paeonize Alba, Semen Persicae, 50% of Poria Cortex and 90% alcohol; extracting the mixture, filtering the extract and recovering alcohol from the filtered extract; (residue reserved) m) adding water in residue from step (m), distilling it and filtering the water extract; n) mixing water extract from step (n), alcohol extract from step (m), fluid from step (f) and step (j); enriching the mixture to form a creamed extractive; o) mixing the creamed extractive with Poria Cortex powder from step (e); grinding the mixture into fine powder after vacuum drying it to form a granule; p) mixing the fine powder with some 60% alcohol and starch gum; Granulating the powder to 30 meshes; q) mixing certain amount of silicon dioxide with clathrate A from step (i) and clathrate B from step (1); and r) mixing the mixture from step (r) with the granule from step (p) to obtain a final granule—the composition of Cinnamomi and Poria.

Furthermore, this invention provides a pharmaceutical composition for treating gynecological blood stasis, cardiocerebral vascular diseases, respiratory system and urinary system diseases comprising the following materials in weight proportion: Ramulus Cinnamomi, 1-2 portion; Poria Cortex, 1-2 portion; Moutan Radicis, 1-2 portion; Radix Paeonize Alba, 1-2 portion; and Semen Persicae, 1-2 portion.

Finally, this invention also provides a method for obtaining a composition comprising: distilling a required amount of Cortex Moutan with water through a process of hot reflux and collecting its distillate, filtering and drying said distillate after its cooling down to obtain crude Paeonol; mixing the residues with required amount of Ramulus Cinnamomi, Radix Paeonize Alba, Semen Persicae and 50% of Poria Cortex, adding alcohol to the mixture and extract, extracting the mixture, filtering the extract to obtain an alcohol extract; adding water to residue from the alcohol extraction, extracting and filtering it to obtain a water extract; Mixing the alcohol extract, water extract and solution from distilling of Cortex Moutan, enriching the mixture to a creamed extract; and granulating the rest 50% of Poria Cortex into fine powder, mixing the fine powder with the creamed extract, granulating the mixture after vacuum drying, mixing the granule with crude Paeonol; and filling the mixture in to capsules to form the product.

DETAILED DESCRIPTION OF THE FIGURES

FIG. 1. Gas Chromatography of CCP's volatile matter

Preparation of the volatile matter: Add 50 ml water and 30 ml ethyl ether to the content of 10 capsules of Cinnamomi and Poria. Extract the solution with reflex on a Water bath of 75° C. for 90 minutes and let it cool down. Extract the water layer of the solution with 20 ml ethyl ether for three times and merge all ethyl ether solutions together. Volatilize to dry up the ethyl ether solution on a water bath of 35° C. and, finally, add ethyl ether to make it 5 ml in volume.

System Requirement: HP-5 5% phenyl methyl siloxane capillary columns (30.0 m×0.32 mm×0.25 um); columns temperature 80° C. (5 min) to 250° C. (10 min) rising at 3° C./min; carrier gas is nitrogen with flow rate 1.5 ml/min; FDI detector with hydrogen 40 ml/min, air 350 ml/min; makeup gas: nitrogen 30 ml/min; inlet system temperature 250° C.; split injection with 50:1 in split ratio and 2 μl. in volume; temperature of detector 280° C.; recording time 72 minutes.

Figure 2:
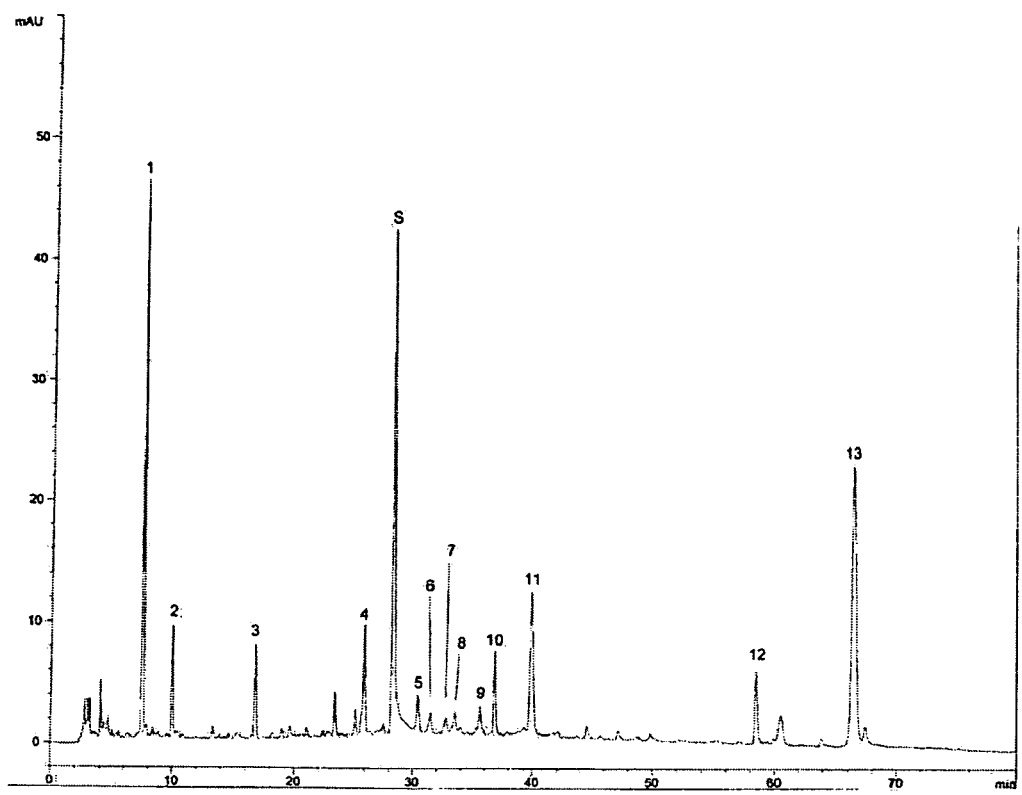

FIG. 2. HPLC of CCP's Water-soluble matter

Preparation of the water-soluble matter: Add 200 ml water to the content of 3 capsules. Extract the solution with reflex for 30 minutes (after boiling) and let it cool down. Centrifuge the solution for 10 minutes and filtrate its supernatant with 0.45 um filter membrane to obtain the filtrate.

System Requirements: Spectrum column: Alltima $C_{18}$ 5 um, 7.5 mm×4.6 mm (guard column) and 250 nm×4.6 mm (spectrum column); column temperature 30° C.; flow rate 1 ml/min, detective wavelength 230 nm; injection volume 5 ul; recording time 70 minutes.

Figure 3:
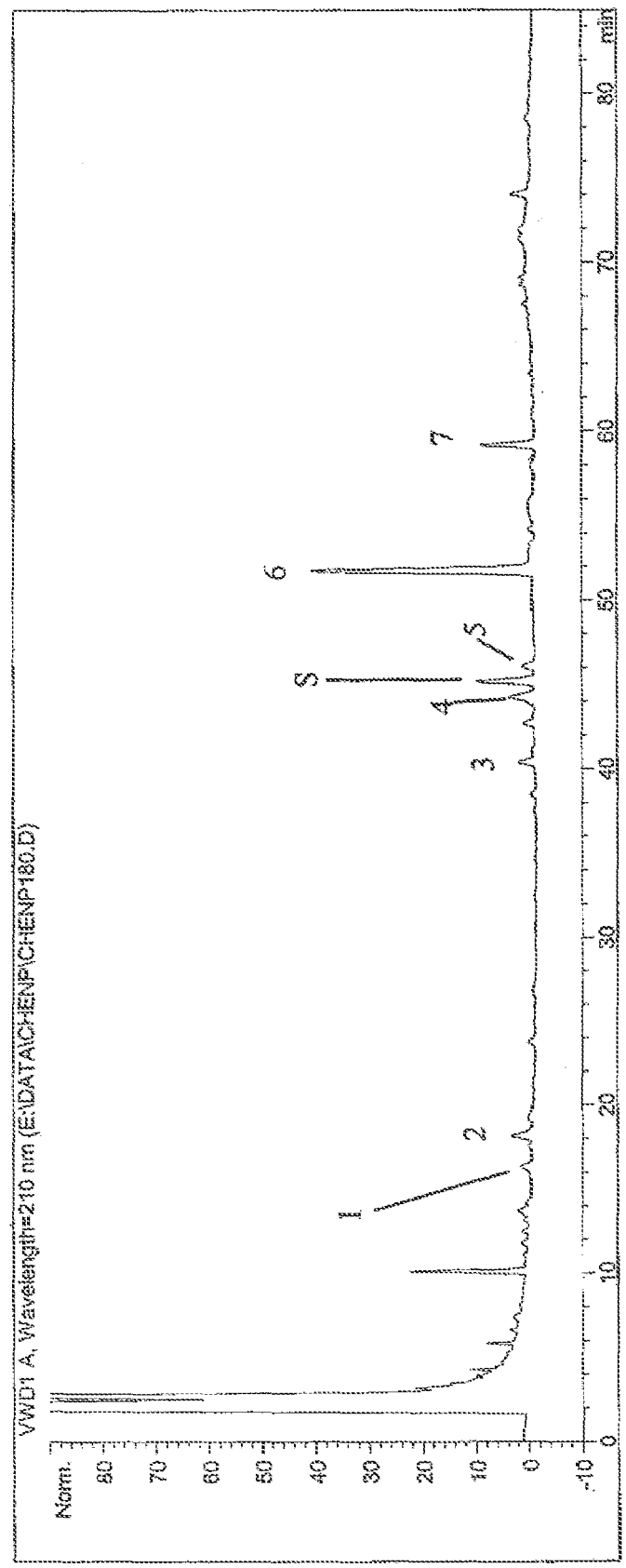

FIG. 3. HPLC of CCP's liposoluble matter in 210 nm of detective wavelength

Preparation of the liposoluble matter: Use the precipitation deposit that obtained from after the centrifugal process in water-soluble solution preparation. Flush the deposit with water until it becomes colorless. Add 20 ml methanol to the deposit, extract the solution with reflex for 30 minutes (after boiling) and let it cool down. Centrifuge the solution for 10 minutes. Volatilize to dry up the methanol from the solution on a water bath of 75° C. And finally, add certain amount of methanol to make the solution to be at 2 ml in volume, filtrate it with 0.45 um filter membrane and obtain the filtrate.

System Requirements: Spectrum column: Alltima $C_{18}$ 5 um, 7.5 mm×4.6 mm (guard column) and 250 nm×4.6 mm (spectrum column); column temperature 50° C.; flow rate 1 ml/min, detective wavelength 210 nm and 242 nm; injection volume 5 ul; recording time 76 minutes.

Figure 4:
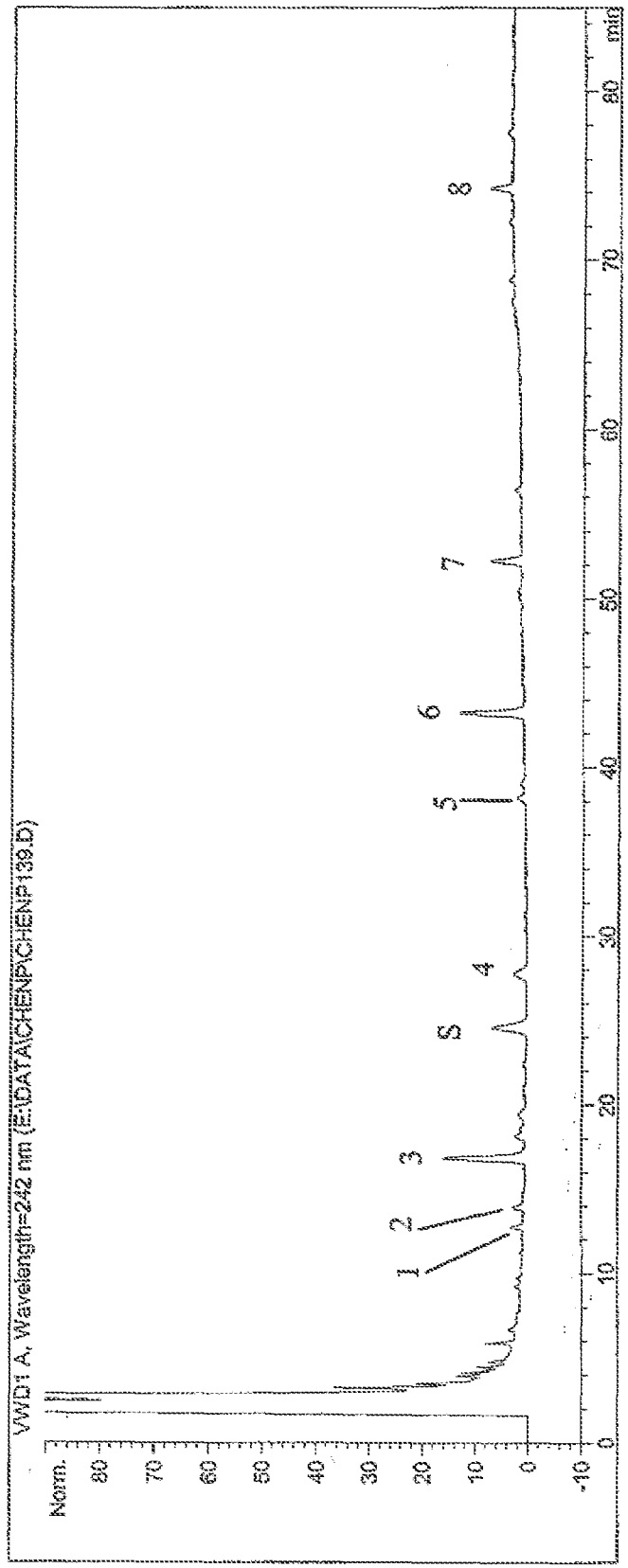

FIG. 4. HPLC of CCP's liposoluble matter in 242 nm of detective wavelength

Preparation of sample solution of liposoluble matter: same with method of FIG. 3.

System Requirements: same with method of FIG. 3.

DETAILED DESCRIPTION OF THE INVENTION

This invention provides a method for identifying a composition of Cinnamomi and Poria comprising the steps of: a) dissolving the composition of Cinnamomi and Poria with an appropriate aqueous solution mixed with an appropriate organic solvent; and b) performing gas chromatographic analysis using a HP-5 5% phenyl methyl siloxane capillary column.

This invention also provides a method for identifying a composition of Cinnamomi and Poria comprising the steps of: a) dissolving the composition of *Cinnamomi* and *Poria* with an aqueous solution; and b) separating the dissolved mater with an C 18 column under high pressure liquid chromatography.

This invention furthermore provides a method for identifying a composition of *Cinnamomi* and *Poria* comprising: extracting the composition of *Cinnamomi* and *Poria* by an appropriate organic solvent; using appropriate standard for liposoluble matter in the composition of *Cinnamomi* and *Poria*, as internal control; and performing high pressure liquid chromatography using a C18 column.

In an embodiment, this invention provides a composition of *Cinnamomi* and *Poria* comprising the product when subjected to the above method produces 7 peaks as shown in FIG. 1. In another embodiment, this invention provides a composition of *Cinnamomi* and *Poria* comprising the product that when subjected to above method produces 13 peaks as shown in FIG. 2. In another embodiment, this invention provides a composition comprising the product when subjected to the above method produces 7 peaks at 210 nm of detective wavelength as shown in FIG. 3. In yet another embodiment, this invention provides a composition comprising the product when subjected to the above method produces 8 peaks at 242 nm of detective wavelength as shown in FIG. 4.

In a separate embodiment, the invention provides a composition comprising the product when subjected to the above method produces a fingerprint as tabulated herein:

| Peak Number | Retention Time/Area | Range of Retention Time | Range of Aria |
|---|---|---|---|
| 1 | 0.757/1.183 | 0.770~0.745 | 1.740~0.690 |
| Standard | 1/1 | | |
| 2 | 1.275 | 1.280~1.270 | |
| 3 | 1.290/0.696 | 1.295~1.285 | 1.110~0.350 |
| 4 | 1.449/5.565 | 1.455~1.440 | 8.080~3.460 |
| 5 | 1.704/0.093 | 1.710~1.700 | 0.140~0.060 |
| 6 | 2.146/0.164 | 2.150~2.140 | 0.255~0.080 |
| 7 | 3.061/0.115 | 3.070~3.055 | 0.160~0.070 |

In another embodiment, this invention provides a composition comprising the product that when subjected to the above method produces a fingerprint as tabulated herein:

| Peak Number | Retention Time/Area | Range of Retention Time | Range of Aria |
|---|---|---|---|
| 1 | 0.261/0.645 | 0.275~0.250 | 0.750~0.460 |
| 2 | 0.349/0.103 | 0.360~0.340 | 0.160~0.070 |
| 3 | 0.584/0.128 | 0.600~0.560 | 0.230~0.065 |
| 4 | 0.915/0.212 | 0.920~0.910 | 0.250~0.170 |
| Standard | 1/1 | | |
| 5 | 1.076/0.089 | 1.085~1.070 | 0.130~0.065 |
| 6 | 1.118/0.046 | 1.125~1.110 | 0.060~0.035 |
| 7 | 1.162/0.052 | 1.175~1.155 | 0.080~0.030 |
| 8 | 1.196/0.083 | 1.210~1.180 | 0.105~0.055 |
| 9 | 1.268/0.076 | 1.285~1.250 | 0.090~0.065 |
| 10 | 1.312/0.211 | 1.330~1.295 | 0.255~0.140 |
| 11 | 1.420/0.404 | 1.450~1.400 | 0.470~0.310 |
| 12 | 2.107/0.149 | 2.170~2.060 | 0.195~0.130 |
| 13 | 2.389/0.981 | 2.465~2.340 | 1.475~0.680 |

In an embodiment, this invention provides a composition comprising the product that when subjected to the above method at 210 nm of detective wavelength produces a fingerprint as tabulated herein:

| Peak Number | Retention Time/Area | Range of Retention Time | Range of Aria |
|---|---|---|---|
| 1 | 0.367/0.322 | 0.375~0.355 | 0.540~0.180 |
| 2 | 0.408/0.580 | 0.420~0.395 | 0.900~0.410 |
| 3 | 0.897/0.280 | 0.905~0.890 | 0.350~0.220 |
| 4 | 0.980/0.752 | 0.985~0.975 | 0.940~0.600 |
| Standard | 1/1 | | |
| 5 | 1.019/0.286 | 1.025~1.015 | 0.410~0.210 |
| 6 | 1.143/4.650 | 1.150~1.135 | 5.950~2.900 |
| 7 | 1.305/0.959 | 1.315~1.295 | 1.450~0.575 |

In still another embodiment, this invention provides a composition comprising the product that when subjected to the above method at 242 nm of detective wavelength produces a fingerprint as tabulated herein:

| Peak Number | Retention Time/Area | Range of Retention Time | Range of Aria |
|---|---|---|---|
| 1 | 0.520/0.155 | 0.530~0.510 | 0.185~0.120 |
| 2 | 0.566/0.184 | 0.570~0.560 | 0.230~0.140 |
| 3 | 0.686/1.385 | 0.690~0.680 | 1.950~0.900 |
| Standard | 1/1 | | |
| 4 | 1.128/0.481 | 1.135~1.125 | 0.530~0.430 |
| 5 | 1.557/0.181 | 1.585~1.525 | 0.240~0.150 |
| 6 | 1.763/1.414 | 1.800~1.720 | 1.700~1.250 |
| 7 | 2.133/0.630 | 2.190~2.070 | 0.840~0.480 |
| 8 | 3.033/0.463 | 3.105~2.950 | 0.680~0.160 |

In another embodiment, the invention provides the above composition, wherein: the retention time (RT) ratios of the 7 peaks in comparison with cinnamaldehyde are 0.757, 1.275, 1.290, 1.449, 1.704, 2.146 and 3.061 respectively; the area ratios of peak 1 and peaks 3-7 in comparison with cinnamaldehyde are 1.183, 0.696, 5.565, 0.093, 0.164, 0.115 respectively; and the range of the retention time ratios of the 7 peaks in comparison with cinnamaldehyde are 0.770-0.745, 1.280-1.270, 1.295-1.285, 1.455-1.440, 1.710-1.700, 2.150-2.140 and 3.070-3.055 respectively; and the range of the area ratios of peak 1 and peaks 3-7 in comparison with cinnamaldehyde are 1.740-0.690, 1.110-0.350, 8.080-3.460, 0.140-0.060, 0.255-0.080 and 0.160-0.070 respectively.

This invention also provides the above composition, wherein: the retention time (RT) ratios of the 13 peaks in comparison with paeoniflorin are 0.261, 0.349, 0.584, 0.915, 1.076, 1.118, 1.162, 1.196, 1.268, 1.312, 1.420, 2.107 and 2.389 respectively; the area ratios of the 13 peaks in comparison with paeoniflorin are 0.645, 0.103, 0.128, 0.212, 0.089, 0.046, 0.052, 0.083, 0.076, 0.211, 0.404, 0.149 and 0.981 respectively; and the range of the retention time ratios of the 13 peaks in comparison with paeoniflorin are 0.275-0.250, 0.360-0.340, 0.600-0.560, 0.920-0.910, 1.085-1.070, 1.125-1.110, 1.175-1.155, 1.210-1.180, 1.285-1.250, 1.330-1.295, 1.450-1.400, 2.170-2.060 and 2.465-2.340 respectively; and the range of the area ratios of the 13 peaks in comparison with paeoniflorin are 0.750-0.460, 0.160-0.070, 0.230-0.065, 0.250-0.170, 0.130-0.065, 0.060-0.035, 0.080-0.030, 0.105-0.055, 0.090-0.065, 0.255-0.140, 0.470-0.310, 0.195-0.130 and 1.475-0.680 respectively.

Furthermore, the invention provides the composition above, wherein: the retention time (RT) ratios of the 7 peaks at 210 nm of detective wavelength in comparison with pachymic acid are 0.367, 0.408, 0.897, 0.980, 1.019, 1.143 and 1.305 respectively; the area ratios of the 7 peaks in comparison with pachymic acid are 0.322, 0.580, 0.280, 0.752, 0.286, 4.650 and 0.959 respectively; and the range of the retention time ratios of the 7 peaks in comparison with pachymic acid are 0.375-0.355, 0.420-0.395, 0.905-0.890, 0.985-0.975, 1.025-1.015, 1.150-1.135 and 1.315-1.295 respectively; and the range of the area ratios of the 7 peaks in comparison with pachymic acid are 0.540-0.180, 0.900-0.410, 0.350-0.220, 0.940-0.600, 0.410-0.210, 5.950-2.900 and 1.450-0.575 respectively.

This invention also provides the above composition, wherein: the retention time (RT) ratios of the 8 peaks at 242 nm of detective wavelength in comparison with polyporenic acid C are 0.520, 0.566, 0.686, 1.128, 1.557, 1.763, 2.133 and 3.033 respectively; the area ratios of the 8 peaks in comparison with polyporenic acid C are 0.155, 0.184, 1.385, 0.481, 0.181, 1.414, 0.630, and 0.463 respectively; and the range of the retention time ratios of the 8 peaks in comparison with polyporenic acid C are 0.530-0.510, 0.570-0.560, 0.690-0.680, 1.135-1.125, 1.585-1.525, 1.800-1.720, 2.190-2.070 and 3.105-2.950 respectively; and the range of the area ratios of the 8 peaks in comparison with polyporenic acid C are 0.185-0.120, 0.230-0.140, 1.950-0.900, 0.530-0.430, 0.240-0.150, 1.700-1.250, 0.840-0.480, 0.680-0.160 respectively.

Furthermore, this invention provides a composition comprising: a) 1.3-1.9% paeoniflorin and b) 0.7-1.1% Paeonol.

In an embodiment, the invention provides the above composition extracted from Ramulus Cinnamomi, *Poria*, Cortex Moutan, Radix Paeoniae Alba and Semen Persicae.

In a separate embodiment, this invention provides the above composition, wherein the Ramulus Cinnamomi, Poria, Cortex Moutan, Radix Paeoniae Alba and Semen Persicae are obtained from cultivated plants.

This invention provides a method for obtaining a composition of *Cinnamomi* and *Poria* comprising steps of: a) obtaining, pruning, washing and cutting the plant parts: stem of *Cinnamomum cassia* Presl (Fam. Lauraceae), fungus of *Poria cocos* (Schw.) Wolf (Fam. Polyporaceae), Root of *Paeonia suffruticosa* Andr. (Fam. Ranunculaceae), and fruit of *Prunus persica* (L.) *Batsch* or *Prunus davidiana* (Carr.) Franch. (Fam. Rosaceae); b) drying the said plants to form 5 medicinal materials: Ramulus Cinnamomi, Poria Cortex, Moutan Radicis, Radix Paeonize Alba and Semen Persicae; c) Smashing Ramulus Cinnamomi, Semen Persicae and Moutan Radicis into coarse powders and chopping Radix Paeonize Alba into slice; d) Sterilizing the Poria Cortex before granulating 50% of its formula weight into fine powder and filtering the powder; e) putting full amount of powder of Cortex Moutan through a process of hot reflux in water and collecting its distillate; (residue and fluid reserved); f) filtering and vacuum drying said distillate to obtain crude Paeonol; g) dissolving the crude paeonol into 95% alcohol; Slowly adding the solution into saturated water solution of β-cyclodextrin while agitating it at thermostatic 80° C. to form a mixture A; h) exhausted filtering mixture A; washing the residue with anhydrous alcohol and letting it dried, a clathrate A is obtained; i) distilling full amount of Ramulus Cinnamomi in water for four hours and collecting its volatile matter; (residue and fluid reserved) j) dissolving the volatile matter into 95% alcohol; slowly adding the solution into saturated water solution of β-cyclodextrin while agitating it at thermostatic 45° C. to form a mixture B; k) exhausted filtering mixture B; washing the residue with anhydrous alcohol and letting it dried, a clathrate B is obtained; l) mixing residues from step (f) and (j) with full amount of Radix Paeonize Alba, Semen Persicae, 50% of Poria Cortex and 90% alcohol; extracting the mixture, filtering the extract and recovering alcohol from the filtered extract; (residue reserved) m) adding water in residue from step (m), distilling it and filtering the water extract; n) mixing water extract from step (n), alcohol extract from step (m), fluid from step (f) and step (j); enriching the mixture to form a creamed extractive; o) mixing the creamed extractive with Poria Cortex powder from step (e); grinding the mixture into fine powder after vacuum drying it to form a granule; p) mixing the fine powder with some 60% alcohol and starch gum; Granulating the powder to 30 meshes; q) mixing certain amount of silicon dioxide with clathrate A from step (i) and clathrate B from step (1); and r) mixing the mixture from step (r) with the granule from step (p) to obtain a final granule— the composition of *Cinnamomi* and *Poria*.

In an embodiment, the invention provides a method for obtaining a composition of *Cinnamomi* and *Poria* composition above further comprising the steps of: I. in step (e) filtering the powder with a 100 meshes sift; in step (f) soaking Cortex Moutan in water for four hours before distillation; in step (g) vacuum drying the distillate at below 55° C. and the concentration of crude paeonol should be no less than 80%; in step (i) and (1) continuously agitating the mixtures at thermostatic 80° C. (mixture A) and 45° C. (mixture B) for another 3 hours and storing it for 24 hours in a refrigerator before it is filtered; drying the clathrates to less than 2% moisture; in step (j) soaking Ramulus Cinnamomi in water for six hours before distillation and testing the presence of cinnamaldegyde in the volatile matter; in step (m) extracting the mixture twice for two hours each in 3 times weight of residues and medicinal materials of 90% alcohol; in step (n) distilling the residue from step (m) twice for two hours each in 4 times weight of the residues of water; in step (o) enriching the mixture in vacuum at temperature below 55° C. to a relative density of no less than 1.27 (75-80° C.); in step (p) vacuum drying the powder at below 55° C.; in step (q) vacuum drying the powder at below 55° C.; in step (r) mixing the clathrates with silicon dioxide in a high performance mixer; and mass balance in formula and above-mentioned respective steps should be at ±5%.

In a separate embodiment, the creamed extractive from step (o) is no less than 1.27 in relative density; component of paeoniflorin is 1.8%-2.7%; and limit of heavy metal is 5 ppm. In another embodiment, the fine powder from step (p) is no more than 5.0% in moisture; component of paeoniflorin is 1.4%-2.2%; and limit of heavy metal is 5 ppm. In yet another embodiment, the clathrates is no more than 2.0% in moisture; Paeonol and cinnamaldehyde tests are positive; and limit of heavy metal is 5 ppm. In yet another embodiment, the final granule from step (s) is no more than 4.0% in moisture; cinnamaldehyde tests is positive; component of paeoniflorin is 1.3%-1.9%; component of Paeonol is 0.7%-1.1%; and limit of heavy metal is 10 ppm.

This invention further provides the composition comprising the product produced by the methods above.

In addition, this invention provides a method for determination of total paeoniflorin and total paeonol in a *Cinnamomi* and *Poria* composition comprising steps of: a) preparing the assay comprising the steps of: accurately weighing a suitable amount of standard paeoniflorin; dissolving it in chromatographically pure methanol to form a standard solution containing 0.9 mg. of standard paeoniflorin per 1 ml; diluting said standard solution of paeoniflorin to 18.0 µg./ml standard solution before using; accurately weighing a suitable amount of standard paeonol; dissolving it in chromatographically pure methanol to form a standard solution containing 0.3 mg. of standard paeonol per 1 ml; diluting said standard solution of paeonol to 6.0 µg./ml standard solution before using; accurately weighing approximately 0.5 g. of granular of *Cinnamomi* and *Poria* composition; and dissolving it with 20 ml. water to form a water solution; putting said solution in ultrasound for 10 minutes for dispersing; extracting the solution in a separating funnel with 30 ml. analytical pure chloroform each time for 5 times; obtaining a solution A by combining the extracts; distilling solution A on a water bath of 70° C. to a suitable volume; mixing it with analytically pure chloroform to a constant volume of 50 ml in a measuring flask; VII. accurately sucking 5 ml. of the 50 ml. solution from step (VI); mixing it with analytically pure chloroform to a constant volume of 50 ml; and filtrating the diluted solution with 0.45 µm. filtration membrane to obtain a sample solution I; extracting the water solution left from step (V) with analytical pure water saturated n-butanol 30 ml. each time for 5 times; combining the extracts; mixing the combination from step (VIII) with analytical pure water saturated n-butanol to a constant volume of 200 ml in a measuring flask to obtain solution B; distilling to dry 50 ml solution B on a water bath; dissolving the residue with chromatographically pure methanol to a constant volume of 25 ml in a measuring flask; and accurately sucking 5 ml. of the 25 ml. solution from step (IX); mixing it with chromatographically pure methanol to a constant volume of 25 ml; filtrating the diluted solution with 0.45 µm. filtration membrane to obtain sample solution II. b) using methanol solution of paeoniflorin (18.0 µg/ml) and methanol solution of paeonol (6.0 µg/ml) obtained from steps (II) and (IV) as the standard solutions; and c) performing PLC assay under following conditions: spectrum column: ALLtech-426 $C_{18}$ 5 µm., 4.6×250 mm; detector: ALLtech UVIS-201; pump: ALLtech-426 HPLC pump; injection valve: 7725i with 10 µl volume; column temperature: room temperature; flow rate 1 ml/min; injection volume: 10 µl; detective wavelength: 230 nm (paeoniflorin) and 274 (paeonol); mobile phase: methanol-water 35:65 (paeoniflorin) 60:40 (paeonol); and number of theoretical plates: based on peak of paeoniflorin, the number of theoretical plates should be no less than 5000; base on peak of paeonol, the number of theoretical plates should be no less than 1500. d) performing HPLC assay with following steps: injecting 10 µl. sample solution I (for paeonol) or sample solution II (for paeoniflorin) into HPLC to perform chromatography under given circumstance; and measuring area of the peaks to calculate the relative components of paeoniflorin and paeonol in the *Cinnamomi* and *Poria* composition.

In an embodiment, paeoniflorin is used as the standard to determine the amount of paeoniflorin in a *Cinnamomi* and *Poria* composition.

In separate embodiment, paeonol is used as the standard to determine the amount of paeonol in a *Cinnamomi* and *Poria* composition.

This invention also provides a pharmaceutical composition comprising an effective amount of the composition above and a pharmaceutically acceptable carrier.

In an embodiment, the above formulation is a pill, capsule, granule, tablet, suspension, injection, syrup, or tincture.

In an embodiment, the invention provides a method for relaxing the smooth muscles of excessively contracting uterine in a subject by directly inhibiting the contraction frequency, range and overall activity of the smooth muscles of uterine comprising administering to the subject an effective amount of the pharmaceutical composition above. In another embodiment, this invention provides a method for reducing the whole blood viscosity in a subject by inhibiting the agglutination of the blood platelet and inhibiting the release of blood platelet comprising administering to the subject an effective amount of the pharmaceutical composition above.

In yet another embodiment, the invention provides a method for regulating inflammatory functions in a subject by inhibiting the inflammatory reactions of various kinds comprising administering to the subject an effective amount of the pharmaceutical composition above. In still another embodiment, the invention provides a method for inducing a analgesic effects onto pains of various kinds in a subject comprising administering to the subject an effective amount of the pharmaceutical composition above. In still another embodiment, the invention provides a method for treating primary and secondary dysmenorrhea of various kinds of degrees in a subject comprising administering to the subject an effective amount of the pharmaceutical composition above. In another embodiment, this invention provides a method for alleviating clinical symptoms in a subject suffering from primary and secondary dysmenorrhea of various kinds comprising administering to the subject an effective amount of the pharmaceutical composition above.

In another embodiment, the invention provides a method for treating dysfunctional uterine bleeding caused by irregular shedding of uterine endometrium in a subject comprising administering to the subject an effective amount of the pharmaceutical composition above.

In yet another embodiment, the invention provides a method for alleviating clinical symptoms in a subject suffering from dysfunctional uterine bleeding caused by irregular shedding of uterine endometrium comprising administering to the subject an effective amount of the pharmaceutical composition above. In still another embodiment, the invention provides a method for treating chronic pelvic inflammations and inflammatory lower abdomen masses in a subject comprising administering to the subject an effective amount of the pharmaceutical composition above.

In a further embodiment, the invention provides a method for alleviating clinical symptoms in a subject suffering from chronic pelvic inflammations and inflammatory lower abdomen masses comprising administering to the subject an effective amount of the pharmaceutical composition above.

In still another embodiment, this invention provides a method for treating small intramural hysteromyoma in a subject comprising administering to the subject an effective amount of the pharmaceutical composition above. In yet another embodiment, the invention provides a method for alleviating clinical symptoms in a subject suffering from small intramural hysteromyoma comprising administering to the subject an effective amount of the pharmaceutical composition above.

In a further embodiment, the invention provides a method for alleviating the symptoms of Profuse or prolonged menstruation, excess of blood clots during menstrual period, vague pain, distending pain at lower abdomen and lower lumber, large amount of leulorrhea, heavy and distending anus or anemia in a subject suffering from dysfunctional uterine bleeding, primary and secondary dysmenorrhea, chronic pelvic inflammations, inflammatory lower abdomen masses or small intramural hysteromyoma comprising administering to the subject an effective amount of the pharmaceutical composition above.

In another embodiment, the invention provides a method for improving abnormal indexes in blood rheology in a subject comprising administering to the subject an effective amount of the pharmaceutical composition above. In another embodiment, the invention provides a method for decreasing dim purpuric spots in tongue in a subject comprising administering to the subject an effective amount of the pharmaceutical composition above.

In another embodiment, the invention provides a method for improving faint wrist pulse in a subject comprising administering to the subject an effective amount of the pharmaceutical composition above.

Furthermore, this invention provides a pharmaceutical composition for treating gynecological blood stasis, cardio-cerebral vascular diseases, respiratory system and urinary system diseases comprising the following materials in weight proportion: Ramulus Cinnamomi, 1-2 portion; Poria Cortex, 1-2 portion; Moutan Radicis, 1-2 portion; Radix Paeonize Alba, 1-2 portion; and Semen Persicae, 1-2 portion.

This invention also provides a method for obtaining a composition comprising: distilling a required amount of Cortex Moutan with water through a process of hot reflux and collecting its distillate, filtering and drying said distillate after its cooling down to obtain crude Paeonol; mixing the residues with required amount of Ramulus Cinnamomi, Radix Paeonize Alba, Semen Persicae and 50% of Poria Cortex, adding alcohol to the mixture and extract, extracting the mixture, filtering the extract to obtain an alcohol extract; adding water to residue from the alcohol extraction, extracting and filtering it to obtain a water extract; Mixing the alcohol extract, water extract and solution from distilling of Cortex Moutan, enriching the mixture to a creamed extract; and granulating the rest 50% of Poria Cortex into fine powder, mixing the fine powder with the creamed extract, granulating the mixture after vacuum drying, mixing the granule with crude Paeonol; and filling the mixture in to capsules to form the product.

In an embodiment, the composition is featured as 3 times weight of 90% alcohol for the alcohol added in the mixture and 4 times weight of water for the water added in the mixture. In another embodiment, the alcohol extraction is 2 hours each time and the water extraction is 2 hours each time.

In a further embodiment, this invention provides a composition comprising the product produced by the method above for treating diseases of gynecological blood stasis.

In yet another embodiment, the method of producing drug for treating diseases of gynecological blood stasis is the method of producing drug for treating hysteromyoma. In another embodiment, the method of producing drug for treating diseases of gynecological blood stasis is the method of producing drug for treating pelvic inflammations. In yet another embodiment, the method of producing drug for treating diseases of gynecological blood stasis is the method of producing drug for treating dysmenorrhea. In a further embodiment, the method of producing drug for treating diseases of gynecological blood stasis is the method of producing drug for treating irregular menstruation. In a further embodiment, the method of producing drug for treating diseases of gynecological blood stasis is the method of producing drug for treating bleeding diseases of women.

The invention also provides the composition comprising the product produced by the method above for treating diseases of cardio-cerebral vascular diseases. In an embodiment, the method of producing drug for treating cardio-cerebral vascular diseases is the method of producing drug for treating hypertension. In another embodiment, the method of producing drug for treating cardio-cerebral vascular diseases is the method of producing drug for treating heart diseases.

This invention also provides the product produced by the method above for treating diseases of respiratory system diseases. The invention still further provides the composition comprising the product produced by the method above for treating diseases of urinary system diseases.

This invention provides a composition comprising 1.3-1.9% cinnamaldehyde.

This invention provides a composition comprising 0.7-1.1% paeoniflorin.

This invention provide a composition that when the volatile matter of the composition subjected to Gas Chromatography (GC) the 7 peak fingerprint shown in FIG. 1 and tabulated in Table 2 is produced. In this fingerprint the retention time (RT) ratios of the 7 peaks in comparison with cinnamaldehyde are 0.757, 1.275, 1.290, 1.449, 1.704, 2.146 and 3.061 respectively; the area ratios of peak 1 and peaks 3-7 in comparison with cinnamaldehyde are 1.183, 0.696, 5.565, 0.093, 0.164, 0.115 respectively; and the range of the retention time ratios of the 7 peaks in comparison with cinnamaldehyde are 0.770-0.745, 1.280-1.270, 1.295-1.285, 1.455-1.440, 1.710-1.700, 2.150-2.140 and 3.070-3.055 respectively; and the range of the area ratios of peak 1 and peaks 3-7 in comparison with cinnamaldehyde are 1.740-0.690, 1.110-0.350, 8.080-3.460, 0.140-0.060, 0.255-0.080 and 0.160-0.070 respectively.

This invention provide a composition that when the Water-soluble matter of the composition subjected to High Performance Liquid Chromatography (HPLC) the 13 peak fingerprint shown in FIG. 2 and tabulated in Table 3 is produced. In this fingerprint the retention time (RT) ratios of the 13 peaks in comparison with paeoniflorin are 0.261, 0.349, 0.584, 0.915, 1.076, 1.118, 1.162, 1.196, 1.268, 1.312, 1.420, 2.107 and 2.389 respectively; the area ratios of the 13 peaks in comparison with paeoniflorin are 0.645, 0.103, 0.128, 0.212, 0.089, 0.046, 0.052, 0.083, 0.076, 0.211, 0.404, 0.149 and 0.981 respectively; and the range of the retention time ratios of the 13 peaks in comparison with paeoniflorin are 0.275-0.250, 0.360-0.340, 0.600-0.560, 0.920-0.910, 1.085-1.070, 1.125-1.110, 1.175-1.155, 1.210-1.180, 1.285-1.250, 1.330-1.295, 1.450-1.400, 2.170-2.060 and 2.465-2.340 respectively; and the range of the area ratios of the 13 peaks in comparison with paeoniflorin are 0.750-0.460, 0.160-0.070, 0.230-0.065, 0.250-0.170, 0.130-0.065, 0.060-0.035, 0.080-0.030, 0.105-0.055, 0.090-0.065, 0.255-0.140, 0.470-0.310, 0.195-0.130 and 1.475-0.680 respectively.

This invention provide a composition that when the lipo-soluble matter of the composition subjected to High Performance Liquid Chromatography (HPLC) of 210 nm in detective wavelength the 7 peak fingerprint shown in FIG. 3 and tabulated in Table 4 is produced. In this fingerprint the retention time (RT) ratios of the 7 peaks in comparison with pachymic acid are 0.367, 0.408, 0.897, 0.980, 1.019, 1.143 and 1.305 respectively; the area ratios of the 7 peaks in comparison with pachymic acid are 0.322, 0.580, 0.280, 0.752, 0.286, 4.650 and 0.959 respectively; and the range of the retention time ratios of the -7 peaks in comparison with pachymic acid are 0.375-0.355, 0.420-0.395, 0.905-0.890, 0.985-0.975, 1.025-1.015, 1.150-1.135 and 1.315-1.295 respectively; and the range of the area ratios of the 7 peaks in comparison with pachymic acid are 0.540-0.180, 0.900-0.410, 0.350-0.220, 0.940-0.600, 0.410-0.210, 5.950-2.900 and 1.450-0.575 respectively.

This invention provide a composition that when the lipo-soluble matter of the composition subjected to High Performance Liquid Chromatography (HPLC) of 242 nm in detective wavelength the 8 peak fingerprint shown in FIG. 4 and tabulated in Table 5 is produced. In this fingerprint the retention time (RT) ratios of the 8 peaks in comparison with polyporenic acid C are 0.520, 0.566, 0.686, 1.128, 1.557, 1.763, 2.133 and 3.033 respectively; the area ratios of the 8 peaks in comparison with polyporenic acid C are 0.155, 0.184, 1.385, 0.481, 0.181, 1.414, 0.630 and 0.463 respectively; and the range of the retention time ratios of the 8 peaks in comparison with polyporenic acid C are 0.530-0.510, 0.570-0.560, 0.690-0.680, 1.135-1.125, 1.585-1.525, 1.800-1.720, 2.190-2.070 and 3.105-2.950 respectively; and the range of the area ratios of the 8 peaks in comparison with polyporenic acid C are 0.185-0.120, 0.230-0.140, 1.950-0.900, 0.530-0.430, 0.240-0.150, 1.700-1.250, 0.840-0.480, 0.680-0.160 respectively.

This invention provides the above compositions having components extracted from Ramulus Cinnamomi, *Poria*, Cortex Moutan, Radix Paeoniae Alba and Semen Persicae.

This invention provides the above compositions having components extracted from Ramulus Cinnamomi, *Poria*, Cortex Moutan, Radix Paeonia Alba and Semen Persicae that are obtained from cultivated plants.

Capsule of *Cinnamomi & Poria* (CCP)

The product is produced in capsule form. Its interior is yellowish brown granule, witch is fragrant and tasted slightly bitter. Each capsule contains 0.31 g. of the granule, which can be stored for 18 month in room temperature.

CCP is used for primary or secondary dysmenorrhea, dysfunctional uterine bleeding caused by irreglar shedding of endometrim, chronic pelvic inflammations with inflammatory lower abdomen masses or small intramural hysteromyoma, and many common pelvic disorders.

CCP is for oral administration, 3 capsules each time, 3 times a day, preferably after meals. The users are advised not to use this product during a menstruation period. Period of treatment course is three months or follow directions of a physician.

CCP was source from Bolus of *Cinnamomi & Poria*. The inventors started developing it in 1989, and had been granted the Certificate of New Medicine and Certificate of production by authorities in China. (1995, Health Dept approval No.Z-25; Health Dept Medical Standard 1998; WS2-097[X-017]-98[z])

| Formula of the raw medicinal materials | |
|---|---|
| Ramulus Cinnamomi | 144 k.g. |
| Poria Cortex | 144 k.g. |
| Moutan Radicis | 144 k.g. |
| Radix Paeonize Alba | 144 k.g. |
| Semen Persicae | 144 k.g. |

(For 600,000 capsules)

Detailed Process

Wash Ramulus Cinnamomi, Moutan Radicis, Radix Paeonize Alba and Semen Persicae in high-pressure water after picking out impurities. Fumigating sterilize the four medicinal materials with Epoxyethane. Smash Ramulus Cinnamomi, Semen Persicae and Moutan Radicis into coarse powders and chop Radix Paeonize Alba into slice of 2-3 mm Microwaves sterilize the Poria Cortex. Granulate 50% of Poria Cortex of the formula weight into fine powder (70-72 k.g. for the formula of total raw materials of 720 k.g.). Filter the powder with a 100 meshes sift.

Soak full amount of Cortex Moutan (144 k.g.) in water for four hours before distilling it in water and collecting its distillate. After cooling down of the distillate, filtering and vacuum drying it at below 55° C. 1.6-1.8 k.g. crude Paeonol is obtained from the distillate. The concentration of crude paeonol should be no less than 80%. The residue and fluid from the above procedure is reserved for future use; Weight 10.2 k.g. of β-cyclodextrin to prepare its saturated water solution at 80° C. Dissolve full amount of above-mentioned crude paeonol into 9.0 k.g. of 95% alcohol. Slowly add the alcoholic solution into the β-cyclodextrin water solution while keep agitating the mixture at thermostatic 80° C. Keep agitating the mixture at thermostatic 80° C. for another 3 hours and stored it for 24 hours in a refrigerator before it is exhausted filtering. The residue is then washed by small amount of anhydrous alcohol and let dried in the room temperature. About 9.86 k.g. of clathrate of white powder is obtained from this step.

Soak full amount of Cortex Moutan (144 k.g.) in water for six hours. Distill Ramulus Cinnamomi in water for four hours and collecting its volatile matter. (presence of cinnamaldegyde is tested here in the volatile matter). 0.82-0.93 liter of volatile oil is obtained from this step. The residue and fluid is reserved for future use; Weight 3.72 k.g. of β-cyclodextrin to prepare its saturated water solution at 45° C. Dissolve full amount of above-mentioned *cinnamomi* volatile oil into 5.0 k.g. of 95% alcohol. Slowly add the alcoholic solution into the β-cyclodextrin water solution while keep agitating the mixing solution at thermostatic of 45° C. Keep agitating it at thermostatic 45° C. for another 3 hours and stored 24 hours in a refrigerator before exhausted filtered. The residue is then washed by small amount of petroleum ether and let dry in the room temperature. About 3.70 k.g. of white powder clathrate is obtained.

The residue of Cortex Moutan and Ramulus Cinnamomi from the above-mentioned steps are mixed with full amount of Radix Paeonize Alba (144 kg), Semen Persicae (144 kg), the rest 50% of Poria Cortex (72 kg) and three times weight of 90% alcohol. Extract the mixture twice for two hours each, filter the extract and reserve the alcohol extract after recovery of the alcohol from it. Add four times weight of water to its residue, distill it twice for two hours each time and filter the water extract. The water extract, alcohol extract, fluid of Cortex Moutan and fluid of Ramulus Cinnamomi from the above-mentioned steps are joined together and were enriched in vacuum at temperature below 55° C. About 110-130 k.g. of a creamed extractive with a relative density of no less than 1.27 (75-80° C.) is obtained.

Thoroughly mix the creamed extractive with the granulated Poria Cortex powder and grind it into fine powder after a vacuum drying procedure at under 55° C. About 164 k.g. of a powder is obtained.

Thoroughly mix 8.2 k.g. of starch gum with the fine powder. Granulate the mixed powder to 30 meshes with some 60% alcohol. After vacuum drying process at a temperature under 55° C. and rectifying procedure, a total 171-172 k.g. of granule is obtained.

Thoroughly mix the β-cyclodextrin clathrate of Paeonol, β-cyclodextrin clathrate of *Cinnamomi* volatile oil and 0.33 k.g. of silicon dioxide in a high performance mixer. 13.8 k.g. of mixture is obtained.

Thoroughly mix the 13.8 k.g. of mixture with the above-mentioned granule, rectify the granule. 186 k.g. of intermediate granule is produced. Mass balance of all above-processed materials should be ±5%.

Technical Requirements (1) The *Poria* fine powder needs to be screened by 100 meshes of screen (inner diameter 150±6.6 μm.)

(2) the concentration of crude paeonol should be no less than 80%;

(3) Concentration and drying must be performed under vacuumed conditions. The temperature can't be above 55° C.

(4) The volatile matter is tested for the presence of cinnamaldegyde.

(5) Material mass balance should be +5%.

Medicinal Materials and their Processing

Ramulus Cinnamomi (Common Name: Cassia Twig)

Cassia Twig is the dried young stem of *Cinnamomum cassia* Presl (Fam. Lauraceae). The plant is collected in spring or summer. It is dried in the sun after collection, removal of its leaves and perhaps chopped into slides.

The medicinal preparation has cylindrical body, multi-branched, 30-75 cm in length, its thick end is 0.3-1 cm in diameter. It is brown or reddish-brown on the surface, with longitudinal lines, fine wrinkles, dotted with leaf, branch or bud scars, lenticels dotted or dotted elliptic. Hard and fragile, it is easily broken. For the slices, it is 2-4 mm thick, cut surface showing reddish-brown in bark, yellowish-white to pale yellowish-brown in the wood part, pith subsquare. Odor characteristic aromatic; taste, sweet and slightly pungent, especially in bark. The medicinal preparation is the clean scraps of *Cinnamomi* without visible impurities. The important ingredients of *Cinnamomi* is cinnamaldehyde and cinnamic acid.

Provider: Tianma Medicinal Material Company in Bozhou, Anhui P.R.C. Attn: ZHOU, Fang Mobile: 011-86-1360-5682-623

Poria Cortex (Common Name: Indian Bread)

*Poria* is the dried sclerotium of the fungus, *Poria cocos* (Schw.) Wolf (Fam. Polyporaceae). The plant is collected from July to September. After collection, it was piled up and spread about for air-drying repeatedly until wrinkles appears on the surface and its inner moisture evaporated. The whole dried sclerotium is known as "Fulingge". If the fresh sclerotium is peeled before drying. The separated parts are called "Fulingpi" (peel) and "Fulingkuai" (flesh).

Fulingge Subglobose, ellipsoid, oblate or irregular shaped, variable in size. The outer skin thin and rough, brown to blackish brown, conspicuously shrivelled and striated. Texture hard and compact, fracture granular, some cracked, the outer layer pale brown, inner part white, rarely reddish, some showing the penetrating roots of pine in the centre. Odourless; taste, weak and sticky when chewed. The medicinal preparation is the clean scraps of *Poria* without visible impurities. Its important active ingredients are Pachman and Pachymic acid.

Provider: Shuanggou Medicine Company in Bozhou, Anhui P.R.C. Attn: HUANG, Jigang Telephone: 011-86-558-5116-893, Mobile: 011-86-1380-5689-093.

Cortex Moutan (Common Name: Tree Peony Bark)

Tree Peony Bark is the dried root bark of *Paeonia suffruticosa* Andr. (Fam. Ranunculaceae). The root is collected in autumn, removed from rootlets, the root bark is stripped off, and dried in the sun.

Quilled or semiquilled, longitudinally fissured, somewhat involute or opened, 5-20 cm long, 5-12 mm in diameter, 1-4 mm thick. The outer surface greyish-brown or yellowish-brown, showing numerous transverse lenticels and rootlet scars, the exposed layer where cork fallen off appearing pink; the inner surface greyish-yellow or brownish, with obvious fine longitudinal striations, usually showing bright crystals. Texture hard and fragile, easily broken, fracture relatively even, starchy, pale pink. Odour, aromatic; taste, slightly bitter and astringent. The medicinal preparation should be the clean Moutan Radicis without visible impurities. The important ingredients: Paeonol.

Provider: Nature Medicinal Herbs Company in Bozhou, Anhui P.R.C. Attn: ZHOU, Wenxin Telephone: 011-86-562-6811-050.

Radix Paeoniae Alba (Common Name: White Peony Root)

White Peony Root is the dried root of *Paeonia lactiflora* Pall. (Fam. Ranunculaceae). The drug is collected in summer and autumn, washed in water, remove the root stock and the lower part and rootlet, boiled in water, peeled, and dried in the sun.

Cylindrical, straight or slightly curved, two ends truncate, 5 18 cm long, 1-2.5 cm in diameter. Externally whitish or pale reddish brown, glossy or with longitudinal wrinkles, rootlet scars and occasional remains of brown cork. Texture compact, easily broken, fracture relatively even, whitish or pale brownish-red, cambium ring distinct and rays radial. Odour, slight; taste, slightly bitter and sour. Medicinal used Radix Paeonize Alba should be the clean scraps of Radix Paeonize without visible impurities. Its important active ingredient is paeoniflorin.

Provider: National Medicinal Herb Company in Bozhou, Anhui P.R.C. Attn: ZHOU, Hai Mobile phone: 011-86-1370-5680-735.

Semen Persicae (Common Name: Peach Seed)

Peach Seed is the dried ripe seed of *Prunus persica* (L.) Batsch or *Prunus davidiana* (Carr.) Franch. (Fam. Rosaceae). The fruit is collected when ripe. The seed is removed from sarcocarp and shell (endocarp), and dried in the sun.

Seed of *Prunus Persica* Prolate-ovate, 1.2-1.8 cm long, 0.8 1.2 cm wide, 0.2-0.4 cm thick. Externally yellowish-brown to reddish brown, with numerous granular protrudings. One end acute, expanded in the middle, the other end obtuse-rounded and slightly oblique with relatively thin edge. A short linear hilum occurring by the acute end and a relatively distinct and slightly dark chalaza at the round end, with many longitudinal vascular bundles radiated from the chalaza. Testa thin, cotyledons 2, almost white and oily. Odor weak; taste, slightly bitter. The medicinal preparations should be a pure Semen Persicae in powder form, clean and without impurities. Its important active ingredient is amygdalin.

Provider: Xingsheng Medicinal Herbs Company in Bozhou, Anhui P.R.C. Attn: L I, Yulong Telephone: 011-86-558-5525-258 Mobile: 011-86-1395-6716-718.

Quality Control of Semi-Products

Creamed extractive: creamed extractive is dark brown in color. Its relative density should be no less than 1.27 (at 75~80° C.), content of paeoniflorin should be 1.8~2.7%

Soft powder after the mixing of Poria cortex: a yellowish brown in coloring with a slightly bitter taste. The microbe limit: number of bacteria can't exceed 5000 entries/g; fungus can't exceed 300 entries/g; living acarid, acarid egg or coliform should not be detected. Content of paeoniflorin: 1.4~2.2%.

Final granules: yellowish brown with water content no more than 4.0%

Capsules: clean, not sticky or mutilated in shape. Difference of content: no more than 8.0% (0.31 g/capsule). Dissolving time is within 25 minutes. Water content no more than 4.0%. Content of paeoniflorin is at 1.3~1.9% and paeonol 0.7~1.1%.

| Yield rate of semi-products | |
| --- | --- |
| Poria powder | 92~98% |
| Soft material powder | 94~98% |
| Extract | 15~18% |
| Granule | 96~98% |

Preparation of compound Chinese Traditional Medicine result in a sophisticated physical and chemical procedures that involves tons of complex compounds. During the decocting process, there always resulting in new ingredients. Base on properties of different medicine materials in TCM and procedures of CCP, we have summarized general characteristic of various ingredients in CCP and charted them in the table below.

| Components | Content (%) |
|---|---|
| β-Pachyman | 32-36 |
| Amygdalin | 1.3 |
| Amylum | 30-34 |
| Amino acid | 0.5 |
| Salicylic acid | 0.1 |
| Dextrin | 10-12 |
| $SiO_2$ | 0.5 |
| $H_2O$ | 4 |
| Colophony, shell Protein and fat | 4-6 |
| Tannin, β-cytellin Phlegm and glycose | 10-14 |
| Paeoniflorin* | 1.3-1.9 |
| Paeonol* | 0.7-1.1 |

*primary active component

Subsidiary Components

Silicon Dioxide

Other names: Silicon Dioxide; White Carbon; Silica Gel;- Precipitated silica; Colloidal Silicon Dioxide.

Molecular formula and weight: $SiO_2 \cdot nH_2O$; 60.80(anhydrous)

Preparative method: sodium silicate reacts with hydrochloric acid, nitric acid or vitriol to obtain silica gel which is aquiferous after depositing, washing, and drying. In air that is evenly mixed with hydrogen gas, silicon chloride hydrolyzes in water after burning under high temperature, and a solid aerosol is formed. Then use circulating separator to create anhydrous silica gel.

Properties: Due to differences in preparation methods, the product's physical & chemical characteristics vary. It is in white powder form and insipid. With its hygroscopic feature, it does not resolve in water, organic solvent, or acid (except hydrofluoric acid). It does resolve in hot sodium hydroxide.

Usage: the product comes in tablet and capsule forms. It is used as a dilutent, a supplement, an anti-adherent agent in preparation of tablets or capsules; suspendsoid of ointment & suppository; stabilizer of emulsion; absorbent of liquid components in solid preparation. Precipitable silica gel can also be used as a clarifying agent. Colloid silicon dioxide can be used as the carrier of adsorbent solid dispersoid of organic substance with hydroxyl.

Stability and storage conditions: this product is hygroscopic, therefore it should be stored in a container and put in a dry environment.

Dextrin

Molecular formula & weight: $(C_6H_{10}O_5)n \cdot xH_2O$ (162.14). Molecular weight is represented by n; average value is 4500.

Properties: this product is colored white and it's in powder or granule form with a special fragrance and a sweet taste. Its bulk density is 0.80; real density is 0.918; melting point is 178 (dissolved); water content is 5%; area of specific surface is 0.14 m²/g (quantasorb). It is easily dissolved in hot water, and transforms into a clear colloidal solution. It is also dissolvable in cold water, ethanol solution, or propanol solution.

Usage: this product can be used as an absorbent, a dilutent, or a bonding agent.

Properties of some Important Ingredients

Paeonol

Chemical Name: Ethanone, 1-(2-hydroxy-4-methoxyphenyl)-Molecular formula: $C_9H_{10}O_3$; Molecular weight: 166.17

Source: Cortex of *Paeonia moutan* Sim, family Ranunculaceae, herb of *Pycnostelma paniculatum* (Bunge) K. Schum, family Asclepiadaceae, bark of *Brtula platyphylla* Suk. Var *japonica* (Sieb.) Hara, herb of *Primula auricula* L, root of *Rithysa meridionalis* L.B. Smith & Downs.

Physical properties: colorless acerate crystal (ethanol), melting point is 50° C., resolve a little in water, may be volatilized along with vapor, resolve ethanol, ether, acetme, chloroform, benzene and carbon disulfide.

$Uv\lambda_{max}^{EtOH}$ nm (log ε): 291(4.61), 274(4.17), 316(3.84)

$Irv_{max}^{KBr}$ cm$^{-1}$: 2940 & 1639(strong). NMR ($CDCL_3$: 2.55 (3H,S), 3.8(3H,S), 6.3~6.6(2H,m), 7.6(1H,d,J=9), 10.6 (1H,s). MSm/e (%): 166(M+, 42), 151(100), 108(8), 95(7), 43(8).

(TLC 1: silica gel G; Developer: cyclohexane-ethylester acetate (3:1); Coloration: 3% ferric chloride ethanol solution; Rf: 0.85 TCL 2: silica gel G; Developer: cyclohexane-chloroform-ethanol absolute (7:3:1); Coloration: 3% ferric chloride ethanol solution; Rf: 0.60)

Results of current studies on physiological activities:

1) On Central Nerves system: injected in a mouse or taken orally, and have abirritative, antalgic & hypnotic function. It can reduce the temperature and defervesce to a normal and calorifacient mouse, also it could withstand convulsion induced by electricity and medicines. 2) Antibacterial and antiphlogistic Function: controlling consistency to golden *staphylococcus* and *streptococcus faecalis* is 500 µg/ml; controlling consistency to coliform and *bacillus subtilis* is 200 µg/ml, controlling consistency to tinea germ between toes is 250 µg/ml. If taking orally, it can withstand inflammation that was induced by carrag cenin, glucosan and acetic acid. 3) Reducing Blood Pressure: anaesthetize dog and mainline 80-120 mg/kg, reduce pressure 41-61%, can keep 10-12 mins. It shows the obvious function of reducing pressure for most of the treated dogs and mouse with high blood pressure. 4) Toxicity: weak toxicity, mouse $LD_{50}$(mg/kg), mainline 196, celiac injection 741, take orally 3430 & 4900. 5) Clinic use: inject 50~100 mg in muscle or certain points each time. It shows good curative effect to treat rheumatism, stomachache, other pains, eczema and irritability dermatitis etc., and the validity rate is 83%. Its validity rate is 92% to 261 cases with rheumatoid arthritis, lumbago, stomachache, bellyache, postoperative & cancer pain.

Paeoniflorin

Chemical Name: β-D-Glucopyranoside, 5b-[(benzoyloxy)]tetrahydro-5-dydroxy-2-methyl-1,5-methano-1H-3,4-dioxacyclobuta[cd]pentalen-1a (2H)-yl [1aR-(1aα, 2β, 3aα, 5α, 5aα, 5bα)]-Molecular formula: $C_{23}H_{28}O_{11}$; Molecular weight: 480.45

Source: root of *Paeonia albiflora* Pall. (*P. Lactiflora* Pall.), root of *P. Suffruticosa* Andr. (P.moutan Sims), root of *P. Delavayi* Franch.

Physical Properties: hygroscopic, formless powder, $[\alpha]_D^{16}$-12.8°(C=4.6, methanol), colorless & acerate crystal, the melting point is at 196° C.

$UV\lambda_{max}^{EtOH}$ nm(ε):230(9560).$IRv_{max}^{nujol}$ cm$^{-1}$: 3400 (br.),1708, 1604, 1585, 1270.

Results of current studies on physiological activities:

1) Function to Cordis Vessel: dilate coronary artery, the effect will increase the flow of coronary artery, withstand acute lack blood of cardiac muscle, control coacervation of blood platelet, reduce the blood pressure etc, it has been tested out for treatment on coronary heart disease. 2) Ease pain and calmness: it has obvious antalgic effect to a injected celiacly mouse, can prolong the mouse's sleep time induced by, and can antagonize the convulsion induced by. 3) Antiinflaming and anticankerous function: can control ankle swelling induced by intradx, can prevent irritability ulceration, and restrain exudation of gastric juice. 4) Antifebrile function: can reduce the normal animal heat of mouse, can allay the animal heat of mouse creating fevered artificially. 5) Antispastic function: can restrain the movement of exosomatic intestines and endosomatic stomach of big rat & guinea pig, and urine smooth muscle of mouse. Can antagonize urine constriction of mouse induced by alpha-hypophamine. 6) Toxicity: low toxicity, LD50(mg/kg) of mouse: 3530(mainline), 9530(celiac injection).

Cinnamic Acid

Chemical Name: 2-Propenoic acid, 3-phenyl—

Molecular formula & weight: $C_9H_8O_2$; 148.16

Botanic source: Bark of *Cinnamomum cassia* Presl family Lauraceae, velamen of Lycium Chinese Mill, leaves of *Foeniculum vulgare* Mill, family Umbelliferae, colophony of *Myroxylon pereir*(Royle) *Klotzscli*, family Leguminosae.

Physical properties: (convert) melting point 132~134° C., $UV\lambda_{max}^{EtOH}$ nm: 268, MS m/e 148(M+, basal peal). Melting point 135~136° C., Boiling point 300° C.;

$UV\lambda_{max}^{EtOH}$ nm($\epsilon$): 273(20893), 222 (14125), 216(17783);

Irvhd max$^{KBr}$ cm$^{-1}$: 2520, 1690, 1680, 1640, 1590, 1500, 1460, 1430, 1350, 1320, 1290, 1240, 1210, 1180, 1070, 980, 940, 870, 770, 710, 590, 540, 480, MS m/e(%): 147(100), 748(94), 103(63), 77(50), 51(50), 102(44), 131(31), 91(25)[2].

Results of current studies on physiological activities:

Antibacterialm and antifungal function, use as antiseptic. Be used to treat tuberculosis clinically, can increase leukocyte. In recent years, the animal testing proves that the function can increase leukocyte. Inject 1.5 mg/kg natrium cinnamate hypodermically to every rabbit, and keep 3 days, increase 200~250% leukocytes; keep over 10 days, has no influence to weight & temperature of animal. Has cholagogue function to dogs; has slightly lax function.

Amygdalin

Other Names: Mandelonitrile-β-gentiobioside, Amygdaloside, laetrile, VB-17.

Chemical Names: Benzeneacetonitrile, α-[(6-O-β-D-glucopyranosyl-β-D-glucopyranosyl)oxy]-, (R)—

Molecular Formula and Weight: $C_{20}H_{27}NO_{11}$; 457.42

Source: the seed of *Prunus persica* (.)Batsch. seed of *P.amygdalus* Batsch. seed of *P. armeniaca* L. seed of *P.salicina* Lindl. Kernel of *P.mume*(Sieb.)Sieb.et Zucc. branch of *taegus oxyacantha* Linn and *Sorbus tianschanica* Rupr. seed of *Eriobotrya japonica* (Thunb.) Lindl, fruit of *Cydonia oblonga* Mill.

Physical Properties: The trihydrate is rhombic crystal (water), 200° C. melting point, melting point of anhydrous thing is about 220° C., $[\alpha]_D^{16}$-42° C. 1 g resolve in 12 ml water, 900 ml ethanol and 11 ml boiling ethanol. It is easy to resolve in boiling water, hardly dissolve in ether. $UV\lambda_{max}^{Meon}$ nm($\epsilon$): 268(179), 262(255), 257(256), 251(198), 208(7210), $IRv_{max}$max cm$^{-1}$, 3330, 2860, 1640, 1590, 1490, 1450, 1270, 1160, 1060, 690[1].

Results of current studies on physiological activities:

It has been used for treatment on cancer since 1845. In recent years, it has been often reported overseas. There are different parlances about its function and mechanism. Some think that it has anticancer function since β-glycuronidase of cancer tissue act on 1-β-glycuronic acid, and bring deadly HCN. Many Japanese and American reports shows that it has obvious curative effect, but there are some contrary reports, and have cases which it resulted in death after taking. Therefore there is dispute to its anticancer value. At present time, America State Cancer Institute is treating clinically 200 cancer patients to which other remedies take no effect.

Pachyman

During the past 10 years, more studies have been reported, since the result showing obvious antitumor effects of Chtosan, Pachyman and Amorphalls mannan have brought on attention of researchers in the fields of organic chemistry, biochemistry, phytochemistry, physic and pharmacy.

Stability Test of CCP

Three batches of CCP (batch number: 960302, 960315, 960321) were tested of the stability at room temperature for 36 months. The following items were tested, among which the content of Paeonol was tested as an index of the chief ingredients: appearance (product should be brownish yellow granules, smells slightly herb aromatic and a little bitter in taste); identification of *Cinnamomi* and *Poria* (results showed as positive or negative); the amount of Paeonol (%, method of HPLC); water contents or weight lost after dried in the thermostat (%); Hygienical inspection (number of bacterial, fungi and acarid). The result is show in table 1

TABLE 1

Stability test of CCP (room temperature)

| Time | 0 months (1996.3) | | | 3 months (1996.6) | | |
| --- | --- | --- | --- | --- | --- | --- |
| Batch No. | 960302 | 960315 | 960321 | 960302 | 960315 | 960321 |
| Appearance | Brownish yellow granules, aromatic, slightly bitter | | | Brownish yellow granules, aromatic, slightly bitter | | |
| Cinnamomi | + | + | + | + | + | + |
| Poria | + | + | + | + | + | + |
| Disintegration (min) | 7 | 7 | 9 | 7 | 7 | 7 |
| Weight variation | Comply with specified quality requirements | | | Comply with specified quality requirements | | |
| Water cont. % | 5.1 | 5.4 | 4.8 | 5.1 | 5.4 | 4.8 |
| Bacteria/g | 20 | 30 | 20 | 30 | 30 | 20 |
| Fungi/g | 10 | 20 | 10 | 20 | 20 | 20 |
| Colibacillus | Not tested | | | Not tested | | |
| Acarid | Not tested | | | Negative | | |
| Paeonol (%) | 0.78 | 0.876 | 0.80 | 0.78 | 0.76 | 0.80 |
| Time | 6 months (1996.9) | | | 12 months (1997.9) | | |
| Batch No. | 960302 | 960315 | 960321 | 960302 | 960315 | 960321 |
| Appearance | Brownish yellow granules, aromatic, slightly bitter | | | Brownish yellow granules, aromatic, slightly bitter | | |
| Cinnamomi | + | + | + | + | + | + |
| Poria | + | + | + | + | + | + |

TABLE 1-continued

Stability test of CCP (room temperature)

| | | | | | | |
|---|---|---|---|---|---|---|
| Disintegration (min) | 8 | 8 | 9 | 9 | 7 | 8 |
| Weight variation | Comply with specified quality requirements | | | Comply with specified quality requirements | | |
| Water cont. % | 5.2 | 5.4 | 4.9 | 5.1 | 5.4 | 4.8 |
| Bacteria/g | 30 | 30 | 20 | 30 | 30 | 20 |
| Fungi/g | 20 | 20 | 20 | 20 | 20 | 20 |
| Colibacillus | | Not tested | | | Not tested | |
| Acarid | | Negative | | | Not tested | |
| Paeonol (%) | 0.78 | 0.76 | 0.80 | 0.77 | 0.76 | 0.81 |
| Time | 18 months (1997.9) | | | 24 months (1998.3) | | |
| Batch No. | 960302 | 960315 | 960321 | 960302 | 960315 | 960321 |
| Appearance | Brownish yellow granules, aromatic, slightly bitter | | | Brownish yellow granules, aromatic, slightly bitter | | |
| Cinnamomi | + | + | + | + | + | + |
| Poria | + | + | + | + | + | + |
| Disintegration (min) | 9 | 8 | 8 | 8 | 8 | 9 |
| Weight variation | Comply with specified quality requirements | | | Comply with specified quality requirements | | |
| Water cont. % | 5.1 | 5.4 | 4.8 | 5.2 | 5.5 | 4.9 |
| Bacteria/g | 30 | 30 | 20 | 30 | 30 | 20 |
| Fungi/g | 20 | 20 | 20 | 20 | 20 | 20 |
| Colibacillus | | Not tested | | | Not tested | |
| Acarid | | Negative | | | Negative | |
| Paeonol (%) | 0.78 | 0.75 | 0.79 | 0.77 | 0.76 | 0.80 |
| Time | 30 months (1998.9) | | | 36 months (1999.3) | | |
| Batch No. | 960302 | 960315 | 960321 | 960302 | 960315 | 960321 |
| Appearance | Brownish yellow granules, aromatic, slightly bitter | | | Brownish yellow granules, aromatic, slightly bitter | | |
| Cinnamomi | + | + | + | + | + | + |
| Poria | + | + | + | + | + | + |
| Disintegration (min) | 9 | 7 | 8 | 9 | 8 | 8 |
| Weight variation | Comply with specified quality requirements | | | Comply with specified quality requirements | | |
| Water cont. % | 5.2 | 5.5 | 4.9 | 5.2 | 5.5 | 4.9 |
| Bacteria/g | 30 | 30 | 30 | 30 | 30 | 20 |
| Fungi/g | 20 | 20 | 20 | 20 | 20 | 20 |
| Colibacillus | | Not tested | | | Not tested | |
| Acarid | | Not tested | | | Negative | |
| Paeonol (%) | 0.77 | 0.75 | 0.80 | 0.77 | 0.76 | 0.79 |

Fingerprinting of Capsule of *Cinnamomi* & *Poria*

1) Gas Chromatography of CCP's Volatile Matter

System Requirement: HP-5 5% phenyl methyl siloxane capillary columns (30.0 m×0.32 mm×0.25 um); columns temperature 80° C. (5 min) to 250° C. (10 min) rising at 3° C./min; carrier gas is nitrogen with flow rate 1.5 ml/min; FDI detector with hydrogen 40 ml/min, air 350 ml/min; makeup gas: nitrogen 30 ml/min; inlet system temperature 250° C.; split injection with 50:1 in split ratio and 2 μl. in volume; temperature of detector 280° C.; recording time 72 minutes.

Preparation of sample solution of volatile matter: Add 50 ml water and 30 ml ethyl ether to the content of 10 capsules of *Cinnamomi* and *Poria*. Extract the solution with reflex on a Water bath of 75° C. for 90 minutes and let it cool down. Extract the water layer of the solution with 20 ml ethyl ether for three times and merge all ethyl ether solutions together. Volatilize to dry up the ethyl ether solution on a water bath of 35° C. and, finally, add ethyl ether to make it 5 ml in volume.

Preparation of standard solution of cinnamaldehyde: Prepare ethyl ether solution of cinnamaldehyde that contains 0.5 mg/ml of cinnamaldehyde.

System adjustment assay: 1) Number of theoretical plates: under designed circumstance, inject 2 ul of Standard cinnamaldehyde solution into the Gas Chromatography. Base on calculation on cinnamaldehyde peak, the number of theoretical plates should be no less than 800,000. 2) System accuracy: Relative Standard Deviation (RSD) of the peak areas in five consecutive injections of 2 ul standard cinnamaldehyde solution should be no more than 3.0%.

TABLE 2

Peaks of volatile matter in CCP, Gas Chromatography;
Standard peak: cinnamaldehyde (self-comparison),
peak 4: paeonol (see FIG. 1 for GC of volatile matter)

| Peak Number | Retention Time/Area | Range of Retention Time | Range of Aria |
|---|---|---|---|
| 1 | 0.757/1.183 | 0.770~0.745 | 1.740~0.690 |
| Standard | 1/1 | | |
| 2 | 1.275 | 1.280~1.270 | |
| 3 | 1.290/0.696 | 1.295~1.285 | 1.110~0.350 |
| 4 | 1.449/5.565 | 1.455~1.440 | 8.080~3.460 |
| 5 | 1.704/0.093 | 1.710~1.700 | 0.140~0.060 |
| 6 | 2.146/0.164 | 2.150~2.140 | 0.255~0.080 |
| 7 | 3.061/0.115 | 3.070~3.055 | 0.160~0.070 |

2) HPLC of CCP's Water-soluble Matter

System Requirements: Spectrum column: Alltima $C_{18}$ 5 um, 7.5 mm×4.6 mm (guard column) and 250 nm×4.6 mm (spectrum column); column temperature 30° C.; flow rate 1 ml/min, detective wavelength 230 nm; injection volume 5 ul; recording time 70 minutes.

Flow phase: $CH_3CN$—$H_2O$—$H_3PO_4$
A  50:950:1
B  400:600:1

$$A \xrightarrow{70 \text{ min}} B$$

Preparation of sample solution of water-soluble matter: Add 200 ml water to the content of 3 capsules. Extract the solution with reflex for 30 minutes (after boiling) and let it cool down. Centrifuge the solution for 10 minutes and filtrate its supernatant with 0.45 um filter membrane to obtain the filtrate.

Preparation of standard paeoniflorin solution: Prepare methanol solution of paeoniflorin that contains 0.5 mg/ml of paeoniflorin.

System adjustment assay: 1) Number of theoretical plates: under designed circumstance, inject 2 ul of Standard paeoniflorin solution into the HPLC. Base on calculation on paeoniflorin peak, the number of theoretical plates should be no less than 250,000. 2) System accuracy: Relative Standard Deviation (RSD) of the peak areas in five consecutive injections of 1 ul standard paeoniflorin solution should be no more than 3.0%.

TABLE 3

Peaks of water-soluble matter, HPLC; Standard peak: paeoniflorin (self-comparison), peak 1: gallic acid, peak 4: albiflorin, peak 10: 1,2,3,4,6-penta-O-galloyl-β-D-glucose, peak 13: mostly paeonol (see FIG. 2 for HPLC of water-soluble matter)

| Peak Number | Retention Time/Area | Range of Retention Time | Range of Aria |
|---|---|---|---|
| 1 | 0.261/0.645 | 0.275~0.250 | 0.750~0.460 |
| 2 | 0.349/0.103 | 0.360~0.340 | 0.160~0.070 |
| 3 | 0.584/0.128 | 0.600~0.560 | 0.230~0.065 |
| 4 | 0.915/0.212 | 0.920~0.910 | 0.250~0.170 |
| Standard | 1/1 | | |
| 5 | 1.076/0.089 | 1.085~1.070 | 0.130~0.065 |
| 6 | 1.118/0.046 | 1.125~1.110 | 0.060~0.035 |
| 7 | 1.162/0.052 | 1.175~1.155 | 0.080~0.030 |
| 8 | 1.196/0.083 | 1.210~1.180 | 0.105~0.055 |
| 9 | 1.268/0.076 | 1.285~1.250 | 0.090~0.065 |
| 10 | 1.312/0.211 | 1.330~1.295 | 0.255~0.140 |
| 11 | 1.420/0.404 | 1.450~1.400 | 0.470~0.310 |
| 12 | 2.107/0.149 | 2.170~2.060 | 0.195~0.130 |
| 13 | 2.389/0.981 | 2.465~2.340 | 1.475~0.680 |

3) HPLC of CCP's Liposoluble Matter

System Requirements: Spectrum column: Alltima $C_{18}$ 5 um, 7.5 mm×4.6 mm (guard column) and 250 nm×4.6 mm (spectrum column); column temperature 50° C.; flow rate 1 ml/min, detective wavelength 210 nm and 242 nm; injection volume 5 ul; recording time 76 minutes.

Flow phase: $CH_3CN$—$H_2O$—$H_3PO_4$
A  600:400:1
B  950:50:1

$$A (25 \text{ min}) \xrightarrow{40 \text{ min}} B (11 \text{ min})$$

Preparation of sample solution of liposoluble matter: Use the precipitation deposit that obtained from after the centrifugal process in water-soluble solution preparation. Flush the deposit with water until it becomes colorless. Add 20 ml methanol to the deposit, extract the solution with reflex for 30 minutes (after boiling) and let it cool down. Centrifuge the solution for 10 minutes. Volatilize to dry up the methanol from the solution on a water bath of 75° C. And finally, add certain amount of methanol to make the solution to be at 2 ml in volume, filtrate it with 0.45 um filter membrane and obtain the filtrate.

Preparation of standard Poria raw material solution: Add 10 ml of methanol into 1 g. of Poria powder. Extract the solution with reflex for 30 minutes (after boiling) and let it cool down. After centrifugal, filtrate the supernatant with 0.45 um filter membrane and obtain the filtrate.

Standard Poria raw material is used in locating and identifying the two chemicals in liposoluble sample solutions: pachymic acid and polyporenic acid C at 210 and 242 nm respectfully. Pachymic acid and polyporenic acid C are chemicals within the samples and serve as standard peaks.

System Adjustment Assay: Same with HPLC of Water-Soluble Matter

TABLE 4

Peaks of liposoluble matter, HPLC 210 nm; Standard peak: pachymic acid (self-comparison), peak 1 contains dehydrorumulosic acid, peak 6 contains 3 β-hydroxylanosta-7,9 (11),24-trien-21-oic acid (see FIG. 3 for HPLC, 210 mn of liposoluble matter)

| Peak Number | Retention Time/Area | Range of Retention Time | Range of Aria |
|---|---|---|---|
| 1 | 0.367/0.322 | 0.375~0.355 | 0.540~0.180 |
| 2 | 0.408/0.580 | 0.420~0.395 | 0.900~0.410 |
| 3 | 0.897/0.280 | 0.905~0.890 | 0.350~0.220 |
| 4 | 0.980/0.752 | 0.985~0.975 | 0.940~0.600 |
| Standard | 1/1 | | |
| 5 | 1.019/0.286 | 1.025~1.015 | 0.410~0.210 |
| 6 | 1.143/4.650 | 1.150~1.135 | 5.950~2.900 |
| 7 | 1.305/0.959 | 1.315~4.295 | 1.450~0.575 |

TABLE 5

Peaks of liposoluble matter, HPLC 242 nm; Standard peak: polyporenic acid C (self-comparison), peak 3 contains dehydrotumulosic acid, peak 4 contains 3-epi-dehydrotumulosic acid, peak 6: dehydropachymic acid, peak 7 contains 3 β-hydroxylanosta-7,9(11),24-trien-21-oic acid (see FIG. 4 for HPLC, 242 mn of liposoluble matter)

| Peak Number | Retention Time/Area | Range of Retention Time | Range of Aria |
|---|---|---|---|
| 1 | 0.520/0.155 | 0.530~0.510 | 0.185~0.120 |
| 2 | 0.566/0.184 | 0.570~0.560 | 0.230~0.140 |
| 3 | 0.686/1.385 | 0.690~0.680 | 1.950~0.900 |
| Standard | 1/1 | | |
| 4 | 1.128/0.481 | 1.135~1.125 | 0.530~0.430 |
| 5 | 1.557/0.181 | 1.585~1.525 | 0.240~0.150 |

TABLE 5-continued

Peaks of liposoluble matter, HPLC 242 nm;
Standard peak: polyporenic acid C (self-comparison),
peak 3 contains dehydrotumulosic acid, peak 4
contains 3-epi-dehydrotumulosic acid, peak 6:
dehydropachymic acid, peak 7 contains 3 β-
hydroxylanosta-7,9(11),24-trien-21-oic acid (see
FIG. 4 for HPLC, 242 mn of liposoluble matter)

| Peak Number | Retention Time/Area | Range of Retention Time | Range of Aria |
|---|---|---|---|
| 6 | 1.763/1.414 | 1.800~1.720 | 1.700~1.250 |
| 7 | 2.133/0.630 | 2.190~2.070 | 0.840~0.480 |
| 8 | 3.033/0.463 | 3.105~2.950 | 0.680~0.160 |

Leading Pharmacodynamics Experiment about Remedial Effect of Capsule of *Cinnamomi & Poria* (CCP)

In order to determine the curative effects of the CCP, it is necessary to apply experimental research on animals. The research with animals showed that the CCP relaxes the smooth muscles, help reduce the blood viscosity, inhibit the agglutination of the blood platelet and it also has anti-inflammatory functions. Test on rats' extra-corporeal uterine contraction, and the analgesic effects on live rats etc, were done according to the leading pharmacodynamics research requirements for diseases of hypercoagulability established in the "New Chinese Traditional Medicine Research Directory", issued by the Drug Administration of Chinese Sanitation Bureau.

Capsule of *Cinnamomi & Poria* causes an inhibitory effect on the contraction of the smooth muscle of rats' extra-corporeal uterine. Using a 2.7 mg/ml extract of CCP, it is possible to gain 100% control of the contraction of the extra-corporeal uterine. Comparing the results to the control group with normal saline, a smaller amount of CCP (ointment formed extract 1.9 mg/ml, 1.3 mg/ml) can partly inhibit the smooth muscle contraction frequency ($P<0.05$), range ($P<0.05$) and its overall activity ($p<0.001, p<0.01$). The results showed there is a close dose-effect relationship between the concentration of CCP and the inhibitory effect.

Results also showed that a 5.4-mg/ml of CCP's extract might counteract the effect of alphahypophamine, which at the same time may increase the frequency of contraction of the extra-corporeal uterine of rats. Mice are administered the extract of CCP for 3 consecutive days. One hour after the capsule has been administered on the third day, inject acetic acid in abdomen. Observe the twisting times of mice, which is a reaction to pain. The results showed that 0.63 g/kg or 1.26-g/kg of CCP's extract can reduce the twisting times of mice, induced by showing a significant difference ($p<0.05$, $p<0.01$) when compared with the negative control group (normal saline) instead of CCP.

A high-dose of CCP (1.26 g/kg) resulted in a group's controlling rate of twisting times of mice similar to that obtained from the positive control group (aspirin group, 56.9% and 61.08% respectively). The high dose effect can also prolong the time mice swing their tales, which is also a reaction to pain. Such experiments of analgesia demonstrated that like aspirin, the CCP had a definite analgesic effect.

Mice are administered the drug for 5 consecutive days. Half an hour after the administration of the capsule on the fifth day, lightly anaesthetize the mice with ether, sample rats' blood from the abdominal aorta to determine the Whole Blood Ratio Viscosity. The results showed that by administering a 5.0 g/kg CCP, there is a decrease in the Whole Blood Ratio Viscosity. This explains the existence of a significant difference when these results are compared to those obtained from the normal saline control group (low shear $P<0.01$, high shear $P<0.05$). The Whole Blood Ratio Viscosity continued to decrease when the dose was increased. The results from the experiment demonstrated the effectiveness of the CCP when used to reduce the Whole Blood Ratio Viscosity of rats.

The results provided proof that a 12.5 mg/ml of CCP could reduce the conglomeration rate of blood platelet. There is a significant difference between these results and the ones obtained from the normal saline control group ($p<0.05$). The conglomeration rate of blood platelet decreased, as the dose was increased (CCP powder were 37.5 mg/ml and 75 mg/ml respectively).

The experiments of conglomeration of blood platelet indicated that a 10 g/kg extract of CCP reduced the conglomeration rate of blood platelet. The more the dose of CCP was increased, the stronger the effect. The results from the experiments about conglomeration of blood platelet also showed that the CCP could inhibit the increase rate of conglomeration of blood platelet induced by ADP.

Mice are administered the drug for three consecutive days. On the third day, smear an inflammatory inducing agent on the mice's right ear. The animals were killed two days after the smearing. The results indicated that the extract of CCP reduced the ear's swelling ($P<0.01$). Based on the results obtained in this experiment, it was proved that the CCP has a positive anti-inflammation effect. The research demonstrated that the CCP has acesodyne, antispastic and anti-inflammation effects. It could decrease the Whole Blood Viscosity, and inhibit the conglomeration of blood platelet.

Purpose of the Experiment

The CCP has the following effects: releases the smooth muscle contraction of rats' extra-corporeal uterine, acts against the enhanced smooth muscle contraction induced by oxytocin, reduces the twisting times of mice that was induced by acetic acid and prolongs mice's swinging tail time caused by temperature. The CCP reduces the Whole Blood Ratio Viscosity, and inhibits the conglomeration rate of extracorporeal blood platelet of rabbits.

The CCP has definite acesodyne, antispastic and anti-inflammatory effects. It also has the property to reduce Whole Blood Viscosity ratio, controls the conglomeration of blood platelet, and could be used for the treatment of dysmenorrhea in clinical practice.

Uterine Contraction

The CCP can activate blood circulation and eliminate stasis. It is mostly used to treat symptoms of dysmenorrhea and disorders from irregular shedding of endometrim, or many common pelvic disorders caused by smooth muscle movement or spasms in clinical practice in China. This research was done in order to establish the effects that the CCP has on uterine contraction and its possible curative effects.

Materials

Animal:

Female Wister rats with a weight of 180 g to 190 g. The rats were supplied by The Experimental Animals Centre of Nanjing Railway Medical Institute (Certificate No.97002, 97003). The rats had access to food, water and sunlight one whole week prior to the experiment.

Medicines:

Extract of CCP (1 g of CCP product corresponds to 4 g of the extract), Provided by Lianyungang Kanion Pharmaceutical Co. Ltd. (batch No.: 990515).

Dihydrotheelin (2 mg/ml), Batch No: 971103. Produced by Shanghai 9th Pharmaceutical Factory.

Oxytocin injection (10 u/ml), Batch No: 981228. Produced by Shanghai biochemistry Pharmaceutical Factory.

Pregnendione. Provided by Dr Swerdoiff of LAC-UCLA Medical Center.

Equipment:

JZ100 Muscle Tension Transducer produced by Nanbeidian City Xinhang Electro-mechanical Equipment Co. Ltd.

Yinhe 501 Type Superthermostat produced by Chongqing City Experimental Equipment Factory.

MS302 Physiological Information Processor provided by Pharmacology Staff Room of Guangzhou Pharmacy Institute.

The data collected for this experiment was stored on a Pentium II 300.

Methods

Preparation of Drug:

a) Put 5.4g extract of CCP in 100 ml of the Locke's solution and mixed thoroughly. The drug concentration results in 54 mg/ml. Take 1 ml of this solution, put it into a homothermic flume with 9 ml of the Locke's solution. The drug concentration from this mixture contains 5.4 mg/ml. Likewise, put 2.7 g extract of CCP in 100 ml of the Locke's solution and mixed thoroughly. Take 1 ml of this mixture, combine it with 9 ml of Locke's solution and the drug concentration will result in 2.7 mg/ml. Mix up 100 ml of the Locke's solution with a 1.9 g CCP's extract. Take 1 ml of this mixture, combine it with 9 ml of the Locke's solution and the drug concentration will result in 1.9 mg/ml. Mix 200 ml of the Locke's solution with 2.6 of CCP's extract, the concentration will result in 13 mg/ml. Take 1 ml of this mixture, combine it with 9 ml of the Locke's solution which results in a drug concentration of 1.3 mg/ml. Mix 200 ml or 300 ml of the Locke's solution with 1.8 CCP's resulting in a drug concentration of 9 mg/ml and 6 mg/ml respectively. Take 1 ml of this mixture into homothermic flume with 9 ml of the Locke's solution. The result is a drug concentration containing 0.9 mg/ml and 0.6 mg/ml respectively Preparation of Locke's Solution 9.0 of NaCL, 0.42 of KCL, 0.24 of $CaCL_2$, 0.2 of $NaHCO_3$ and 1.0 g of glucose. Mixed with distilled water until obtaining 1000 ml. PH is about 7.

Experiment Method

Twenty-four hours prior to the experiment, intramuscularly inject non-pregnant female rats with a 0.3 mg/kg weight-dose of Dihydrotheelin. The effect artificially puts them in estrus period so as to increase their sensitivity to the CCP. Decapitate the rats, rapidly paunch, take out the uterus and remove the fat. Cut the uterus in 2 cm of length and put it directly in the homothermic flume with 9 ml of the Locke's solution. One end of the uterus must be fixed on the crotchet of the L shaped ventilating pipe and the other end connected to the Muscle Tension Transducer. Keep the temperature of the homothermic flume at 32° C. Continuously emit oxygen into the fume, at least 60-80 bladders per minute and add in 1 ml of the previous solution with a different concentration. After recording a segment of normal contraction curve, observe the different phases before-and-after administering the drug. Respectively, record the contraction frequency and range. Observe from 1 to 10, 10 to 20, and 20 to 30 minutes before-and-after adding the drug solution. Count the uterine activity, and record data between control groups before-and-after administering the drug.

Observe CCP's effect in smooth muscle contraction of rats' extracorporeal uterine induced by oxytocin. Respectively, record the contraction frequency and range. Observe from 1 to 10, 10 to 20, and 20 to 30 minutes before-and-after adding the drug solution. Count the uterine activity and the inhibitory percentage. Record data as previously done.

Data processing

Activities = Frequency × Range

Percentage of Inhibition =

$$\frac{\text{Frequency before administering (or range, activities)} - \text{Frequency after administering (or range, activities)}}{\text{Frequency before administering (or range, activities)}} \times 100\%$$

All data is shown with the average value ± standard deviation (X±SD); All data between groups and within every group is examined using the t value in order to observe any significant difference.

Effect in Normal Rats' Uterine Smooth Muscle Contraction

Animals' Grouping: randomly divide the Wister female rats' extracorporeal uteruses into a normal saline control group (NSG) and a CCP group (CCPG). The dose of every group is respectively 2.7, 1.9, 1.3, 0.9 and 0.6 mg/ml of CCP extract.

Results: under stable conditions, extra-corporeal uteruses can keep active steadily within a period of 60 minutes. Under the 7 µg/ml concentration, the pregnendione can control contraction frequency of rats' uterine smooth muscle. Larger doses of extract of CCP (2.1, 1.9, 1.3 mg/ml) can control the contraction frequency (See tables 2 and 3), the range (See tables 4 and 5) and the activity (See tables 6 and 7) of rats' uterine smooth muscle in different degrees. A 2.7 mg/ml dose of CCP's extract can stop contraction of the uterine smooth muscle. The effect the drug produces in the uterine smooth muscle contraction can be noticed ten minutes after the drug has been administered. The control percentage can get to 100% (p<0.001).

TABLE 6

Influence of CCP's extract to contraction frequency in rats' extra-corporeal uterine smooth muscle (time/10 mins)

| Group | (X ± SD) | | | |
|---|---|---|---|---|
| | Before Adm. | After adm. 1-10 mins | After adm. 0-20 mins | After adm. 20-30 mins |
| NSG Progestin | 7.5 ± 1.0 | 8.1 ± 0.7 | 8.4 ± 1.7 | 7.8 ± 0.9 |
| 7 µg/ml CCP | 8.0 ± 0.8 | 6.1 ± 2.0 | 6.3 ± 2.5 | 5.0 ± 2.4* |
| 2.7 mg/ml | 7.4 ± 1.4 | 1.7 ± 1.5** | 0*** | 0*** |
| 1.9 mg/ml | 7.9 ± 2.7 | 5.0 ± 1.8 | 2.9 ± 3.9* | 2.7 ± 3.6* |

TABLE 6-continued

Influence of CCP's extract to contraction frequency in rats' extra-corporeal uterine smooth muscle (time/10 mins)

(X ± SD)

| Group | Before Adm. | After adm. 1-10 mins | After adm. 0-20 mins | After adm. 20-30 mins |
|---|---|---|---|---|
| 1.3 mg/ml | 8.2 ± 1.3 | 5.4 ± 1.4* | 4.2 ± 2.4* | 4.1 ± 3.0 |
| 0.9 mg/ml | 10.8 ± 2.9 | 7.8 ± 1.7 | 7.8 ± 2.4 | 7.6 ± 4.4 |
| 0.6 mg/ml | 8.3 ± 3.1 | 6.9 ± 2.3 | 8.3 ± 3.3 | 8.0 ± 3.9 |

*p < 0.05
**p < 0.01
***P < 0.001 (compare with itself before administering)

TABLE 7

Influence of CCP's extract on the contraction frequency in rats' extra-corporeal uterine smooth muscle (Controlling percenage %)

| Group | After adm. 1-10 mins | After adm. 10-20 mins | After adm. 20-30 mins |
|---|---|---|---|
| NSG Progestin | −8 | −12.0 | −5.3 |
| 7 µg/ml CCP | 23.8 | 21.3 | 37.5 |
| 2.7 mg/ml | 77.0 | 100.0 | 100.0 |
| 1.9 mg/ml | 36.7 | 63.3 | 65.8 |
| 1.3 mg/ml | 34.1 | 48.9 | 50.0 |
| 0.9 mg/ml | 27.8 | 27.8 | 29.6 |
| 0.6 mg/ml | 16.9 | 0 | 3.6 |

TABLE 8

Influence of CCP's extract on the contraction range of rats' extra-corporeal uterine smooth muscle (mm)

| Group | Before Adm. | After adm. 1-10 mins | After adm. 10-20 mins | After adm. 20-30 mins |
|---|---|---|---|---|
| NSG Progestin | 8.1 ± 2.1 | 8.3 ± 1.7 | 8.4 ± 2.0 | 8.4 ± 2.5 |
| 7 µg/ml CCP | 8.6 ± 2.2 | 7.4 ± 2.3 | 7.0 ± 2.6 | 7.0 ± 2.8 |
| 2.7 mg/ml | 10.8 ± 1.3 | 7.4 ± 5.2 | 0.0 ± 0.0*** | 0.0 ± 0.0*** |
| 1.9 mg/ml | 9.5 ± 1.8 | 7.0 ± 2.2 | 2.8 ± 2.7** | 1.7 ± 2.4** |
| 1.3 mg/ml | 10.4 ± 1.9 | 7.5 ± 2.0* | 5.3 ± 2.2* | 4.9 ± 2.4* |
| 0.9 mg/ml | 9.2 ± 1.9 | 8.7 ± 1.9 | 8.1 ± 1.5 | 7.8 ± 1.4 |
| 0.6 mg/ml | 8.8 ± 2.3 | 8.8 ± 2.3 | 8.7 ± 2.7 | 9.3 ± 2.5 |

*p < 0.05
**p < 0.01
***P < 0.001 (Compare with itself before administering)

TABLE 9

Influence of CCP's extraction on the contraction range of rats' extracorporeal uterine smooth muscle (Controlling percent %)

| Group | After adm. 1-10 mins | After adm. 10-20 mins | After adm. 20-30 mins |
|---|---|---|---|
| NSG Progestin | −2.5 | −3.7 | −6.2 |
| 7 µg/ml CCP | 14.0 | 18.6 | 18.6 |
| 2.7 mg/ml | 31.5 | 100 | 100 |
| 1.9 mg/ml | 26.3 | 70.5 | 82.1 |
| 1.3 mg/ml | 27.9 | 49.0 | 52.9 |
| 0.9 mg/ml | 5.4 | 12.0 | 15.2 |
| 0.6 mg/ml | 0 | 1.1 | −5.7 |

TABLE 10

Influence of CCP's extract on the contraction activity of rats' extra-corporeal uterine smooth muscle (%)

(X ± SD)

| Group | Before adm. | After adm. 1-10 mins | After adm. 10-20 mins | After adm. 20-30 mins |
|---|---|---|---|---|
| NSG Progestin | 61.5 ± 22.9 | 67.9 ± 17.7 | 72.2 ± 26.2 | 65.7 ± 18.3 |
| 7 µg/ml CCP | 69.3 ± 20.9 | 47.2 ± 22.9 | 46.3 ± 27.9 | 35.2 ± 22.5 |
| 2.7 mg/ml | 79.9 ± 15.9 | 16.7 ± 13.2 | 0*** | 0*** |
| 1.9 mg/ml | 74.1 ± 29.8 | 34.6 ± 14.0* | 13.2 ± 16.6** | 7.9 ± 10.2** |
| 1.3 mg/ml | 85.6 ± 19.0 | 41.5 ± 18.4* | 23.6 ± 18.1* | 23.2 ± 27.5* |
| 0.9 mg/ml | 99.0 ± 36.2* | 65.4 ± 12.0 | 63.5 ± 26.4 | 58.6 ± 33.2 |
| 0.6 mg/ml | 71.7 ± 31.8 | 59.9 ± 24.8 | 70.0 ± 33.1 | 73.6 ± 40.9 |

*p < 0.05
**p < 0.01
***P < 0.001

TABLE 11

Influence of CCP's extract on the contraction activity of rats' extra-corporeal uterine smooth muscle (Controlling %)

| Group | After adm. 1-10 mins | After adm. 10-20 mins | After adm. 20-30 mins |
|---|---|---|---|
| NSG | -10.4 | -17.4 | -6.8 |
| Progestin | | | |
| 7 µg/ml | 31.9 | 33.2 | 49.2 |
| CCP | | | |
| 2.7 mg/ml | 79.1 | 100 | 100 |
| 1.9 mg/ml | 53.3 | 82.2 | 89.3 |
| 1.3 mg/ml | 51.5 | 72.4 | 72.9 |
| 0.9 mg/ml | 33.9 | 35.9 | 40.1 |
| 0.6 mg/ml | 16.5 | 2.4 | -2.6 |

The results showed that the extract of CCP could inhibit the contraction of normal rats' uterus. A dose of 0.6-2.7 mg/ml of CCP determines the improving effects of the capsule with the increasing of the dose. This accounts as a dose-effect relationship.

CCP's Effect on the Contraction of Uterine Smooth Muscle Induced by Oxytocin

Animals' Grouping: randomly divide Wister female rats' extra-corporeal uteruses into normal saline control group (NSG) and CCP's group. The CCP's group is formed by 4 subgroups with seven uteruses each. The dose of CCP's extract is respectively 5.4, 2.7, 1.3, and 0.6 mg/ml.

Results: after adding 10 mu/ml oxytocin to the normal uterine smooth muscle there is an increase of the contraction frequency and the uterine activity. The contraction range is also affected reaching its peak for about 10 min to then stabilize on the level. After 40 minutes, the effect gradually drops. After the oxytocin reacts for 10 minutes, add in a different dose of CCP's extract, and compare the possible differences between the CCP's group and the oxytocin's group. A 5.4, 2.7 mg/ml dose of CCP's extract can control the increase of uterine activity induced by oxytocin, and mainly reduce contraction frequency of uterine smooth muscle (See Table 8 and 13).

TABLE 12

Influence of CCP's extract on the contraction frequency of uterine smooth muscle induced by oxytocin

| Group | Before adm. | After adm. 1-10 mins | After adm. 10-20 mins | After adm. 20-30 mins |
|---|---|---|---|---|
| NSG | 7.5 ± 1.0 | 8.4 ± 1.7 | 7.8 ± 0.9 | 7.3 ± 1.5 |
| Oxytocin | 7.0 ± 1.3 | 11.7 ± 1.5 | 11.6 ± 1.9 | 10.9 ± 1.17 |
| Oxytocin + CCP | | | | |
| 5.4 mg/ml | 8.5 ± 1.6 | 6.6 ± 0.9* | 5.3 ± 1.0** | 3.4 ± 1.8** |
| 2.7 mg/ml | 7.9 ± 1.6 | 8.9 ± 1.3* | 8.8 ± 1.3* | 7.8 ± 1.0* |
| 1.3 mg/ml | 8.4 ± 2.8 | 11.1 ± 1.6 | 11.6 ± 3.1 | 10.6 ± 2.6 |
| 0.6 mg/ml | 9.2 ± 1.5* | 13.3 ± 2.0 | 12.4 ± 3.2 | 11.5 ± 2.3 |

*p < 0.05
**p < 0.01
***P < 0.001 (compare with relevant phase's frequency of oxytocin group)

TABLE 13

Influence of CCP's extraction to the contraction frequency of uterine smooth muscle induced by oxytocin (Controlling %)

| Group | Oxytocin | After adm. 1-10 mins | After adm. 10-20 mins | After adm. 20-30 mins |
|---|---|---|---|---|
| NSG | -8 | -12 | -5.3 | 2.7 |
| Oxytocin | -91.4 | -67.1 | -65.7 | -55.7 |
| Oxytocin + CCP | | | | |
| 5.4 mg/ml | -83.5 | 20.0 | | |

TABLE 14

Influence of CCP's extract on the contraction range of uterine smooth muscle induced by oxytocin (mm)

(X ± SD)

| Group | Before adm. | Oxytocin | After adm. 1-10 mins | After adm. 10-20 mins | After adm. 20-30 mins |
|---|---|---|---|---|---|
| NSG | 8.1 ± 2.1 | 8.3 ± 1.7 | 8.4 ± 2.0 | 8.6 ± 2.5 | 7.6 ± 1.5 |
| Oxytocin | 8.0 ± 2.6 | 7.3 ± 3.2 | 9.7 ± 5.0 | 10.4 ± 5.7 | 9.7 ± 6.1 |

TABLE 14-continued

Influence of CCP's extract on the contraction range of uterine smooth muscle induced by oxytocin (mm)

(X ± SD)

| Group | Before adm. | Oxytocin | After adm. 1-10 mins | After adm. 10-20 mins | After adm. 20-30 mins |
|---|---|---|---|---|---|
| Oxytocin + CCP | | | | | |
| 5.4 mg/ml | 7.4 ± 0.9 | 7.2 ± 2.2 | 7.3 ± 1.1 | 6.7 ± 1.2 | 5.8 ± 1.7 |
| 2.7 mg/ml | 8.9 ± 2.7 | 7.5 ± 2.8 | 9.5 ± 2.7 | 10.3 ± 3.3 | 9.7 ± 2.7 |
| 1.3 mg/ml | 9.2 ± 2.3 | 8.6 ± 2.3 | 10.2 ± 1.8 | 10.6 ± 1.8 | 10.9 ± 2.3 |
| 0.6 mg/ml | 8.5 ± 2.2 | 7.1 ± 3.7 | 8.7 ± 5.2 | 8.9 ± 5.1 | 9.1 ± 5.7 |

*P < 0.05
**P < 0.01
***P < 0.001 (compare with oxytocin Group)

TABLE 15

Influence of CCP's extract on the contraction range of uterine smooth muscle induced by oxytocin (controlling %)

| Group | Before adm. | After adm. 1-10 mins | After adm. 10-20 mins | After adm. 20-30 mins |
|---|---|---|---|---|
| NSG | -2.5 | -3.7 | -6.2 | 6.2 |
| Oxytocin | 8.8 | -21.3 | -30.0 | -21.3 |
| Oxytocin + CCP | | | | |
| 5.4 mg/ml | 4.1 | 1.4 | 9.5 | 21.6 |
| 2.7 mg/ml | 15.7 | -6.7 | -15.7 | -9.0 |
| 1.3 mg/ml | 6.5 | -10.9 | -15.2 | -18.5 |
| 0.6 mg/ml | 16.5 | -2.4 | -4.7 | -7.1 |

TABLE 16

Influence of CCP's extract on the contraction activity of uterine smooth muscle induced by oxytocin (%)

(X ± SD)

| Group | Before adm. | Oxytocin | After adm. 1-10 mins | After adm. 10-20 mins | After adm. 20-30 mins |
|---|---|---|---|---|---|
| NSG | 61.5 ± 22.9 | 67.9 ± 17.7 | 72.2 ± 26.2 | 65.7 ± 18.3 | 55.4 ± 17.9 |
| Oxytocin | 56.9 ± 21.6 | 84.7 ± 22.0 | 118.8 ± 77.6 | 129.6 ± 97.3 | 111.2 ± 86.5 |
| Oxytocin + CCP | | | | | |
| 5.4 mg/ml | 62.4 ± 11.3 | 111.7 ± 39.0 | 48.7 ± 12.6 | 6.2 ± 12.8* | 21.5 ± 16.2* |
| 2.7 mg/ml | 71.0 ± 27.5 | 124.3 ± 48.8 | 84.7 ± 23.7 | 90.6 ± 32.2 | 75.9 ± 22.7 |
| 1.3 mg/ml | 79.3 ± 34.4 | 157.6 ± 61.1 | 112.3 ± 18.4 | 119.9 ± 30.1 | 111.3 ± 12.6 |
| 0.6 mg/ml | 79.1 ± 29.3 | 127.3 ± 92.8 | 122.9 ± 92.9 | 123.2 ± 115.0 | 113.7 ± 103.1 |

*p < 0.05 (compare with Oxytocin group)

TABLE 17a

Influence of CCP's extract on the contraction activity of uterine smooth muscle induced by oxytocin (controlling %)

| Group | Oxytocin | After adm. 1-10 mins | After adm. 10-20 mins | After adm. 20-30 mins |
|---|---|---|---|---|
| NSG | -10.4 | -17.4 | -6.8 | 9.9 |
| Oxytocin | -48.9 | -108.8 | -127.8 | -95.4 |
| Oxytocin + CCP | | | | |
| 5.4 mg/ml | -79.0 | 22.0 | 42.0 | 65.5 |
| 2.7 mg/ml | -75.1 | -19.3 | -27.6 | -6.9 |

TABLE 17a-continued

Influence of CCP's extract on the contraction activity of uterine smooth muscle induced by oxytocin (controlling %)

| Group | Oxytocin | After adm. 1-10 mins | After adm. 10-20 mins | After adm. 20-30 mins |
|---|---|---|---|---|
| 1.3 mg/ml | -98.7 | -41.6 | -51.2 | -40.1 |
| 0.6 mg/ml | -60.9 | -55.4 | -55.8 | -43.7 |

TABLE 17b

Influence of CCP's extract on the contraction activity of uterine smooth muscle induced by oxytocin

| Concentration (mg/ml) | Control Rate (%) |
|---|---|
| 3 | 9.06 ± 5.78 |
| 5.6 | 32.39 ± 9.15 |
| 10 | 53.63 ± 20.78 |
| 17.78 | 85.63 ± 5.91 |
| 30 | 96.01 ± 2.8 |

The result showed that after administering 5.4 mg/ml of extract of CCP for ten minutes, its effect produced a reduction of the contraction frequency of the uterine smooth muscle.

Analgesia Test

Acetic Acid Twisting Experiment

The CCP is mostly used to treat dysmenorrhea, and to release the smooth muscle of uterine. In order to prove the curative effects the drug has in the treatment of dysmenorrhea, research has been done according to the leading pharmacodynamics research requirements of the Chinese Traditional Medicine established in the "New Chinese Traditional Medicine Research Directory".

Materials

Animal: Use both female and male mice, 18 g to 23 g of weight. The Experimental Animals Center of Nanjing Railway Medical Institute was in charge of providing the animals for this experiment. The rats have access to food, water and sunlight one whole week prior to the experiment.

Medicines: Extract of Capsule of *Cinnamomi & Poria* (1 g of CCP product corresponds to 4 g of the extract). This extract is provided by Lianyungang Kanion Pharmaceutical Co. Ltd (batch No.: 990515).

Acetylsalicylic acid, 25 mg/tablet, produced by Nanjing Hengsheng Pharmaceutical Co.ltd.

Glacial acetic acid ($CH_3COOH$), concentration is 99.0%, produced by Nanjing Chemical Reagent Factory.

Experimental Results

The effect of the Celiac-injection of acetic acid can result in a typical body reaction in response to the stimulus. Mostly, there appears to be a twisting of the mice's bodies that includes an extension of hind legs and hip rising, belly sinking and lumbar bending lateral. Both the aspirin groups and the CCP group reduced the twisting times to a different extent. An obvious difference arises if compare with the normal saline control group. The results are shown in Table 14.

TABLE 18a

Influence of the extract of CCP on the twisting responses of mice induced by 0.5% acetic acid (times)

| Group & dose | Animal No. | Times of twisting (0~30 mins) | Controlling (%) |
|---|---|---|---|
| NS 0.20 ml/mouse | 12 | 38.8 ± 17.2 | |
| CCP 0.18 g/kg | 12 | 29.6 ± 14.7 | 23.7 |
| CCP 0.63 g/kg | 12 | 20.5 ± 15.0* | 47.2 |
| CCP 1.26 g/kg | 12 | 16.7 ± 13.6** | 57.0 |
| CCP 0.20 g/kg | 12 | 15.1 ± 17.1** | 61.1 |

*$p < 0.05$,
**$p < 0.01$ (compare with NSG)

TABLE 18b

Influence of the extract of CCP on the twisting responses of mice induced by acetic acid (times)

| Drag | Dosage (g/Kg) | no. of Animal | Adm. | Times of twisting 0–10 | Times of twisting 10–20 | Times of twisting 0–20 |
|---|---|---|---|---|---|---|
| Contral | — | 10 | P.O | 22.7 ± 4.4 | 23.6 ± 6.6 | 46.3 ± 7.3 |
| CCP | 2.5 | 10 | P.O | 19.3 ± 2.5* | 19.1 ± 6.6 | 38.4 ± 5.1* |
| CCP | 5.0 | 10 | P.O | 14.0 ± 6.0* | 12.9 ± 6.6** | 26.9 ± 11.7 |
| CCP | 10.0 | 10 | P.O | 10.8 ± 6.6*** | 9.6 ± 7.3*** | 9.1 ± 14.5 |
| CCP | 0.1 | 10 | P.O | | | 2.8 ± 1.4 |

*$p < 0.05$, **$p < 0.01$ (compare with NSG)

Methods

Randomly divide the animals into 5 groups. Every group has twelve rats (7 female, 5 male). Groups A, B and C are administered a 0.18 g/kg, 0.63 g/kg and 1.26 g/kg of extract of CCP respectively, once everyday for three consecutive days. Group D is administered the normal saline at 0.2 ml per mouse once everyday for three consecutive days. Group E is administered 0.2 g/kg of glacial acetic acid (Aspirin) once everyday for three consecutive days. The volume of the solution is 0.2 ml/time. After the drug has been administered on the third day, celio-inject 0.5% acetic acid to the mice in groups. Observe and record the times of twisting of mice within 30 minutes.

Controlling Percent =

$$\frac{\text{Twisting times of } NSG - \text{Twisting times of } CCPG}{\text{Twisting times of } NSG} \times 100\%$$

All data is shown with a mean ± standard deviation (X±SD). Examine the significance difference between groups using the t test.

Test of Mice's Swinging Tail

Materials

Animal: both female and male mice are grown Kunming, 18 g-23 g weight of body. The mice were supplied by the Experimental Animals Center of Nanjing Railway Medical Institute (Certificate No. Sudongzhizi-97002 & Sudonghuanzi-97003). The rats have access to food, water and sunlight one whole week prior to the experiment.

Medicines:

Extract of Capsule of *Cinnamomi & Poria* (1 g extract corresponds to 4 of crude drug), The capsule is provided by Lianyungang Kanion Pharmaceutical Co. Ltd (batch No.: 990515).

Methods

Randomly divide the animals into 4 groups. Every group has 10 rats (five female, five male). Groups A, B and C are administered a 0.18 g/kg, 0.63 g/kg and 1.26 g/kg doses of extract of CCP respectively. Group D is administered normal saline at 0.2 ml per mouse. The volume of the solution is 0.2 ml/time. Immerge one third of the mice's tails in water at 55° C. Record the swinging time of the mice's tales before administering the drug. Then, administered the drug in different dosages to the four groups and check the swinging time of mice's tale under the effect of the drugs. Record the time of swinging for one, two and four hours after the administration of the drug.

$$\text{Controlling}(\%) = \frac{\text{Swinging tail's latent time of } CCP - \text{Swinging tail's latent time of } NSG}{\text{Swinging tail's latent time of } CCP} \times 100\%$$

All data is shown with the mean± standard deviation (X±SD). Examine the different significance between groups using the t test.

TABLE 19a

Influence of CCP on mice's swinging tail latent time

| Group & dose | Before adm. | After adm. 60 mins | After adm. 120 mins | After adm. 240 mins |
|---|---|---|---|---|
| Normal saline | 1.66 ± 0.46 | 1.56 ± 0.51 | 1.62 ± 0.46 | 1.65 ± 0.36 |
| 0.18 g/kg | 1.63 ± 0.42 | 1.73 ± 0.48 (5.8) | 1.83 ± 0.49 (10.9) | 1.83 ± 0.52 (10.9) |
| 0.63 g/kg | 1.64 ± 0.34 | 2.18 ± 0.50*$_{\Delta\Delta}$ (24.8) | 1.97 ± 0.50$_\Delta$ (16.8) | .10 ± 0.56$_{\Delta\Delta}$ (21.9) |
| 1.26 g/kg | 1.58 ± 0.28 | 2.40 ± 0.61**$_{\Delta\Delta\Delta}$ (34.2) | 2.34 ± 0.68**$_{\Delta\Delta\Delta}$ (32.5) | 2.54 ± 0.69**$_{\Delta\Delta\Delta}$ (37.8) |

$p < 0.05$
**$p < 0.01$ (compare with before administering)
$_\Delta p < 0.05$
$_{\Delta\Delta} p < 0.01$
$_{\Delta\Delta\Delta} p < 0.001$ (compare with control group)

TABLE 19b

Influence of CCP on mice's swinging tail latent time

| Drag | Doses (g/Kg) | Adm. | Before Adm. | After Adm. 60 mins | After Adm. 120 mins | After Adm. 240 mins |
|---|---|---|---|---|---|---|
| Ctrl. | — | 10 | 1.58 ± 0.43 | 1.49 ± 0.4 | 1.57 ± 0.38 | 1.54 ± 0.41 |
| CCP | 5 | 10 | 1.56 ± 0.40 | 1.71 ± 0.37 | 1.91 ± 0.58 | 1.89 ± 0.66 |
| CCP | 10 | 10 | 1.55 ± 0.46 | 2.21 ± 0.93* | 2.42 ± 0.95** | 2.70 ± 0.92*** |
| CCP | 20 | 10 | 1.50 ± 0.47 | 2.57 ± 0.95** | 2.61 ± 1.27 | 2.50 ± 0.43*** |
| XYT | 0.01 | 10 | 1.58 ± 0.79 | 2.23 ± 0.53* | 2.56 ± 0.40 | 1.52 ± 0.56 |

*$p < 0.05$, $p < 0.01$, *$p < 0.001$

The experiments' results showed that a 0.63 g/kg, 1.26-g/kg extract of CCP could obviously prolong mice's time of tail swinging. Differences were noticeable when the results were compared to the normal saline control group.

Conclusion

The experiment about the influence of the extract of CCP in mice's twisting times showed that a 0.18 g/kg extract of CCP is effective in reducing the time range of the mice's twisting. The more the dose was increased (0.63 g/kg, 1.26 g/kg), the more the mice's twisting times decreased. Control rates are respectively 23.7%, 47.2% and 56.9% within 1 to 30 minutes. There is a significant difference with the normal saline control group. The control rate of the positive control-Aspirin Group is 61.08%. Since a 0.63 g/kg, 1.26 g/kg extract of CCP can obviously prolong the mice's twisting times. The results demonstrate that the CCP has strong analgesic effects on live rats.

Declining Whole Blood Viscosity

Materials
Animal: male Wister rats.

Medicines:
Extract of CCP (1 g extract corresponds to 4 crude drugs) provided by Lianyungang Kanion Pharmaceutical Co. Ltd. (batch No.: 990515).
Persantine, produced by Harbin White Swan Pharmaceutical Factory (batch No.: 8905010).
Heparin, produced by Suzhou Xinbao Pharmaceutical Factory (batch No.: 881105).
Equipment: XN-5 Type Blood Viscometer Methods Drug dispensation: put a 12.5 g extract of CCP in a 100 ml solution of normal saline and mix adequately. The drug concentration is 0.125 g/ml (containing 0.5 g/ml of crude drugs). Put a 25 extract of CCP in 100 ml of normal saline. The drug concentration is 0.25 g/ml (containing 0.1 g/ml of crude drugs). Put a 50 extract of CCP in a 100 ml of normal saline and mix adequately. The drug concentration is 0.5 g/ml (containing 2 g/ml crude drugs).

Persantine: put 2 in normal saline and mix adequately. The drug concentration will be 20 mg/ml.

Experimental processing: Randomly divide male Wister rats weighing 250 to 300 g into five groups with eight rats in each group. Low, medium and high dose groups can take the extract of CCP in a concentration of 10 ml/kg. The concentration of crude drugs is 5 g/kg, 10.0 g/kg and 20 g/kg respectively. The control group takes normal saline of the same volume; positive medicine group takes 0.2 g/kg, which is 10 ml/kg of persantine. The drug must be administered once a day for five consecutive days. After an hour and a half of administering the drug on the fifth day, lightly anaesthetize the mice with ether. Record 40 test tubes, and put 0.1 ml heparin in each. Take blood from the abdominal aorta of the mice and fill each tube with 1 ml of blood. Then use XN-5 Type Blood Viscometer to determine the Whole Blood Ratio Viscosity.

Data processing: All data is shown with the mean±standard deviation (X±SD), and the t test.

Results

The CCP's influence on the Whole Blood Viscosity of rats showed that a 5 g/kg extract of CCP could reduce the Whole Blood Viscosity to minimum low shear of P<0.01, and a maximum high shear of P<0.05. The Whole Blood Viscosity continued to drop along with the increased of the dose. The CCP can clearly reduce rats' Whole Blood Ratio Viscosity (see Table 16).

TABLE 20

Influence of CCP on the rats' Whole Blood Ratio Viscosity

| Medicine | Dose (g/kg) | Animal No. | Whole Blood Ratio Viscosity | |
|---|---|---|---|---|
| | | | low shear | high shear |
| Normal saline | 0 | 8 | 29.85 ± 9.33 | 12.10 ± 1.90 |
| CCP | 5.0 | 8 | 17.98 ± 4.78** | 9.66 ± 1.47* |
| | 10.0 | 8 | 16.69 ± 4.86** | 8.49 ± 1.81** |
| | 20.0 | 8 | 15.36 ± 4.38** | 5.60 ± 2.15** |
| Persantine | 0.2 | 8 | 16.12 ± 6.92** | 12.10 ± 1.90 |

Note:
compare with the normal saline control group,
*P < 0.05,
**P < 0.01,
***P < 0.001.

Discussion

The Whole Blood Ratio Viscosity is an index that measures the viscosity of blood. It's always related to the quantity and quality of blood corpuscle, plasma cholesterol, and fibrin macromolecular concentration. Whole Blood Ratio Viscosity is the ratio of Whole Blood Viscosity and aqueous viscosity. The more blood corpuscles are found the higher the Whole Blood Viscosity becomes. The increase of the Whole Blood Ratio Viscosity changes the blood flow as a whole, including the change of corporeal soluble components in blood. This reaction is most affected by RBC. When RBC aggregates and agglomerates, the blood viscosity increases, creating great resistance to the blood flow, a condition of high viscosity blood named "hematogenous abnormality". Because the CCP reduces blood viscosity, it is used to prevent and cure blood stasis. The Whole Blood Viscosity reflects the changes of the blood flow as a whole. Thus, the CCP can treat and improve symptoms of blood stasis.

Experiments about Extra-Corporeal Platelet Aggregation of Rabbit

Materials

Animal: Use live rabbits that weight 2.5 kg.

Medicine:

Extract of *Cinnamomi & Poria* (1 g extract corresponds to 4 g of crude drugs). The extract is supplied by Lianyungang Kanion Pharmaceutical Co. Ltd. (No.892011).

Bolus of *Cinnamomi & Poria* (1g Bolus corresponds to 4 g of crude drugs). The drug is supplied by Shanxi Changling Chinese Traditional Medicine Factory (No.900111).

Aspirin, produced by Shanghai Jiufu Pharmaceutical Company (No.900111).

Instrument: SPA-Type Platelet Aggregation instrument.

Test Preparation

Preparation of drug: Put 3.13 g of extract of CCP in 100 ml of normal saline. The drug concentration is 31.3 mg/ml (contains 125 mg/ml of crude drug). Take 1 ml from this solution, put it in 9 ml of normal saline, and mix it adequately. The drug concentration is 3.13 mg/ml (contains 12.5 mg/ml of crude drug). Put 2 ml of the solution made previously, which contains the CCP, into 8 ml of normal saline, and mix it adequately. The drug concentration is 6.26 mg/ml (contains 25 mg/ml of crude drug). Put 3 ml of the solution made with the CCP in 7 ml of normal saline, and mix it adequately. The drug concentration is 9.39 mg/ml (contains 37.5 mg/ml of crude drug). Put 4 ml of the solution made with the CCP in 6 ml of normal saline, and mix it adequately. The drug concentration is 12.5 mg/ml (contains 50 mg/ml of crude drug). Put 6 ml of the solution made with the CCP in 4 ml of normal saline, and mix it adequately. The drug concentration is 18.78 mg/ml (contains 75 mg/ml of crude drug).

Put a 1.5 g Bolus of *Cinnamomi & Poria* in 100 ml of normal saline, and mix it adequately. This solution contains 60 mg/ml of crude drug. Take 3 ml from this solution, put in 7 ml of normal saline, and mix it adequately. The solution contains 18 mg/ml of crude drug. Then put 6 ml of the solution that contains the PCP in 4 ml of normal saline, and mix it adequately. This solution contains 36 mg/ml of crude drug. Put 9 ml of the solution that contains the PCP in 1 ml of normal saline. The solution contains 54 mg/ml of crude drug. Put 0.3 g of aspirin in 1000 ml of normal saline, and mix it adequately. The solution contains 0.3 mg/ml of crude drug.

Methods a) Put 0.1 ml of 3.13% sodium citrate in 65 tubes.

b) Intubate and sample the blood of the rabbits taken from the common carotid artery while the animals are awake. Every tube should have 0.9 ml of blood. The ratio between whole blood and anticoagulant is 9:1. Centrifugalize at 1000 rpm for seven minutes and prepare PRP. After the suction of PRP, centrifugalize 10 min in terms of 3000rpm to prepare PPP. According to the Born method, use the SPA-III Type PPP Platelet Aggregation instrument for the test. Different concentrations of CCP are found: 12.5 mg/ml, 25 mg/ml, 37.5 mg/ml, 50 mg/ml and 75 mg/ml. Also different concentrations of PCP are found: 18 mg/ml, 30 mg/ml, 36 mg/ml, and 54 mg/ml. Prepare PRP using incubation for 10 min. Administer the normal saline from the same volume to the control group. Administer the aspirin to positive control group. The concentration of ADP will be 1 μm.

Data Processing $$\text{Control \%} = \frac{\text{Platelet aggregation ratio Before administering} - \text{Platelet aggregation ratio after administering}}{\text{Platelet aggregation ratio before administering}}$$

All data is shown with the mean+standard deviation (X±SD). All data between groups and within every group is examined using the t value in order to observe any significant difference. Experimental results are shown in Table 17.

TABLE 21

Influence of CCP on the extra-corporeal platelet aggregation of rabbits

| Drugs | Concentration (Mg/ml) | Sample No. | Aggregation(%) | Control(%) |
|---|---|---|---|---|
| NS | 0 | 5 | 67.95 ± 19.32 | |
| CCP | 12.5 | 5 | 51.32 ± 11.78** | 27.47 ± 7.76 |
| | 25 | 5 | 39.60 ± 12.23** | 41.72 ± 7.96 |
| | 37.5 | 5 | 25.56 ± 9.95*** | 62.30 ± 6.54 |
| | 50 | 5 | 13.74 ± 5.32*** | 79.78 ± 3.50 |
| | 75 | 5 | 3.18 ± 2.21*** | 95.33 ± 1.46 |
| Aspirin | 0.3 | 5 | 32.94 ± 1.68** | |
| NS | 0 | 5 | 66.17 ± 1.07 | |
| BP | 18 | 5 | 57.83 ± 4.83* | 32.60 ± 7.305 |
| | 30 | 5 | 34.50 ± 6.78** | 7.86 ± 10.25 |
| | 36 | 5 | 29.34 ± 7.34** | 55.67 ± 11.09 |
| | 54 | 5 | 4.50 ± 0.79*** | 93.20 ± 1.19 |

*$P < 0.05$,
**$P < 0.01$,
***$P < 0.001$ (compare with NSG)

Platelet Aggregation Experiments of Rats

Materials

Animal: male Wister rats that weight between 250 to 300 mg. The rats have access to food, water and sunlight one whole week prior to the experiment.

Medicine:

Extract of Capsule of *Cinnamomi & Poria* (1 g of extract corresponds to 4 g of crude drug), are provided by Lianyungang Kanion Pharmaceutical Co.Ltd, Batch No. 891011.

Aspirin, supplied by the Shanghai Jiufu Pharmaceutical Co., Batch No.900111.

Instrument: SPA-III Type Platelet Aggregation instrument.

Method

Preparation of drug: Put 12.5 g of extract of CCP in 100 ml of normal saline, and mix adequately. The drug concentration is 0.5 mg/ml. Put 25 g extract in 100 ml of normal saline, and mix adequately. The drug concentration is 1 g/ml. Put 50 g of extract of CCP in 100 ml of normal saline, and mix adequately. The drug concentration is 1 g/ml.

Experimental process: Randomly divide 34 male Wister rats into five groups, and respectively administer the following doses of CCP: 5g/kg, 10 g/kg, 20g/kg. Administer 10 ml/kg of normal saline of the same volume to the control group, once a day for five consecutive days. Half an hour after administering the drug on the fifth day, use ether to anaesthetize the rats. Using a total of 34 tubes, pour 0.1 ml of 3.13% sodium citrate in every tube to prevent the blood from coagulating. Administer a 0.1 g/kg aspirin once to the positive control group. Prepare platelet plasma according to the method explained previously. Do the aggregation experiments, and record the conditions of every group.

Data processing: All data is shown with the mean ±standard deviation (X±SD). All data between groups and within every group is examined using the t value in order to observe any significant difference. Experimental results are shown in Table 18.

TABLE 22

CCP's influence to platelet aggregation of rats (X ± SD)

| Medicine | Dose (g/kg) | Animal No. | Aggregation ratio |
|---|---|---|---|
| NS | 0 | 7 | 65.33 ± 11.05 |
| CCP | 5.0 | 7 | 56.19 ± 7.70 |
| | 10.0 | 7 | 51.78 ± 9.68** |
| | 20 | 7 | 44.86 ± 7.99** |
| Aspirin | 0.1 | 6 | 26.58 ± 10.58** |

*$P < 0.05$,
**$P < 0.01$,
***$P < 0.001$ (compare with Normal saline)

The experiments about extracorporeal platelet aggregation of rabbits made it possible to find that by using 12.5 mg/ml of crude drug extract of CCP there is a significant reduction of the platelet aggregation ratio ($P<0.05$). The higher the concentration (e.g.,37.5 mg/ml, 50 mg/ml, 75 mg/ml) the more the platelet aggregation ratio drops. In experiments about extracorporeal platelet aggregation of rats, the extract of CCP can obviously reduce the platelet aggregation ratio when the dose ranges from 10 g/kg to 20 g/kg. The higher the dose, the stronger the effect. The results showed that the CCP could control the rate of blood platelet aggregation induced by ADP.

Discussion

Adhesion, aggregation and exergic reactions of the platelet are the basic functions under physiological conditions. It is also the thrombosis factor under pathological conditions.

An important method for the treatment of blood stasis is to control the platelet aggregation and reduce blood viscosity in order to improve blood circulation. This is basically a method used to activate blood circulation in an attempt to dissipate blood stasis.

ADP results in blood aggregation by the ADP receptor. The results obtained from the experiments showed that the CCP could control the platelet aggregation induced by ADP. The results also indicated the existent of a dose-effect relationship.

After administering the CCP, there is a high level of control of the platelet aggregation, which is induced by the ADP. This process showed that the CCP has properties that activate blood circulation in order to dissipate blood stasis.

Anti-Inflammation Effect

Material

Animal: Kunming mice, provided by the Experimental Animal Room in our institute.

Medicines:

Extract of CCP, provided by Lianyungang Kanion Pharmaceutical Co. Ltd., Batch No. 891011 (1 g extract corresponds to 4 crude drug).

Bolus of *Cinnamomi & Poria*: produced by Shanxi Changzhi Chinese Tradition Medicine Factory (1 g extract correspond to 4 crude drug), Batch No. 900407

Hydrocortisone, produced by Harbin Third Pharmaceutical Factory, Batch No. 900407

Instrument: Stiletto machine; Torsion balance

Methods

Preparation of drug: Put 12.5 g of extract of CCP in 100 ml of normal saline, and mix adequately. The drug concentration is 0.5 mg/ml. Put 25 g of extract of CCP in 100 ml of normal saline, and mix adequately. The drug concentration is 1 g/ml. Put 50 g of extract of CCP in 100 ml of normal saline, and mix adequately. The drug concentration is 2 g/ml. Put 12.5 g of the Bolus of *Cinnamomi* & *Poria* in 100 ml of normal saline, and mix adequately. The drug concentration is 0.5 mg/ml. Put 25 g of extract in 100 ml of normal saline, and mix adequately. The drug concentration is 1 g/ml. Put 50 g of extract in 100 ml of normal saline, and mix adequately. The drug concentration is 2g/ml. Put 0.1 g of Hydrocortisone in 100 ml of normal saline. The drug concentration is 1 mg/ml. Administer all three preparations (a total of seven different solutions) with 10 ml/kg.

Experimental method: According to their weight, randomly divide fifty male mice into eight groups. Administer different doses of the seven solutions mentioned above for three days and for the control group administer the normal saline of the same volume. After three days of administering the drug, besmear 0.5 ml croton oil on both sides of every mouse's left ear (compare with right ear). Two hours after administering the drug, kill the animals, and punch holes in the same location on their ears with 9 mm Stiletto machine, then weigh the ears of mice with Torsion balance.

Swollen degree=left ear's weight−right ear's weight.

All data is shown with the mean±standard deviation (X±SD). Data between groups and within every group is examined using the t value in order to observe any significant difference.

Results

Experimental results showed that a 10 g/kg CCP could reduce the degree of ear swelling (p<0.01). It has been proven that an increase of the dose produces a reduction of the swelling. The degree of ear swelling of the group with a dosage of 20 g/kg of the extract of CCP is 5.92±3.11. Significant differences were found between the CCP in comparison with the normal saline control group (p<0.001).

TABLE 23

Influence of the CCP on the ear swelling of mice

| Group | Dose(g/Kg) | Animal No. | Average swelling degree |
|---|---|---|---|
| Control | 0 | 10 | 18.36 ± 7.09 |
| CCP | 5 | 10 | 17.75 ± 4.81 |
|  | 10 | 10 | 9.05 ± 5.92** |
|  | 20 | 10 | 5.92 ± 3.11** |
| BCP | 5 | 10 | 17.85 ± 3.06 |
|  | 10 | 10 | 10.90 ± 2.93 |
|  | 20 | 10 | 8.17 ± 5.91** |
| Hydrocortisone | 0.025 | 10 | 4.68 ± 3.43*** |

Discussion

Inflammatory agents can penetrate through the skin causing serious damage to the ear. Results from this experiment determined that a 10-20 g/kg extract of CCP could reduce the swelling induced by an inflammatory agent. The higher the doses of extract of the CCP, the stronger the effect. The information reported from previous research validates the fact that the CCP has anti-inflammatory characteristics.

Conclusion

The extract of CCP can control the contraction frequency, the range and the activity of the extra-corporeal uterine smooth muscle. It can also reduce rats' contraction frequency and activities of uterine smooth muscle induced by oxytocin. The experiments proved that a 0.18 k/kg extract of CCP could decrease the twisting times of mice. By examining the Whole Blood Ratio Viscosity of rats, we found that a 5.0 g/kg of crude drug of CCP can reduce the Whole Blood Ratio Viscosity. Through this experiment is noticeable the existent difference with the normal saline control group (low shear P<0.01, high shear P<0.05). The experiments indicated that the CCP could obviously reduce Whole Blood Ratio Viscosity.

The results showed that a 12.5 mg/ml of crude drug of CCP could reduce the platelet aggregation rate. The platelet aggregation rate could be reduced if the CCP dose was increase (e.g., 37.5 mg/ml, 50 mg/ml, 75 mg/ml). In regards to the results obtained from the experiment involving the platelet aggregation, it was proven that a 10 g/kg extract of CCP could reduce the platelet aggregation ratio. The results indicated that a 10 g/kg extract of CCP could reduce auricular swelling (P<0.01) proving the strong anti-inflammatory effect of the CCP.

General Pharmacological Studies on Capsule of *Cinnamomi* and *Poria* (CCP)

According to the National guide principle for pre-clinical study of new drug. Experiments were taken to assess the effect of Capsule of *Cinnamomi* and *Poria* (CCP) on the mental and nervous, cardiovascular and respiratory systems of rats. The results indicated that there was no significant effects upon functions of those systems after the animals were treated with CCP at doses of 250 mg/kg/day and 500 mg/kg/day for 5 days.

Materials

Capsule of *Cinnamomi* and *Poria* (CCP) was provided by Lianyungang Kanion Pharmaceutical Co. Ltd. The batch number is 0002145 (the pan-mixed date: Mar. 30, 2000).

Wistar rats were provided by Nanjing Military Area Major Hospital Experiment Animal Center (NMAAMH-EAC), certificate number Su-Dong(Zhi) 97001. Animals were raised in the animal house after purchased with temperatures ranged from 18-24° C., light exposure was approximately 12 hours. The food for animals was the granular rat food provided by NMAAMH-EAC The experiment begins after 2 weeks of breeding.

Equipments: JZ-1 tonotransducer, provided by Beijing Chenyung electrotechnical Institue; CY-BK pressure transducer, provided by BeKo Measure -Control L.T.Co.; Ms 322 Multimedia Biology Signal Analytical System, provided by Guozhuo Pharmaceutical College.

Data were dealt with Pentium II 300 computer. The speed of record was 0.2s/cm and the plus were: ECG 1 mv/cm, BP 8 mv/cm, respiratory 8 mv/cm, and all results are expressed as mean±S.D, and analysis by student t test.

Methods 30 adult rats were randomly divided into 3 groups, each contained 10 rats, equal in both genders. CCP was given by gastric gavage to rats at a dose of 250 mg/kg or 500 mg/kg for 5 days. The other group was given saline as control.

Observation for Nervous System: To observe the general appearance, behaviors, posture, gait of animals before and after the treatment. Pay attention to signs like salivation, muscle trembling or changes of the eye pupil.

Observation for Cardiovascular system: The rats were under anesthesia before and after administration and were recorded for their Blood Pressures (BP), Electrocardiogram (ECG) in II lead for the rates and rhythms of the heart.

Observation for Respiratory system: The animals were on anesthesia and tracheal cannular that were connect to the MBSAR to measure the change of respiratory frequency.

Results:

The effects of CCP on Nervous system: The experiments showed that there were no significant changes before and 1-56 hours after the treatment for such aspects as appearance, hairs, general behavior (appetite, and sleep), posture, and gait. Neither did CCP show effect on salivation, muscle trembling and change of the eye pupil.

The effect of CCP on cardiovascular and respiratory system: The experiment showed that there are no changes on Blood Pressure ECG, heart rate or respiratory frequencies between the control group and experimental groups.

TABLE 24

The effect of CCP on heart rates of rats (Times/Min)

| Control | 250 g/kg | 500 g/kg |
|---|---|---|
| 322.8 ± 76.0 | 355.0 ± 67.3 | 387.9 ± 63.8 |

TABLE 25

The effect of CCP on BP of rats (Kpa)

| Control | 250 g/kg | 500 g/kg |
|---|---|---|
| 19.6 ± 4.2 | 21.2 ± 7.2 | 17.8 ± 6.1 |

TABLE 26

The effect of CCP on respiratory frequencies of rats (Time/Min)

| Control | 250 g/kg BW | 500 g/kg BW |
|---|---|---|
| 83.1 ± 29.1 | 80.2 ± 18.3 | 76.2 ± 17.8 |

Conclusion

This experiment showed that CCP has no effect on the mental, nervous, respiratory and cardiovascular systems in rats that were under the dosages of 250 mg/kg and 500 mg/kg during the 5 days experiment.

Acute Toxicity Study of CCP 20 mice of 18-22 gram in body weight, equal in numbers of both genders, were given to CCP solution by gastric gavage 0.8 ml twice a day (246 g/kg.day) for 7 days. Observe and make notes to the toxic effect, abnormal symptoms and deaths for 7 days. Animals were quirt and less active, but neither obvious reaction nor death could be observed when drug dosage was raised up to 246 g/kg, a thousand times more than human's dosage at 10 a day.

Long-Term Toxicity Study of CCP

According to the National guide principle of pre-clinical study for a new drug. A chronic toxicity study on CCP is required. The result of this study were negative and it indicated that there was not any reverse effect acting on the functional and structural internal organs of the rats after treated with CCT at doses of 250 mg/kg/d, 500 mg/kg/d and 1000 mg/kg/d for a 3 months period.

Materials

Capsule of *Cinnamomi* and *Poria* (CCP) was provided by Lianyungang Kanion Pharmaceutical Co. Ltd. The batch number is 0002145(the pan-mixed date: Mar. 30, 2000).

Wistar rats were provided by Nanjing Military Area Major Hospital Experiment Animal Center (NMAAMH-EAC), certificate number Su-Dong(Zhi) 97001. Animals were raised in the animal house after purchased with temperatures ranged from 18-24° C., light exposure was approximately 12 hours. The food for animals was the granular rat food provided by NMAAMH-EAC The experiment begins after 2 weeks of breeding.

Method

The adult rats were divided into 4 groups randomly, each group contained 20 animals (10 males and 10 females). The rats was given CCP by gastric gavage at doses of 250 mg/kg/d, 500 mg/kg/d, and 1000 mg/kg/d, 6 days a week for 3 months. The other group was given saline as a control group.

Parameters Evaluated

General Appearances, behaviors, excretions, appetite, and weight changes. After 24 hours of the last dose, the rats were sacrificed and were observed for the following index.

1) Hematology: The count of RBC, WBC, platelet and hemochrome.
2) Biochemical parameters of blood: AST, ALT, BUN, TP, ALB, GLU, T-BIL, Crea, and T-CHO.
3) Histopathology examination: The important organs such as pituitary, heart, liver, kidney, lung, testis, ovary, uterus, lymph, stomach, thyroid, duodenum, ileum, and colon were all dissected out and fixed in Bounin's solution. Then the organs were to be embedded in paraffin wax and serially sectioned. The sections were stained with H. & E. stain and examined by a light microscope.

Results

There were no changes or any difference between the control group and CCP groups on rat's appearances, behaviors, excretions, appetite, body weight and weight of the organs. The rats that were given CCP by gastric gavage at dose of 250 mg/kg/d, 500 mg/kg/d, and 1000 mg/kg/d for a 3 months period did not showed any treatment related signs of effect.

TABLE 27

Effect of CCP on important organs weight

| | Heart | Lung | Kidney | Liver |
|---|---|---|---|---|
| Control | 0.39 ± 0.04 | 0.78 ± 0.02 | 0.95 ± 0.07 | 4.82 ± 0.26 |
| 250 mg | 0.37 ± 0.05 | 0.86 ± 0.07 | 1.06 ± 0.08 | 4.92 ± 0.52 |
| 500 mg | 0.38 ± 0.03 | 0.79 ± 0.04 | 1.06 ± 0.08 | 4.80 ± 0.36 |
| 1000 mg | 0.45 ± 0.03 | 0.80 ± 0.05 | 1.04 ± 0.10 | 4.70 ± 0.39 |

| | Spleen | Uterus | Ovary |
|---|---|---|---|
| Control | 0.18 ± 0.01 | 0.17 ± 0.03 | 0.028 ± 0.004 |
| 250 mg | 0.16 ± 0.01 | 0.17 ± 0.02 | 0.022 ± 0.008 |
| 500 mg | 0.18 ± 0.01 | 0.17 ± 0.01 | 0.028 ± 0.004 |
| 1000 mg | 0.19 ± 0.02 | 0.17 ± 0.03 | 0.028 ± 0.003 |

There were no significant change between the control and CCP groups in count of RBC, WBC, platelet and hemochrome during 3 months of the experiment. The CCP groups were given the dosages of 250 mg/kg/day, 500 mg/kg/day or 1000 mg/kg/day.

TABLE 28

The effect of CCP on hematology parameters

| Group | RBC $10^6/mm^3$ | WBC $10^3/mm^3$ | Platelet $10^3/mm^3$ | Hb g/100 ml |
|---|---|---|---|---|
| Control | 4.49 ± 0.53 | 15.2 ± 4.6 | 1170 ± 141 | 13.1 ± 1.6 |
| 250 mg/kg | 3.95 ± 0.41 | 13.6 ± 4.1 | 1159 ± 156 | 12.2 ± 1.1 |
| 500 mg/kg | 4.56 ± 0.51 | 15.6 ± 5.0 | 1073 ± 76 | 13.0 ± 2.0 |
| 1000 mg/kg | 4.28 ± 0.39 | 14.7 ± 4.5 | 1129 ± 137 | 12.4 ± 2.0 |

There was no significant change or difference between the CCP groups and the control group in parameters of AST, ALT, BUN, Crea, TP, GLU, T_BIL, and T-CHO. It was suggested that CCP has no effects on the function of liver, kidney, and the metabolism 15 of protein, Carbohydrates, and fat during the 3 months of the experiment. The dosages of CCP that were given to the rats were 250 mg/kg/d, 500 mg/kg/d, and 1000 mg/kg/d.

TABLE 29

The effect of CCP on the functions of the liver and kidney.

| Group | AST (u) | ALT (u) | BUN (mg/100 ml) | Cr (mg/100 ml) |
|---|---|---|---|---|
| Control | 18.3 ± 8.6 | 13.8 ± 2.7 | 39.7 ± 7.6 | 1.38 ± 0.23 |
| 250 mg/kg | 18.3 ± 4.2 | 15.3 ± 5.1 | 15.3 ± 5.1 | 1.32 ± 0.25 |
| 500 mg/kg | 15.4 ± 6.7 | 17.2 ± 6.0 | 39.1 ± 8.4 | 1.38 ± 0.23 |
| 1000 mg/kg | 17.3 ± 6.6 | 15.3 ± 4.3 | 38.6 ± 10.0 | 1.41 ± 0.21 |

TABLE 30

The effect of CCP on the metabolism of Carbohydrates, protein and fat

| Group | TP g/100 ml | ALB g/100 ml | GLU mg/100 ml | T-BIL mg/100 ml | T-CHO mg/100 ml |
|---|---|---|---|---|---|
| Control | 5.96 ± 1.08 | 4.09 ± 0.82 | 101.6 ± 12.1 | 0.37 ± 0.18 | 113.1 ± 16.9 |
| 250 mg/kg | 6.28 ± 0.92 | 4.39 ± 0.86 | 114.3 ± 12.2 | 0.39 ± 0.19 | 117.5 ± 19.9 |
| 500 mg/kg | 6.35 ± 0.86 | 4.08 ± 0.87 | 99.8 ± 13.3 | 0.38 ± 0.18 | 127.3 ± 28.6 |
| 1000 mg/kg | 6.30 ± 0.87 | 4.22 ± 0.57 | 99.0 ± 15.4 | 99.0 ± 15.4 | 120.5 ± 21.4 |

Histopathology examinations: Many of the organs such as pituitary, heart, liver, kidney, lung, testis, ovary, uterus, lymph, stomach, duodenum, ileum, and colon were all dissected and were put into Bounin's solution. Then the organs were to be embedded in paraffin wax and serially sectioned. The sections were stained with H.& E. stain and examined under microscope. The results of all three treated groups showed no structural and other changes that were compared to the control group.

Conclusion

The results indicated that there were no significant effects on the functions and structure of all examined organs, during the 3 months period of experiment that the rats were given the dose of CCP by 250 mg/kg/d, 500 mg/kg/d and 1000 mg/kg/d. In conclusion, the experiment showed that CCP are safe for usage.

Effect on Genital System of Female Young Rat

Materials

Capsule of *Cinnamomi* and *Poria* (CCP) was provided by Lianyungang Kanion Pharmaceutical Co. Ltd. (Batch No. 990515)

Radio-immunoassay Kits for oestadiol (Sensitivity: 4 pg/ml; variation index between batches: 5.0, within batch: 4.0) and pregnendione(Sensitivity: 0.2 ng/ml; variation index between batches: 7.4, within batch: 5.2), provided by Jiuding Biomedical company Ltd., Tianjin 30 female Wistar rats, 4 weeks of age, provided by Nanjing Military Area Major Hospital Experiment Animal Center (NMAAMH-EAC), certificate number Su-Dong(Zhi) 97001. Animals were raised in the animal house of our institute, the temperatures was ranged from 18-24° C., light exposure was approximately 12 hours. Animal's food was the standard granular rat food provided by NMAAMH-EAC.

Method 30 rats were randomly divided into high, low doses and control groups, 10 rats in each group. The three groups of rats were administered with CCP 1,500 mg/kg.day, 300 mg/kg-.day, or normal saline 0.4 ml/rat for 7 days. Animals were killed on the eighth day, uteruses and ovaries were weighted immediately and blood sample toke from the abdominal aorta for concentration of serum oestadiol and pregnendione.

Result

Two animals, one in the high dose and the other the control group died one hour after the gastric infusion. We considered that the death was caused by inappropriate operation of gastric infusion since certain bloody fluid was found in the mouths of both rats. No other abnormal cases were found during the test for their growth, body developing action and reactions.

TABLE 31

Weight of genital organs after administrations

| Group | Number of rat | Body weight (g) | Weight of uterus (mg) | Index of uterus | Weight of ovary (mg) | Mean ± SD Index of ovary (mg) |
|---|---|---|---|---|---|---|
| Control | 9 | 63.8 ± 3.5 | 114.8 ± 18.3 | 180.6 ± 31.9 | 54.8 ± 5.0 | 86.3 ± 10.1 |
| High dose | 9 | 66.7 ± 6.7 | 130.4 ± 12.3 | 196.2 ± 13.7 | 58.4 ± 5.7 | 88.1 ± 8.7 |
| Low dose | 10 | 68.9 ± 6.0 | 120.5 ± 22.0 | 177.6 ± 34.0 | 55.2 ± 7.6 | 80.4 ± 10.3 |

In compare with the control, there was no significant difference in the CCP groups (P>0.05)

TABLE 32

Level of Serum oestadiol and pregnendione.

| Group | Number of rat | Oestadiol (pg/ml) | Pregnendione (ng/mg) |
|---|---|---|---|
| Control | 9 | 4.1 ± 1.4 | 0.47 ± 0.22 |
| High dose | 9 | 4.3 ± 2.1 | 0.60 ± 0.45 |
| Low dose | 10 | 3.6 ± 1.1 | 0.63 ± 0.41 |

In compare with the control, there was no significant difference in the CCP groups (P>0.05)

Conclusion

CCP showed no obvious adverse effect on the genital systems of young adult rat (4 weeks) after 7 days administration of high/low doses.

The Micronucleus Test of CCP

According to the Chinese National Guide Principle of pre-clinical study for new drugs. A Micronucleus Test was conducted. By the results of this test, we would be able to tell the mutagenesis effect of CCP and the range of the effect. It was found that there was no increasing micronucleus after treated with CCT by gastric gavage at doses of 2.5 g/kg/day, 1.25 g/kg/day and 0.625 g/kg/day for 2 days.

Materials

ICR adult mouse were provided by Nanking Military Area Major Hospital Experimental Animal Center, certificate number: Su-dong (Zhi) 95040. Animals were raised in the animal house after purchased with temperatures ranged from 18-24° C., light exposure was approximately 12 hours. The food for animals was the granular rat food provided by NMAAMH-EAC The experiment begins after 1 weeks of breeding.

Capsule of *Cinnamomi* and *Poria* (CCP) was provided by Lianyungang Kanion Pharmaceutical Co. Ltd. The batch number is 0002145(the pan-mixed date: Mar. 30, 2000).

Method:

30 mice were randomly divided into 5 groups, each group contained 6 animals. Three of the groups were drug-groups and animals in them were given to CCP by gastric gavage at doses of 2.5 g/kg/day, 1.25 g/kg/day and 0.625 g/kg/day for 2 days. (LD50 of CCP from an acute toxicity test was 5 g/Kg, we adopted a half dose for our study). The fourth group is given to normal saline (0.5 ml/mice) as a negative control group. The last group was given to cyclophosphamide(CP) at 40 mg/Kg via abdominal cavity injection as a positive control group.

Animals were killed 24 hours after administration. Both femurs of the mice were taken for sampling. Femurs were pressed to move out the marrow, with a drop of calf serum added to it, smear the marrow on a plate. After the smeared plate was fixed in the solution of methyl for 10 minutes, it was dyed with the Giemsa's method and observed under the oil lens of a microscope. In the principle of double-blinded study, PCE and MNPCE cells were counted. 1000 PCE and MNPCE cell were counted for each mice, calculated the ratio of micronuclei over the 1000 cells. The ratio of micronuclei represents the dose-effectiveness relation. The data was analyzed with statistical t test.

Results

It was found that the incidence of micronucleus in the group of cyclophosphamide injection was obviously higher than the negative control. Yet, there was no statistical difference between CCP groups and the negative control for the incidence of micronucleus in mice's marrow cells.

TABLE 33

The number of micronuclei in mice administered with different dosages of CCP with the control groups

| Group | Animals | PCE Cells | Micronuclei |
|---|---|---|---|
| Negative control | 6 | 6000 | 12 |
| Positive control | 6 | 6000 | 381 |
| 2.500 g/Kg | 6 | 6000 | 25 |
| 1.250 g/Kg | 6 | 6000 | 18 |
| 0.625 | 6 | 6000 | 17 |

TABLE 34

The incidence of micronuclei in mice administered with different dosages of CCP with the control groups

| Group | X ± SD | Range |
|---|---|---|
| Negative control | 2.6777 ± 1.0328 | 1-4 |
| Positive control | 63.5000 ± 20.6373 | 43-98 |
| 2.500 g/Kg | 401667 ± 2.4833 | 2-9 |
| 1.250 g/Kg | 3.0000 ± 1.7889 | 1-6 |
| 0.625 g/Kg | 2.8333 ± 2.1370 | 1-7 |

Conclusion

High (2.500 g/Kg), middle (1.250 g/Kg), and low (0.625 g/Kg) dosages of CCP had no significant effect on improving the incidence of micronucleus in mice bone marrow cells. Therefore, we have concluded that this drug had no harmful effect on chromatosome.

The Ames Test of CCP

In compliance with the Chinese National Guide Principle of pre-clinical study for new drugs, an "Ames" test on CCP was performed to decide the possible effect of mutagenesis of the drug. It was found that after blending of CCP into bacterial strains TA97, TA98, TA100 and TA102 at concentrations of 5 mg/plate, 0.5 mg/plate, and 0.05 mg/plate, the number of back mutation colonies in each culture plate did not increase with or without the 'S9'. Meanwhile, the positive control showed an increased number of back mutation colonies. This test demonstrated that CCP had no mutagenesis effect.

In this experiment, the blending of the suspend drug in different doses into the culture plates of *S. Typhimurium* mutational strains without Histidine might cause changes in the number of back mutation colonies if the drug is effective in mutagenensis.

Materials

*S. Typhimurium* TA97, TA98, TA100, and TA102 were provided by Epidemic Prevention Station, Jiangsu, People's Republic of China. The bacterial strains were cultured at 37° C. in vibrate water bath until the number of bacteria raised up to $1 \times 10^9$; CCP was provided by the Lianyungang Kanion Pharmaceutical Co. Ltd., batch number: 0002145 (the pan mixed date: Mar. 30, 2000).

Drugs for positive control: 1) solution of sodium azide, add 1.5 ml sodium azide(1.5 ug/1.0 ml) into 500 ml water. Filter the solution to eliminate contaminating bacteria in it. 2) solution of 2-amino fluorine, add 40 ml 2-amino fluorine (200 ug/1.0 ml) into 200 ml water, Filter the solution to eliminate contaminating bacteria in it.

Hepatic microsome enzyme (S9): provided by Jiangsu Epidemic Prevention Station, People's Republic of China.

Reagents: glucose-6-phosphate, coenzyme II, histidine, and biotin were provided by Shanghai Biochemistry Reagent Company, the agar by Japan NAGASKITG Biochemistry Company. The rest of the reagents were produced by Nanjing Chemistry Reagent Company, People's Republic of China.

Methods:
1) The first step of the test was to establish a sketch on its bacterial inhibition effect and the dosages used for the second step test in relation to the possible effect: a) *Bacillus coli* were inoculated into a conical flask of nutrient broth medium (about 20 ml), and put into incubator at 37° C. for 24 hours for the increase of bacteria number. b) The test was operated on 9 cm bacteria culture plates. Add 5.0 mg, 0.5 mg, 0.05 mg of CCP, or 0.1 ml of normal saline into plates with 15 ml of nutrient agar and 0.1 ml the bacteria fluid. The plates were cultured in incubator at 37° C. for 24 hours. After incubation, the number of colonies in each plate had no significant difference. The result showed that CCP had no bacterial inhibition effect even with the enhanced experimental dosages. ) Step two: a) Inoculated *S. Typhimurium* TA97, TA98, TA100, and TA102 respectively into conical flasks with nutrient's broth medium (about 20 ml) and cultivated them in incubator at 37° C. for 24 hours. b) The test was operated in 9 mm culture plates following regular procedures for the preparation of reagents, culture plates and suspending drugs of different dosages, the inoculation of bacteria strains, cultivation in incubator etc. c) Three suspending drug groups of low, middle, and high dosages, one negative control (auto reverse) and two positive controls (sodium azide and 2-amino fluorine) were setup for the test.

Each of the above mentioned groups were operated for three cultural plates observation. Concentrations of drugs and agents of each group were showed in table 31

TABLE 35

The groups for Ames test

| Groups | TA 97, TA 98, TA 100 or TA 102 (ml/plate) | Normal Saline (ml/plate) | CCP (ml/plate) | sodium azide (μg/plate) | 2-amino fluorine (μg/plate) | S9 ml/late) | S9 buffer, 1/late) |
|---|---|---|---|---|---|---|---|
| Negative Ctrl | 0.1 | 1.0 | | | | 0.5 | 0.5 |
| Positive (Sodium axide) | 0.1 | | | 1.5 | | | 0.5 |
| Positive (2-amino fluorine) | 0.1 | | | | 10.0 | 0.5 | 0.5 |
| CCP low | 0.1 | | 0.05 | | | 0.5 | 0.5 |
| CCP mid | 0.1 | | 0.50 | | | 0.5 | 0.5 |
| CCP high | 0.1 | | 5.00 | | | 0.5 | 0.5 |

Results:
The number of Back Mutation Colonies (BMC) in each CCP dose group was not increased with or without the presence of S9. The positive control groups had been increased significantly for the back mutation colonies.

TABLE 36

The Number of Back Mutation Colony in Ames Test

Back Mutation Colony (colony/plate, mean ± SD)

| | TA 97 | | TA 98 | | TA 100 | | TA 102 | |
|---|---|---|---|---|---|---|---|---|
| Group | −S9 | +S9 | −S9 | +S9 | −S9 | +S9 | −S9 | +S9 |
| Negative Control | 147.7 ± 2.1 | 152.0 ± 29.5 | 24.7 ± 3.2 | 24.0 ± 3.66 | 99.3 ± 8.4 | 117.1 ± 14.6 | 186.0 ± 39.8 | 215.7 ± 33.0 |
| Sodium axide | 1120.0 ± 233.5** | | 1072.3 ± 215.9** | | 1163.0 ± 92.3** | | 1005.7 ± 8301** | |
| 2-amino fluorine | 1109.7 ± 58.8** | | 1131.7 ± 233.32** | | 1095.7 ± 118.2** | | 1080.0 ± 89.4** | |
| CCP low | 156.7 ± 12.2 | 169.3 ± 12.1 | 22.0 ± 1.0 | 27.3 ± 4.5 | 101.7 ± 9.0 | 106.0 ± 18.1 | 236.0 ± 73.4 | 258.0 ± 71.3 |
| CCP mid | 84.7 ± 7.5 | 118.3 ± 12.3 | 24.7 ± 4.5 | 25.0 ± 6.2 | 150.3 ± 6.7 | 149.3 ± 12.7 | 238.0 ± 64.2 | 233.3 ± 43.9 |
| CCP high | 127.0 ± 20.0 | 146.0 ± 29.1 | 26.7 ± 4.0 | 28.0 ± 1.7 | 146.3 ± 12.7 | 156.3 ± 18.0 | 247.7 ± 21.4 | 218.7 ± 19.7 |

**In compare with the negative control (auto reverse), the two positive groups showed the most significant difference ($P < 0.001$).

Conclusion

The test showed that CCP had no mutagenesis effect on the 4 strains of Histidine Defect S. Typhimurium.

Evaluation of CCP for Carcinogenicity in Cellular Malignancy Transformation on Mammal's Cells In Vitro According to the National guide principle of pre-clinical study for new drugs. The carcinogensis of CCP was studied with cellular malignancy transformation test. Study on the Syrian Hamster embryo cell in vitro, the results indicated that there was no malignant cell clone transference found among 50 culture flasks tested with CCP at dosages from 10 mg/flask to 0.625 mg/flask. The malignant transformation test concluded that there was no carcinogensis effect of CCP Materials Capsule of *Cinnamomi* and *Poria* (batch number: 0002145, TCM) was provided by Lianyungang Kanion Pharmaceutical Co. Ltd.; The Syrian Hamster embryo (SHE) cell was donation from Dr. Li Xiangming, Medical College of YangZhou University; RPMI 1640 medium and culture flasks were products of Gibco Co.; Penicillin and streptomycin were products from Yanan pharmaceutical factory, Shanghai; Fetal bovine serum was from Jinling biotechnology Co., Nanjing; The rest of chemicals or reagents were from Jiangsu Chemical Reagent Co.

$CO_2$ Incubator was purchased from Lab-Line instruments Inc., USA. YJ-875 clean worktable was from the Suzhou cleaning Equipment Factory. Multifunction microscope was purchased from Olympus Co. Japan. $CO_{60}$ radiative was provided by Academy of Agricultural Science Jiangsu, China.

Method

Cultivation of the SHE cell: In sterile circumstance, the ample of SHE cell was unfrozen and restored in a water bathe at 37° C. and inoculated into several culture flasks. Cultured at 37° C., humid, with 5% $CO_2$ and 95% air, the cell was to be washed in Hank's balanced salt solution (BBS) after a 24 hours culturing in order to remove the dimethyl sulfoxide (DMSO). The cells were to be cultured in the RPMI medium 1640 with 10% fetal calf serum, penicillin and streptomycin for the other 24 hours. After that, the cells were seeded at $1 \times 10^5$ viable cells per 5 ml culture medium in 30 ml flasks and cultured for 48 hours. After the 48 hours, the cells were exposed to $CO_{60}$ radiation for a dosage of 70 Gy. Cells were prepared as "nourishing cell" after the above procedures.

On the third day of the experiment, another ample of SHE cell was restored and cultured for proliferation, but were not exposed to CO60 radiation. They were what we called the "target cell". The target cells were inoculated at $1 \times 10^3$ per flask to the nourishing cell's flasks on the sixth day of cultivation and the seeded flasks were to be cultured for another 1 or 2 days.

CCP was grinded into a fine powder substance and was blended with culture medium. The prepared drug medium was then filled into the flasks of cells and the cells were exposed to CCP drug medium and cultivated for 24 hours before the drug medium was removed and the cells were washed 3 times in the BBS to remove the remaining drugs. The flasks of cells were then filled with "drug-free" medium and were cultivated for 10-12 days. During the days, the culture medium was scheduled to changed once every other day.

Result

A total 70 flasks of 7 groups were prepared, 10 flasks for each group. Group A, B, C, D, and E were exposed to the test drug—CCP at dosages of 10 mg/flask, 5 mg/flask, 2.5 mg/flask, 1.25 mg/flask, and 0.625 mg/flask. Group F was a positive control with MNNG at 5 mg/flask. Group G was negative control. After the final culture, the cells were taken out and chemically fixed in methanol for 15 minutes. Dried in the air, the cells were dyed in 10% Giemsa for 20 minutes and then, they were ready to be studied under the microscope. The cells were observed for their appearance and colonies morphologically in cell formation or transformation. There are differences between normal and malignant transformed cell colony in cell morphology in visions under a phase contrast microscope. The cells and colonies were observed and recorded for 61-70 culture flasks (9 cultures were discarded due to bacterial contamination). The colony forming efficiency (CE) was calculated as:

$$CE = \frac{\text{Number of Cell inoculated}}{\text{Number of Colony Grown}} \times 100\%$$

The results were listed in table 33.

TABLE 37

Colony Forming Efficiency (CE) in groups of cells

| Group | Number | Normal cell colony (CE) | Malignant transformed cell colony (CE) |
| --- | --- | --- | --- |
| A: 10.0 mg/flask | 9 | 22.6 ± 11.8 | 0 |
| B: 5.0 mg/flask | 8 | 27.9 ± 13.7 | 0 |
| C: 2.5 mg/flask | 7 | 17.0 ± 7.8 | 0 |
| D: 1.25 mg/flask | 10 | 20.6 ± 9.2 | 0 |
| E: 0.625 mg/flask | 9 | 12.6 ± 6.7 | 00 |
| Positive Control | 8 | 2.6 ± 4.5 | 4.4 ± 3.7 |
| Negative control | 10 | 19.4 ± 12.6 | 0 |

Conclusion

There was no malignant transformed cell colony that was discovered in the groups of CCP. The criteria for the malignant cells determination we adopted was that of the Dunkle criteria (1981). As a conclusion, CCP is of no positive carcinogensis effect upon Syrian Hamster embryo cell.

Clinical Trial of CCP

Total amount of cases: 150 (100 cases in the CCP group, 50 cases in the control groups). Both from outpatient and inpatient departments in the following three units:

Department of Gynecology, Hospital of TMC, Jiangsu, People's Republic of China.

Department of Gynecology, Hospital of TMC, Nanjing, People's Republic of China.

Department of TCM, Obstetrical and Gynecological Hospital, Nanjing, Jiangsu, People's Republic of China.

Patients age: 20~54, max 63, min 20, average 37; Course of illness: max 17 years, min 1 month, average 25.59 months (Refer to Tables 38 and 39 for distribution of age and courses). All the 150 cases were randomly grouped as: 100 cases in the CCP drug group and 50 cases in the control group.

There was a match-pair grouping within the 100 cases of CCP drug group. Among the 100 patients, 50 cases were chosen for the match-pair group (A), which included cases of intramural hysteromyoma and that of chronic pelvic inflammations with inflammatory lower abdomen masses. The other 50 patients were designed to be in the non-pair group (C), which included diseases of dysmenorrheas, dysfunctional uterine bleeding caused by irregular shedding of endometrim, hemotcele of uterine cavity, remote extrauterine pregnancy, and postpartum lochiorrhea atc. The control group was categorized as (B).

The match-pair group (A) was intended to be as similar as possible to group B regarding severity of diseases, courses, ages, etc.

Diagnoses Based on Symptoms in TCM

Symptom Class A:
  Profuse menstruation
  Non-stop Metrostaxis
  Excess of blood clots during menstrual period
  Inflammatory lower abdomen mass (es)
  Vague pain, distending pain or press refusal at lower abdomen
  Dim purpuric spots in tongue (TCM index)
  Faint wrist pulse (TCM index)

Symptom Class B:
  Lumber pain
  Large amount of leulorrhea
  Heavy and distending anus
  Symptoms get worse during menstruation or periods of tiredness Symptom of Lab Tests (Class C)
  Abnormal indexes in blood rheology
  Increased blood platelet aggregation, or enhanced release of blood platelet Diagnosis in Western Traditional Medicine 1) Small Leiomyoma uteri
  Lower abdomen mass(es)
  Profuse or prolonged menstruation, excess of blood clots during menstrual period, vague pain, distending pain at lower abdomen, or anemia.
  Enlarged uterine, but no larger than a pregnant uterine of 2 months (rigid or ultra sound proved).

2) Chronic Pelvic Inflammations with Inflammatory Lower Abdomen Masses
  Symptoms: vague pain, distending pain, heavy or distending lower abdomen, and lumber pains. Symptoms get worse during menstruation or periods of tiredness. Other symptoms include slightly high temperature, heavy and distending anus, and large amount of leulorrhea.
  Signs: mostly posterior uterine or fixed uterine. Perceivable rope shaped rigid mass at one side of uterine that could generate pain when the area is pressed. Masses or thicker tissues can be felt in one or both sides of the uterine. B-ultrasound proved.

3) Dysfunctional Uterine Bleeding caused by Irregular Shedding of Endometrim.
  Symptoms: prolonged period of menstruation in a normal month circle (more than seven days). Large amounts of blood during menstruation with black blots or distending pain at lower abdomen.
  Clinical signs: normal circle with two-phase body temperature curve. Temperature would not fall to its level of follicular phase after the beginning of menstruation. Physical exam or B ultrasound demonstrated that there were no organic changes Criteria of TCM for Enlistment of Patients:
1) More than 3 items of class A,
2) Or, one item of class A plus two items class C
3) Or, one item of class A plus two items of class B and one item of class C
4) Anyone's diagnosis in the three western traditional medicines Exclusion of Cases:
1) Patients with other organic diseases, abdomen masses in women with postmenopausal period or found to be malignant.
2) Interruption of treatment, uncompleted data record.
3) Patients were screened by blood routine test that included blood platelets counting, bleeding and coagulating time, hepatic and kidney function tests. The abnormal menstruation caused by blood, hepatic or kidney function was eliminated.

Method:
  Capsule of *Cinnamomi* and *Poria*, three capsules each administration, three times a day. Control group will take Bolus of *Cinnamomi* and *Poria* one bolus each time, three times a day for 3 months. For patients of intramural hysteromyoma, stop the administration during menstruation. For patients of dysfunctional uterine bleeding, stop the administration right after bleeding.

Lab Tests:
  Except for the routine blood tests, all patients were required to take the following:
  Aggregation ratio of blood platelet for 1 and 5 minutes
  Ratio of whole blood viscosity
  Ratio of plasma viscosity
  Erythrocyte sedimentation
  Packed blood cell volume
  Reduced whole blood viscosity
  K value of sedimentation Points for Judgment of Effectiveness:
  For small intramural hysteromyoma: enlarged uterine, irregular shape of uterine, large amount of menstruation and excess of black clots (the patient got five points for each of the above). Non-stopped Metrostaxis, vague pain in lower abdomen, distending pain or press refusal (the patient got two points).
  For chronic pelvic inflammations with inflammatory lower abdomen masses: confined or fixed uterine and/or tenderness, rigid or rope shaped oviduct and/or tenderness. Thickened tissue in one or both side of uterine and/or tenderness, mass in one or both side of pelvic cavity (the patient got five points for each). For aching pains in lower abdomen or lumber, the patient got three points. For large amounts of leulorrhea, and if symptoms worsen during menstruation or periods of tiredness, the patient got two points.
  For dysfunctional uterine bleeding caused by irregular shedding of endometrim: prolonged menstruation for more than seven days, large amount of menstruation, excess of blood blots, luteal phase for 12~14 days or it would not fall to its level of follicular phase after the starting of menstruation (the patient got five points for each of these symptoms). For pain in the lower abdomen, the patient got two points.
  For all diagnosis, if dim purpuric spots in tongue or faint wrist pulse were observed, add 1 point for each. Half a point is given for each additional year of illness if the diagnosis is small intramural hysteromyoma or chronic pelvic inflammations with inflammatory lower abdomen masses. Half a point for every three months if the diagnosis is dysfunctional uterine bleeding caused by irregular shedding of endometrim.

Degree of Severity:
 Serious: >20 points
 Medium: 10~20 points
 Slight: <10 points Definition and Evaluation of Effectiveness:
1) Rehabilitation: recovered from any symptoms, abnormal physical signs and lab tests. Total point =0 and no recurrence within 6 month after treatment.
2) Obvious effect: revered from any symptoms, abnormal physical signs. Index of lab test improved obviously, at least ⅔ lower the total points than that of before treatment
3) Improved: some of the symptoms, abnormal physical signs and lab tests improved. A ⅓ reduction in the total amount of points when compared to the amount obtained before the treatment.
4) No effect: no improvement.

Results
1) See Table 40 for comparison of points and table 41 for improvement rate between groups. Table 40 and 41 shows the improvement of the symptoms. They show both CCP and BCP groups are getting better than those before treatment. No significant different between these 2 groups
2) See table 5 for changes of abnormal physical signs
3) Table 43 shows changes of lab tests (blood rheology, platelets etc.) of patient groups before and after treatment.
 CCP groups A: rehabilitation 14 (28%), obvious effect 16, and improvement 18. Rehabilitation plus obvious effect 60%, total effective rate 96%.
 BCP group (control): R 12, OE 17, and IM 15. R rate 24%, R+OE rate 58%, total off rate 88%, $X^2$ test demonstrate that no significant difference between the 2 groups (P>0.05)
 CCP A+C group (100 cases): R rate 27%, R+OE rate 58%, total off rate 96%
 Five patients (three cases in CCP, 3% and two in BCP, 4% group) complained of a slight pain or discomfort in their upper abdomen after taking the drugs. They all recovered in two to three hours after they stopped using the drug or took the advice of using the drug only after meals.

Discussion
In TCM diagnosis system, the above mentioned multiple diagnosis: primary or secondary dysmenorrhea, dysfunctional uterine bleeding caused by irregular shedding of endometrium, chronic pelvic inflammations with inflammatory lower abdomen masses or small intramural hysteromyoma are under the same title of diagnostic catalog in TCM and are considered to share the same etiological cause. They were studied and treated the same way with the same drugs.

The title is "Diseases of Blood Stasis" in OB/GYN. The common age of such diseases is 25~54 (women of childbearing age). The course of such diseases ranges from 1 month to 17 years.

Both CCP and BCP may reduce the symptoms of such diseases, especially for the following symptoms in Class A and B (improvement of more than 80%) profuse menstruation, non-stopped Metrostaxis, excess of blood clots during menstrual period, vague pain or distending pain lower abdomen, aching pain at lumber, heavy and distending anus. For other symptoms in Class A and B, there was a 70% improvement. Effect of CCP and BCP on above symptoms showed no significant difference (table 37)

Abdomen masses detected by physical examinations or B-ultrasound in patients with inflammatory lower abdomen masses or small intramural hysteromyoma: in CCP groups the physical exam showed 28% of masses had disappeared, 36% shrank, 44% were controlled in size, and 2% enlarged. On B-ultrasound screen 30% disappeared, 36% shrank, 32% were controlled in size, and 2% enlarged. In BCP, similar results were found. There was no significant difference between the two groups (P>0.05) (table 42)

Total points: both CCP and BCP groups showed differences before and after the treatment (P<0.001). No significant differences were found between the two groups in any single diagnosis (P>0.05) except that in the matched pairs analysis, the point fall in CCP was larger than that of BCP (P≈0.05) table 43.

In observation of the laboratory study made with the different groups, the six indexes of blood rheology study and the two indexes for platelet aggregation were carefully recorded and analyzed. The CCP group showed significant differences after treatment in each of the eight indexes while BCP changes were noticeable in six out of the eight (except aggregation ratio of platelet at one minute and erythrocyte sedimentation). The results show that CCP or BCP could change the condition of the blood flow and circulation. For unknown reasons, comparison between match pair groups A and B showed that there were some significant differences between the two groups except for the ratio of whole blood viscosity and reduced whole blood viscosity. It was indicated that CCP had stronger effects on blood flow.

In laboratory studies, CCP showed positive results in improving typical symptoms and complains, physical signs and examinations, and blood flow indexes. The capsule appears to be as effective as BCP which is a successful TCM preparation in treating the above-mentioned diseases and had been practiced for decades in China. The CCP even showed ore benefits than the BCP.

TABLE 38

Distribution of disease duration in the groups

| Group | Dignosis | Number of Case | Max (month) | Min (month) | $\overline{X}$ | S | $t_{\overline{X1}\text{-}\overline{X}}$ |
|---|---|---|---|---|---|---|---|
| A | LU + IM | 50 | 100 | 1 | 25.92 | 34.3908 | 0.1308 |
| B | LU + AIM | 50 | 204 | 1 | 24.98 | 37.3928 | |
| C | DUB etc. | 50 | 156 | 1 | 25.86 | 33.0972 | |
| A + C | Mixed cases | 100 | 100 | 1 | 25.89 | 33.9720 | |
| A | LU | 25 | 100 | 2 | 29.92 | 37.5488 | 0.1598 |
| | IM | 25 | 120 | 1 | 21.92 | 31.1688 | 0.0341 |
| B | LU | 25 | 204 | 2 | 20.36 | 40.0145 | |
| | IM | 25 | 160 | 1 | 21.60 | 35.0678 | |

LU: Leiomyoma Uteri;
IM: Inflammatory Mass;
DUB: Dysfunctional Uterine Bleeding

TABLE 39

Changes in points before and after treatment

| Group | Diag. | case | Before treatment $\overline{X}$ | S | After treatment $\overline{X}$ | S | Subtract of points $\overline{d}$ | Sd | tα | $t_{\overline{x1}-\overline{x1}}$ |
|---|---|---|---|---|---|---|---|---|---|---|
| A | LU + IM | 50 | 21.5 | 6.3374 | 5.11 | 4.9315 | 16.39 | 6.0426 | 19.1796 | 1.9123 |
| B | LU + IM | 50 | 20.72 | 7.5958 | 6.77 | 6.3465 | 13.95 | 6.7000 | 14.7225 | |

| Group | 25-34 yr. (%) | 35-44 yr. (%) | 45-54 yr. (%) | Total | X² |
|---|---|---|---|---|---|
| A | 16 (32) | 26 (52) | 8 (16) | 50 | 0.000 |
| B | 16 (32) | 26 (52) | 8 (16) | 50 | |
| C | 27 (54) | 13 (26) | 10 (20) | 50 | |
| A + C | 43 (43) | 39 (39) | 18 (18) | 100 | |

| Group | Diag. | case | Before treatment $\overline{X}$ | S | After treatment $\overline{X}$ | S | Subtract of points $\overline{d}$ | Sd | tα | $t_{\overline{x1}-\overline{x1}}$ |
|---|---|---|---|---|---|---|---|---|---|---|
| C | DUB | 50 | 17.96 | 7.7800 | 6.10 | 5.8379 | 11.86 | 6.6078 | 12.6914 | |
| A + C | Mixed cases | 100 | 19.73 | 7.2803 | 5.605 | 5.3994 | 14.125 | 6.6982 | 21.0878 | |
| A | LU | 25 | 24.06 | 4.9986 | 6.44 | 5.5945 | 17.62 | 6.6274 | 13.2933 | 1.7981 |
|  | IM | 25 | 18.94 | 6.5849 | 3.78 | 3.8299 | 15.16 | 5.2415 | 14.4615 | 0.83514 |
| B | LU | 25 | 22.34 | 7.5605 | 8.22 | 6.7628 | 14.12 | 7.1272 | 9.9057 | |
|  | IM | 25 | 19.10 | 7.4274 | 5.32 | 5.6677 | 13.78 | 6.3870 | 10.7876 | |

TABLE 40

Changes in Clinical symptoms

| Symptoms | Group | Cases observed before treatment | Cases improved After treatment | Rate of improvement (%) | X² |
|---|---|---|---|---|---|
| Profuse menstruation | A | 29 | 27 | 93.10 | 0.668 |
|  | B | 28 | 24 | 85.71 | |
|  | C | 40 | 39 | 97.50 | |
|  | A + C | 69 | 66 | 95.65 | |
| Non-stopped Metrostaxis | A | 21 | 18 | 85.71 | 0.013 |
|  | B | 19 | 16 | 84.21 | |
|  | C | 20 | 18 | 90.00 | |
|  | A + C | 41 | 36 | 87.8 | |
| Lots of blood clots during menstrual period | A | 33 | 31 | 93.94 | 0.059 |
|  | B | 34 | 30 | 88.24 | |
|  | C | 44 | 42 | 95.45 | |
|  | A + C | 77 | 73 | 94.81 | |
| Vague pain at lower abdomen | A | 47 | 45 | 95.74 | 1.14 |
|  | B | 48 | 43 | 89.58 | |
|  | C | 35 | 34 | 97.14 | |
|  | A + C | 82 | 79 | 96.34 | |
| Dim purpuric spots in tongue | A | 32 | 25 | 78.13 | 0.154 |
|  | B | 33 | 24 | 72.73 | |
|  | C | 31 | 27 | 87.10 | |
|  | A + C | 63 | 52 | 82.54 | |
| Faint wrist pulse | A | 34 | 27 | 79.41 | 0.155 |
|  | B | 31 | 23 | 74.19 | |
|  | C | 33 | 27 | 81.82 | |
|  | A + C | 67 | 54 | 80.60 | |
| Aching pain at lumber | A | 36 | 32 | 38.89 | 1.249 |
|  | B | 30 | 23 | 76.67 | |
|  | C | 34 | 31 | 91.18 | |
|  | A + C | 70 | 60 | 90 | |
| Large amount of leulorrhea | A | 25 | 22 | 88.0 | 0.003 |
|  | B | 24 | 21 | 87.50 | |
|  | C | 19 | 15 | 78.95 | |
|  | A + C | 43 | 36 | 83.72 | |
| Heavy and distending anus | A | 17 | 16 | 74.12 | 0.257 |
|  | B | 18 | 16 | 83.89 | |
|  | C | 15 | 14 | 93.33 | |
|  | A + C | 32 | 30 | 93.75 | |
| Symptoms get worse during menstruation or exhaustion | A | 18 | 14 | 77.78 | 0.022 |
|  | B | 16 | 12 | 75 | |
|  | C | 20 | 17 | 85 | |
|  | A + C | 38 | 31 | 81.58 | |

TABLE 41

Changes of abdomen masses in physical examination and B-ultrasound

| | Group | Cases | Vanished (%) | Shrunk (%) | No change (%) | Enlarged (%) | Mean grade | |
|---|---|---|---|---|---|---|---|---|
| Physical exam | A | 50 | 14 (28) | 13 (26) | 22 (41) | 1 (2) | 2.80 | 0.1443 |
|  | B | 50 | 9 (18) | 22 (44) | 16 (32) | 3 (6) | 2.74 | |
| B-ultrasound | A | 50 | 15 (30) | 18 (36) | 16 (32) | 1 (2) | 2.96 | 0.2337 |
|  | B | 50 | 8 (16) | 22 (44) | 12 (24) | 3 (6) | 2.50 | |

TABLE 42-1

Changes in indexes in blood rheology

| item | Grp | before $\overline{X1}$ | S1 | After $\overline{X2}$ | S2 | Subtract $\overline{d} - S\overline{d}$ | | $t\overline{d}$ | $t_{\overline{d1}\text{-}\overline{d2}}$ |
|---|---|---|---|---|---|---|---|---|---|
| Ratio | A | 1.532 | 0.167 | 1.460 | 0.219 | 0.0724 | 0.0293 | 2.469 | 1.2856 |
| of | B | 1.591 | 0.150 | 1.512 | 0.192 | 0.079 | 0.0214 | 3.688 | |
| whole | C | 1.577 | 0.286 | 1.502 | 0.282 | 0.026 | 0.0250 | 1.023 | |
| blood | A + C | 1.554 | 0.235 | 1.531 | 0.261 | 0.023 | 0.0116 | 1.989 | |
| viscosity | | | | | | | | | |
| Ratio | A | 1.585 | 0.108 | 1.530 | 0.129 | 0.055 | 0.0176 | 3.104 | 8.1715 |
| of | B | 1.620 | 0.120 | 1.536 | 0.127 | 0.084 | 0.0184 | 4.571 | |
| plasma | C | 1.577 | 0.285 | 1.527 | 0.128 | 0.050 | 0.040 | 1.250 | |
| viscosity | A + C | 1.597 | 0.124 | 1.531 | 0.127 | 0.066 | 0.0128 | 5.140 | |
| Erythrocyte | A | 20.860 | 14.777 | 4.620 | 10.825 | 4.240 | 1.721 | 2.463 | 13.0023 |
| sedimentation | C | 25.160 | 11.467 | 3.760 | 10.3205 | 1.400 | 1.035 | 1.352 | |
| | A + C | 27.010 | 13.027 | 4.190 | 10.583 | 2.820 | 1.009 | 2.7940 | |
| Packed | A | 40.940 | 6.769 | 39.480 | 5.7365 | 1.460 | 1.050 | 1.391 | 3.4771 |
| blood | B | 43.327 | 4.233 | 41.135 | 4.530 | 2.202 | 1.084 | 2.031 | |
| cell | C | 41.600 | 5.341 | 40.380 | 4.060 | 1.220 | 0.719 | 1.698 | |
| volume | A + C | 41.270 | 6.106 | 39.930 | 4.990 | 1.340 | 0.633 | 2.117 | |
| Reduced | A | 10.1022 | 2.720 | 9.604 | 2.392 | 0.499 | 0.293 | 1.700 | 0.785 |
| whole | B | 9.849 | 2.717 | 9.307 | 2.380 | 0.542 | 0.259 | 2.094 | |
| blood | C | 9.865 | 3.002 | 9.556 | 2.665 | 0.309 | 0.501 | 0.616 | |
| viscosity | A + C | 9.984 | 2.871 | 9.580 | 2.523 | 0.404 | 0.203 | 1.991 | |
| K | A | 93.408 | 43.377 | 78.809 | 36.608 | 14.599 | 4.726 | 3.089 | 7.383 |
| value | B | 97.815 | 47.710 | 89.168 | 34.789 | 8.647 | 3.188 | 2.712 | |
| of | C | 86.106 | 36.955 | 78.599 | 33.239 | 7.512 | 2.937 | 1.861 | |
| sedimentation | A + C | 89.757 | 40.461 | 78.704 | 34.912 | 11.053 | 3.112 | 3.552 | |

TABLE 42-2

Changes in aggregation of platelet

| item | group | N | Before $\overline{X1}$ | $S_1$ | After $\overline{X2}$ | $S_2$ | Subtract $\overline{d} - S\overline{d}$ | | $t\overline{d}$ | $t_{\overline{d1}\text{-}\overline{d2}}$ |
|---|---|---|---|---|---|---|---|---|---|---|
| 1' | A | 42 | 42.647 | 20.874 | 35.210 | 16.431 | 7.437 | 2.300 | 3.233 | 11.864 |
| | B | 44 | 39.620 | 16.379 | 40.872 | 17.313 | 1.244 | 2.529 | 0.492 | |
| | C | 48 | 45.613 | 21.483 | 43.030 | 15.960 | 2.581 | 3.025 | 0.854 | |
| | A + C | 90 | 44.130 | 21.127 | 39.120 | 16.212 | 5.010 | 2.103 | 2.382 | |
| 5' | A | 42 | 65.475 | 26.325 | 53.245 | 24.062 | 12.232 | 3.978 | 3.075 | 5.245 |
| | B | 44 | 56.256 | 25.758 | 48.092 | 26.328 | 8.164 | 3.188 | 2.561 | |
| | C | 48 | 63.490 | 25.715 | 63.637 | 21.951 | 0.148 | 0.148 | 0.118 | |
| | A + C | 90 | 64.420 | 26.015 | 58.440 | 23.480 | 5.980 | 2.981 | 2.006 | |

TABLE 43

Comparison of drug effectiveness between groups

Comprehensive analysis

| Group | reha-bili-tation | Obvious effect | improved | No effect | n | Ratio of Reha-bilitation | $X^2$ |
|---|---|---|---|---|---|---|---|
| A | 14 | 16 | 18 | 2 | 50 | 14 (24.0) | 0.2079 |
| B | 12 | 17 | 15 | 6 | 50 | 12 (24.0) | |
| C | 13 | 15 | 18 | 4 | 50 | 13 (26.0) | |
| A + C | 27 | 31 | 36 | 6 | 100 | 26 (27.0) | 0.1559 |

| group | Ratio of obvious effect | $X^2$ | Total effective rate(%) | $X^2$ | μ |
|---|---|---|---|---|---|
| A | 30 (60.0) | 0.0413 | 48 (96.0) | 2.1739 | 0.2887 |
| B | 29 (58.0) | | 44 (88.0) | | |
| C | 28 (56.0) | | 46 (92.0) | | |
| A + C | 58 (58.0) | 0.2 | 94 (94.0) | 1.6304 | |

REFERENCES

1. Wenzloff N J, Shimp L, *Therapeutic management of primary dysmenorrhea*. Drug Intell Clin Pharm 1984January; 18 (1):22-6]; Lela Kruse R N, *Dysmenorrhea—painful menstrual cramps*, http://coninfo.nursing.uiowa.edu
2. Current concepts in the etiology and treatment of primary dysmenorrhea Acta Obstet Gynecol Scand Suppl 1986; 138: 7-10
3. *Dysmenorrhea. Women Health* 1983 Summer-Fall; 8(2-3): 91-106; *Dysmenorrhea during adolescence*. Acta Obstet Gynecol Scand Suppl 1979; 87: 61-6
4. Dawood M Y, *Nonsteroidal anti-inflammatory drugs and changing attitudes toward dysmenorrhea*. Am J Med May 20, 1988 ; 84(5A):23-9
5. Asch R H, Greenblatt R B, *Primary and membranous dysmenorrhea*. South Med J October 1978; 71(10):1247-9, 1252 *Relief From Menstrual Cramps*, Estronaut, a forum for women's health, http://www.estronaut.com
6. Wangzhaoyi, Wangdengke etc. Journal of Yunnan College of Traditional Chinese Medicine 11(4):28 1982
7. Xiejiajun, Renshiping etc.: Research of Traditional Chinese Medicine (5):24, 1986

8. Teaching Materials of "the Golden Chamber", edited by Hubei College of Traditional Chinese Medicine pp 203. Published by Shanghai Science Publishing Company in September of 1963.

What is claimed is:

1. A method for treating primary dysmenorrhea in a subject suffering therefrom comprising administering to the subject an effective amount of a composition comprising extracts from the stem of *Cinnamomum cassia*, sclerotium of *Poria cocos*, root bark of *Paeonia suffruticosa*, root of *Paeonia lactiflora* and seed of *Prunus persica* or *Prunus davidiana*, wherein the composition comprises:
   a) 1.3-1.9% Paeoniflorin and
   b) 0.7-1.1% Paeonol.

2. The method of claim 1 wherein the stem of *Cinnamomum cassia*, sclerotium of *Poria cocos*, root bark of *Paeonia suffruticosa*, root of *Paeonia lactiflora* and seed of *Prunus persica* or *Prunus davidiana* are obtained from cultivated plants.

3. The method of claim 1 wherein the composition further comprises a pharmaceutically acceptable carrier.

4. The method of claim 3 wherein the composition is formulated in the form of a pill, capsule, granule, tablet, suspension, injection, syrup or tincture.

5. A method for alleviating clinical symptoms of primary dysmenorrhea in a subject suffering therefrom comprising administering to the subject an effective amount of a composition comprising extracts from the stem of *Cinnamomum cassia*, sclerotium of *Poria cocos*, root bark of *Paeonia suffruticosa*, root of *Paeonia lactiflora* and seed of *Prunus persica* or *Prunus davidiana*, wherein the composition comprises:
   a) 1.3-1.9% Paeoniflorin and
   b) 0.7-1.1% Paeonol.

6. The method of claim 5 wherein the stem of *Cinnamomum cassia*, sclerotium of *Poria cocos*, root bark of *Paeonia suffruticosa*, root of *Paeonia lactiflora* and seed of *Prunus persica* or *Prunus davidiana* are obtained from cultivated plants.

7. The method of claim 5 wherein the composition further comprises a pharmaceutically acceptable carrier.

8. The method of claim 7 wherein the composition is formulated in the form of a pill, capsule, granule, tablet, suspension, injection, syrup or tincture.

9. A method for alleviating leucorrhea, or pains associated with primary dysmenorrhea, in a subject suffering therefrom administering to the subject an effective amount of a composition comprising extracts from the stem of *Cinnamomum cassia*, sclerotium of *Poria cocos*, root bark of *Paeonia suffruticosa*, root of *Paeonia lactiflora* and seed of *Prunus persica* or *Prunus Davidiana*, wherein the composition comprises:
   a) 1.3-1.9% Paeoniflorin and
   b) 0.7-1.1% Paeonol.

10. The method of claim 9 wherein the stem of *Cinnamomum cassia*, sclerotium of *Poria cocos*, root bark of *Paeonia suffruticosa*, root of *Paeonia lactiflora* and seed of *Prunus persica* or *Prunus davidiana* are obtained from cultivated plants.

11. The method of claim 9 wherein the composition further comprises a pharmaceutically acceptable carrier.

12. The method of claim 11 wherein the composition is formulated in the form of a pill, capsule, granule, tablet, suspension, injection, syrup or tincture.

* * * * *

UNITED STATES PATENT AND TRADEMARK OFFICE
CERTIFICATE OF CORRECTION

PATENT NO. : 7,691,387 B2
APPLICATION NO. : 11/389441
DATED : April 6, 2010
INVENTOR(S) : Wei Xiao Page 1 of 1

It is certified that error appears in the above-identified patent and that said Letters Patent is hereby corrected as shown below:

In column 21, line 24, "Irvhd max$^{KBr}$" should be -- Irv$_{max}^{KBr}$ --

In column 65, lines 6-13, claim 1, "A method for treating primary dysmenorrhea in a subject suffering therefrom comprising" should be -- A method for treating primary dysmenorrhea in a subject suffering therefrom, comprising --

In column 65, lines 24-26, claim 5, "A method for alleviating clinical symptoms of primary dysmenorrhea in a subject suffering therefrom comprising" should be -- A method for alleviating clinical symptoms of primary dysmenorrhea in a subject suffering therefrom, comprising --

In column 66, lines 11-14, claim 9, "A method for alleviating leucorrhea, or pains associated with primary dysmenorrhea, in a subject suffering therefrom administering" should be -- A method for alleviating leucorrhea, or pains associated with primary dysmenorrhea, in a subject suffering therefrom, comprising administering --

Signed and Sealed this

Twenty-second Day of June, 2010

David J. Kappos
*Director of the United States Patent and Trademark Office*